US010781161B2

(12) United States Patent
Shulman et al.

(10) Patent No.: US 10,781,161 B2
(45) Date of Patent: Sep. 22, 2020

(54) THERAPEUTIC DNP DERIVATIVES AND METHODS USING SAME

(71) Applicant: Yale University, New Haven, CT (US)

(72) Inventors: Gerald I. Shulman, East Haven, CT (US); David A. Spiegel, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 16/419,949

(22) Filed: May 22, 2019

(65) Prior Publication Data

US 2020/0087242 A1    Mar. 19, 2020

Related U.S. Application Data

(63) Continuation of application No. 14/914,408, filed as application No. PCT/US2014/053127 on Aug. 28, 2014, now Pat. No. 10,457,629.

(60) Provisional application No. 61/872,279, filed on Aug. 30, 2013.

(51) Int. Cl.
 *C07C 205/37* (2006.01)
 *A61K 31/085* (2006.01)
 *C07J 41/00* (2006.01)

(52) U.S. Cl.
 CPC .......... *C07C 205/37* (2013.01); *A61K 31/085* (2013.01); *C07J 41/0055* (2013.01)

(58) Field of Classification Search
 CPC ........................... C07C 205/37; A61K 31/085
 See application file for complete search history.

(56) References Cited

U.S. PATENT DOCUMENTS

| | | | |
|---|---|---|---|
| 2,183,589 | A | 12/1939 | Reichstein |
| 3,081,224 | A | 3/1963 | Thorson et al. |
| 3,419,620 | A | 12/1968 | Heinz-Manfred et al. |
| 4,695,656 | A | 9/1987 | Reh et al. |
| 5,851,546 | A | 12/1998 | Mashelkar et al. |
| 5,866,514 | A | 2/1999 | Sugisawa et al. |
| 6,664,297 | B1 | 12/2003 | Ferreira et al. |
| 2008/0234352 | A1 | 9/2008 | Fischer et al. |
| 2010/0056643 | A1 | 3/2010 | Bachynsky et al. |
| 2012/0022054 | A1 | 1/2012 | Benarous et al. |
| 2012/0094898 | A1 | 4/2012 | Asami et al. |
| 2012/0277286 | A1 | 11/2012 | Youle et al. |

FOREIGN PATENT DOCUMENTS

| | | | |
|---|---|---|---|
| CA | 774573 | A | 12/1967 |
| WO | 9955774 | A1 | 11/1999 |
| WO | 2004041256 | A2 | 5/2004 |

OTHER PUBLICATIONS

PCT International Search Report and Written Opinion for PCT International Application No. PCT/US2014/053127 dated Mar. 18, 2015.
Addendum to the Toxicological Profile for Dinitrophenols, Agency for Toxic Substances and Disease Registry Division of Toxicology and Environmental Medicine ,Mar. 2011.
Guidance for Industry Estimating the Maximum Safe Starting Dose in Initial Clinical Trials for Therapeutics in Adult Healthy Volunteers, U.S. Department of Health and Human Services, Food and Drug Administration, Center for Drug Evaluation and Research ,2005 ,1-27.
Cohen, et al.,Trace determination of phenols by gas chromatography as their 2,4-dinitrophenyl ethers, Journal of Chromatography A 44 ,1969 ,251-255.
De Felice, et al., Novel neuroprotective, neuritogenic and anti-amyloidogenic properties of 2,4-dinitrophenol: The gentle face of Janus, IUBMB Life. 58(4) ,2006 ,185-191.
Gruber, et al., Mitochondria-targeted antioxidants and metabolic modulators as pharmacological interventions, Biotechnol Adv. 31(5) ,2013 ,563-592.
Grundlingh, et al.,2,4-dinitrophenol (DNP): a weight loss agent with significant acute toxicity and risk of death, J Med Toxicol. 7(3) ,Sep. 2012 ,205-212.
Harper, et al., Mitochondrial uncoupling as a target for drug development for the treatment of obesity, Obes Rev. 2 (4) ,2001 ,255-265.
Harris, et al.,Toxicological Profile for Dinitrophenols, U.S. Department of Health and Human Services Public Health Service Agency for Toxic Substances and Disease Registry ,Aug. 1995.
Marrache, et al.,Engineering of blended nanoparticle platform for delivery of mitochondria-acting therapeutics, Proc Natl Acad Sci U S A. 109(40) ,2012 ,16288-16293.
Perry, et al.,Controlled-release mitochondrial protonophore reverses diabetes and steatohepatitis in rats, Science. 347(6227) ,2015 ,1253-1256.
Perry, et al.,Reversal of Hypertriglyceridemia, Fatty Liver Disease, and Insulin Resistance by a Liver-Targeted Mitochondrial Uncoupler, Cell Metab. 18(5) ,2013 ,740-748.
Perry, et al.,Supplementary Material (pp. 1 to 29) for Controlled-release mitochondrial protonophore reverses diabetes and steatohepatitis in rats, Science 347(6227) ,2015 ,1253-1256.
Robert, et al.,Plasma levels and kinetic disposition of 2,4-dinitrophenol and its metabolites 2-amino-4-nitrophenol and 4-amino-2-nitrophenol in the mouse, J Chromatogr. 344 ,Nov. 1985 ,177-186.
Samuel, et al.,Mechanism of hepatic insulin resistance in non-alcoholic fatty liver disease, J Biol Chem. 279(31) ,Jul. 30, 2004 , 32345-32353.
Blaikie, et al., "Targeting dinitrophenol to mitochondria: limitations to the development of a self-limiting mitochondrial protonophore", Biosci Rep. 26(3), Jun. 2006, 231-243.

*Primary Examiner* — Barbara P Badio
(74) *Attorney, Agent, or Firm* — Saul Ewing Arnstein & Lehr LLP; Kathryn Doyle; Domingos J. Silva

(57) ABSTRACT

The present invention includes DNP derivatives that are useful for preventing or treating a metabolic disease or disorder in a subject in need thereof. In certain embodiments, the subject is further administered at least one additional therapeutic agent.

20 Claims, 57 Drawing Sheets

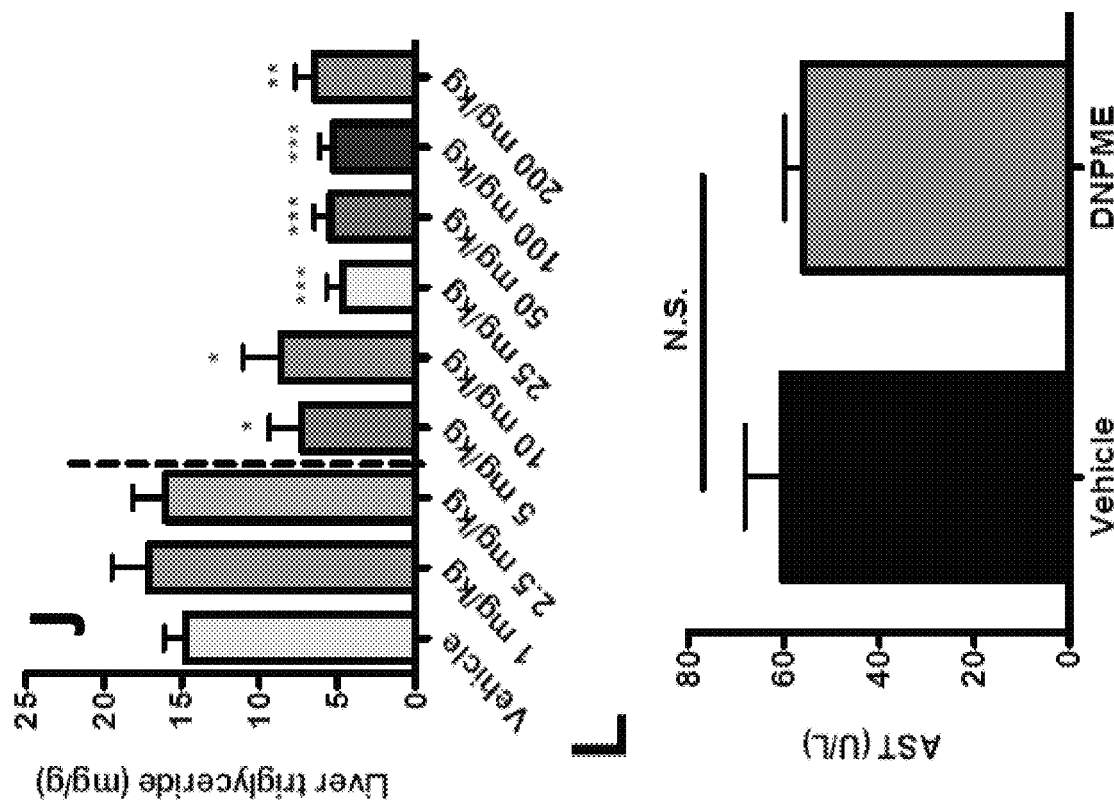
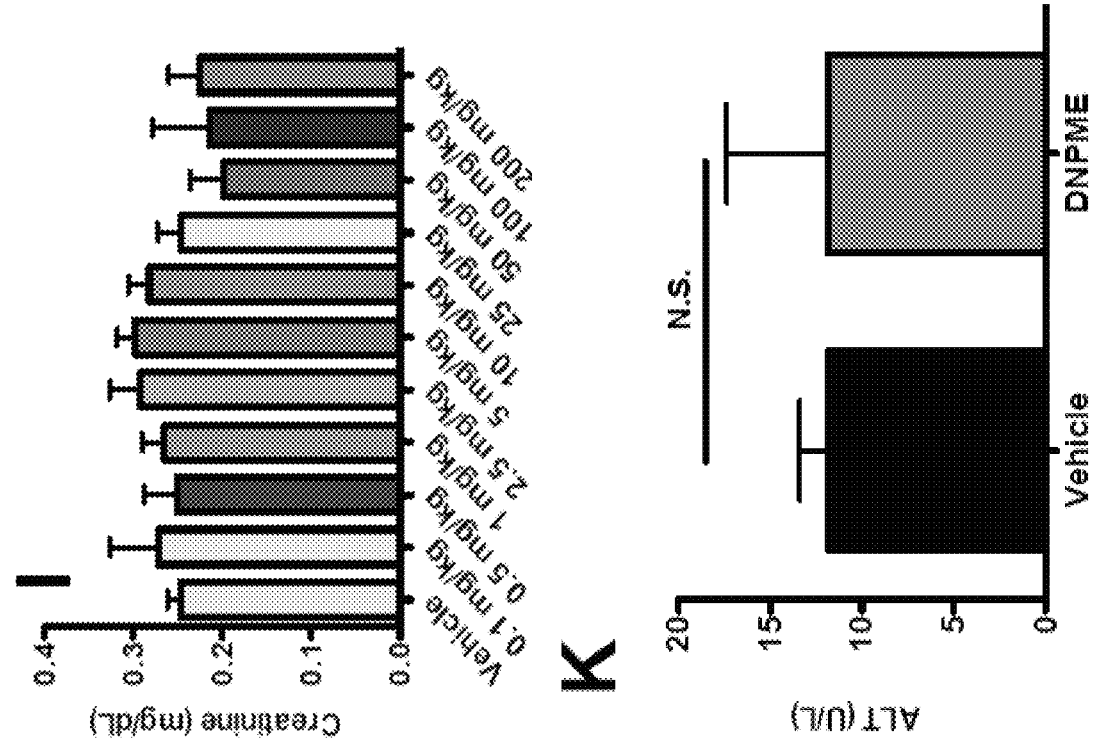
Figs. 1I-1L

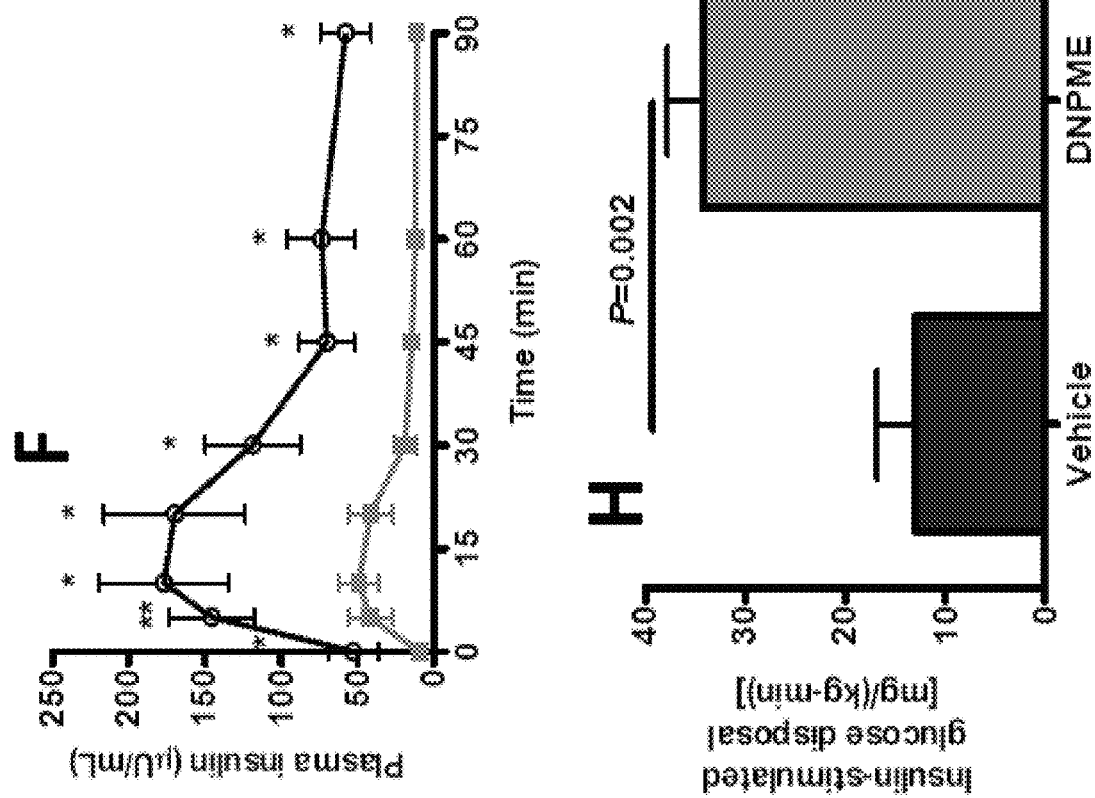
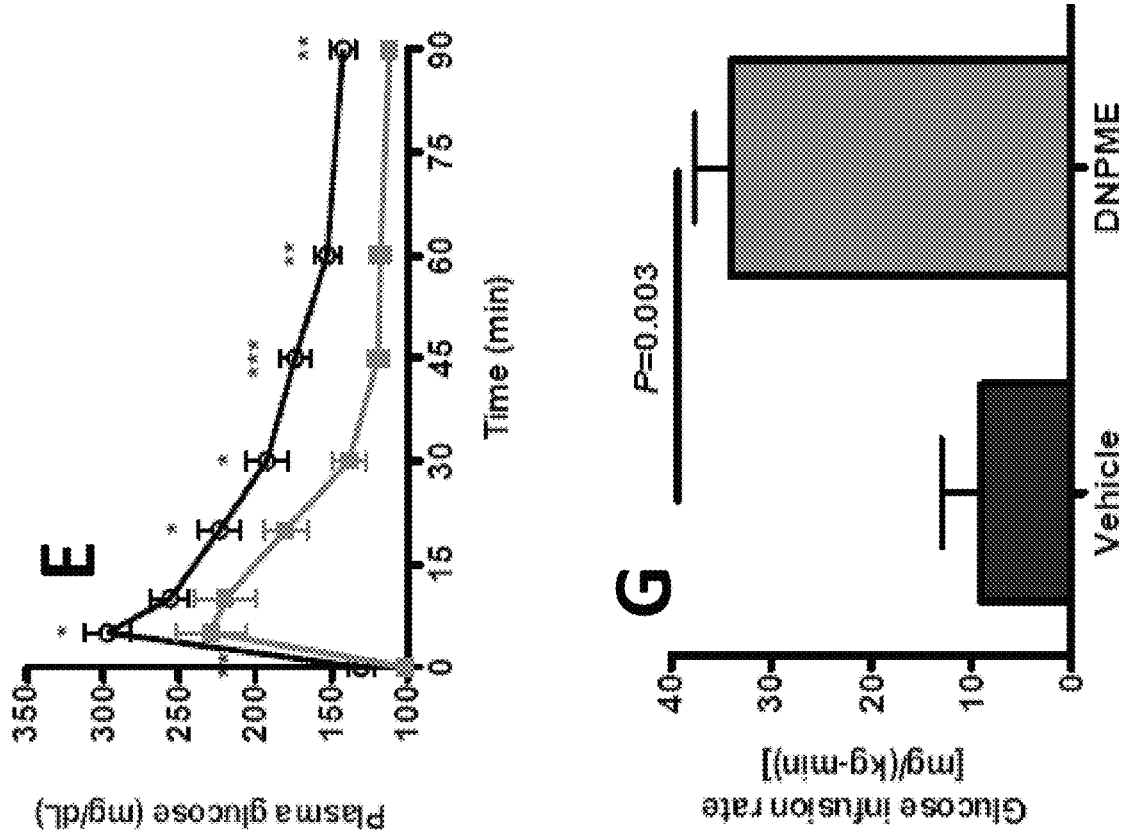
Figs. 2E-2H

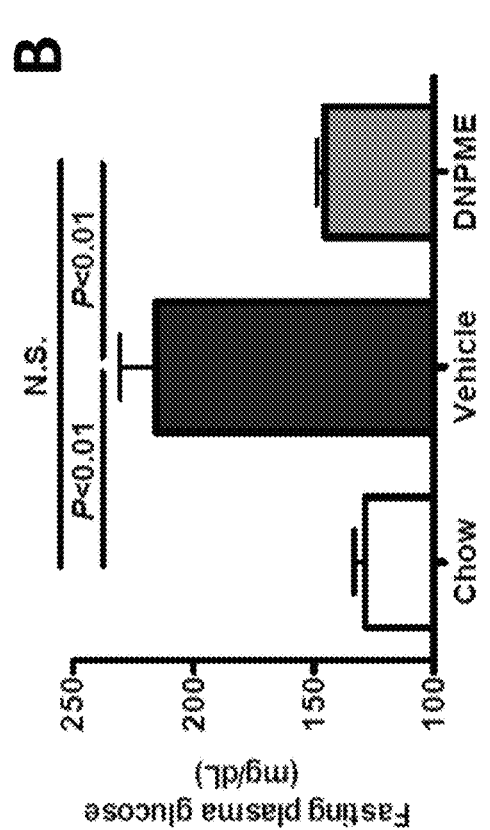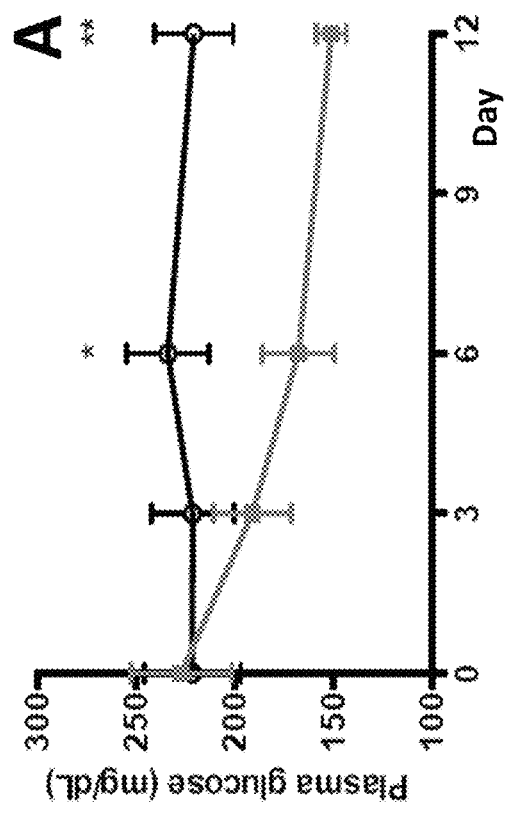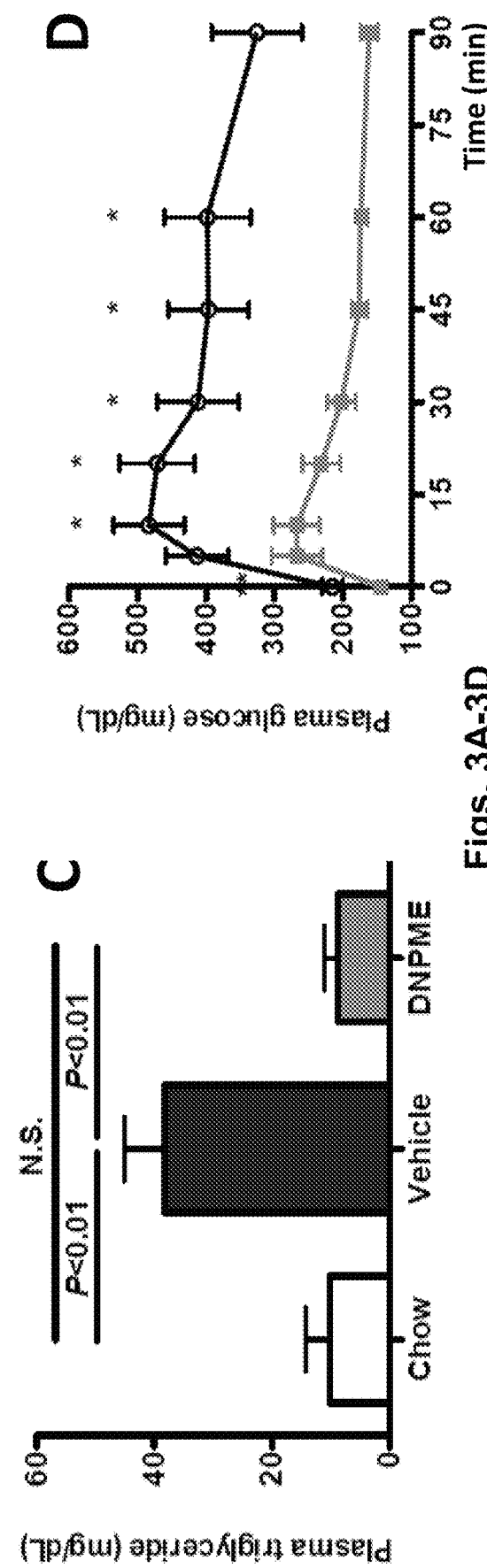
Figs. 3A-3D

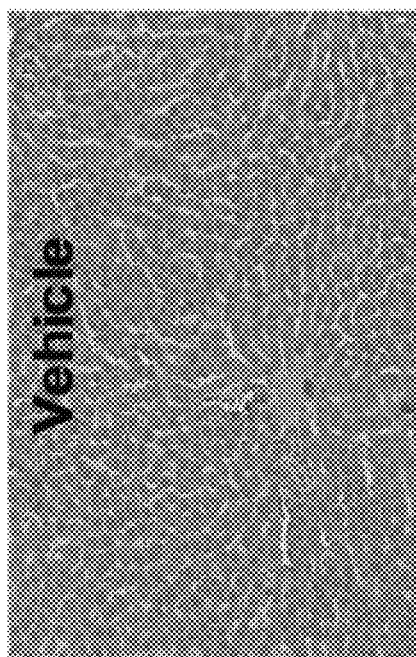 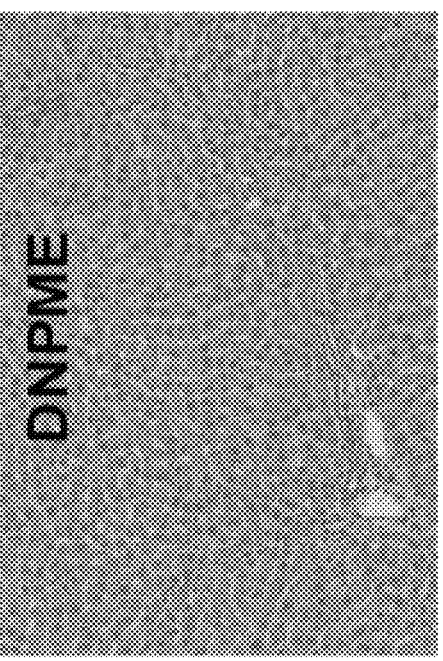
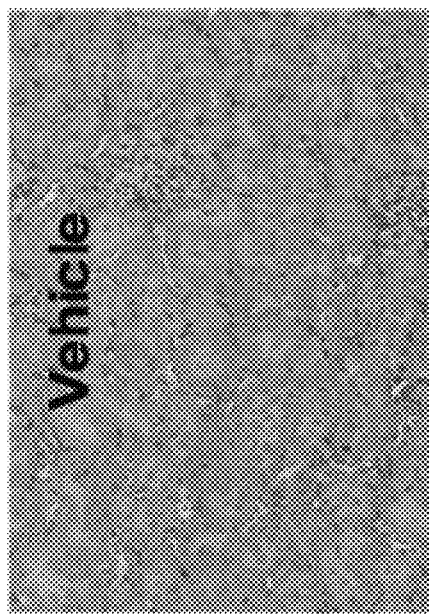 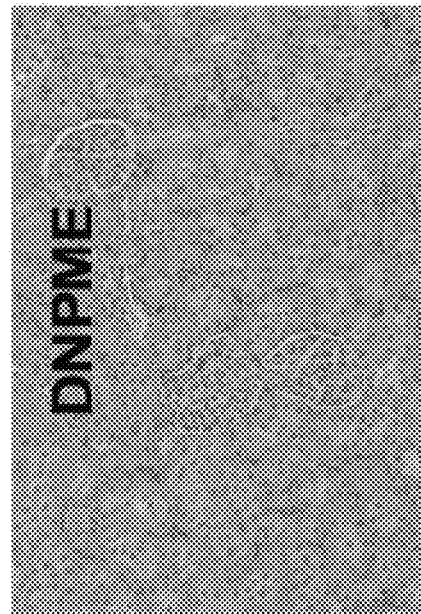
Figs. 5J-5K

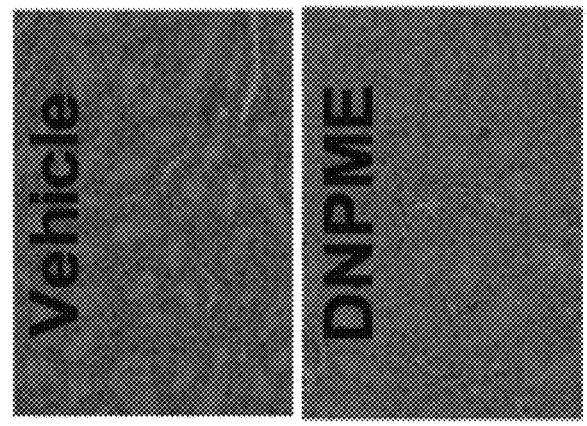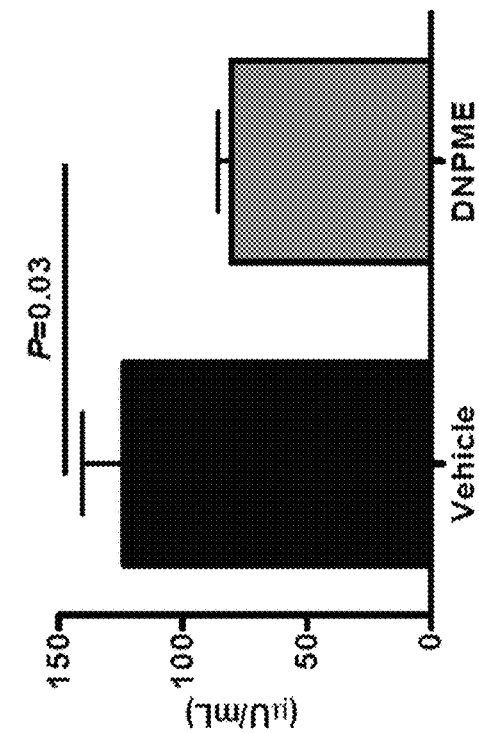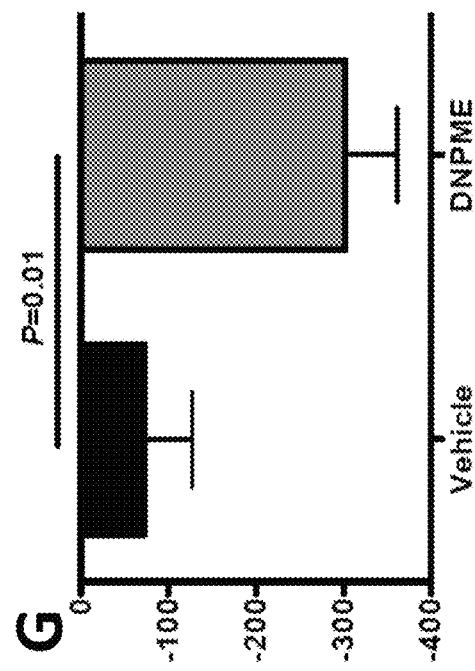
Figs. 7E-7H

| | Acetaminophen | DNPME |
|---|---|---|
| Lowest effective dose | 60 mg/kg | 5 mg/kg |
| LD50 | 800 mg/kg | 350 mg/kg |
| LD50/effective dose | 13 | 70 |

Fig. 27

THERAPEUTIC DNP DERIVATIVES AND METHODS USING SAME

CROSS-REFERENCE TO RELATED APPLICATIONS

The present application is a continuation of, and claims priority to, U.S. application Ser. No. 14/914,408, filed Feb. 25, 2016, which is a 35 U.S.C. § 371 national phase application from, and claims priority to, International Application No. PCT/US2014/053127, filed Aug. 28, 2014, and published under PCT Article 21(2) in English, which claims priority under 35 U.S.C. § 119(e) to U.S. Provisional Application No. 61/872,279, filed Aug. 30, 2013, all of which applications are incorporated herein by reference in their entireties.

STATEMENT REGARDING FEDERALLY SPONSORED RESEARCH OR DEVELOPMENT

This invention was made with government support under DK085638 and DK040936 awarded by National Institutes of Health. The government has certain rights in the invention.

BACKGROUND OF THE INVENTION

Non-alcoholic fatty liver disease (NAFLD) is a key factor in the pathogenesis of type 2 diabetes (T2D) and affects one in three Americans (Shulman, 2000, J. Clin. Invest. 106: 171-176; Petersen et al., 2005, Diabetes 54:603-608; Samuel & Shulman, 2012, Cell 148:852-857; Boyle et al., 2010, Popul. Health. Metr. 8:29). NAFLD is also a key predisposing factor for the development of non-alcoholic steatohepatitis (NASH), cirrhosis and hepatocellular carcinoma. Further, NAFLD-induced NASH may soon surpass hepatitis C and alcoholic cirrhosis as the most common indication for liver transplantation in the USA (Sanyal et al., 2010, Oncologist 15 Suppl. 4:14-22; Stickel & Hellerbrand, 2010, Gut 59:1303-1307; Barry et al., 2010, J. Hepatol. 56:1384-1391; White et al., 2012, Clin. Gastroenterol. Hepatol. 10:1342-1359). Thus, new and effective therapies for treatment of NAFLD are urgently needed.

One of the best characterized mitochondrial uncoupling agents is 2,4-dinitrophenol (DNP), a protonophore that shuttles protons across the mitochondrial membrane, dissipating the mitochondrial proton gradient and promoting heat dissipation of the energy derived from mitochondrial substrate oxidation. DNP was extensively used as a weight loss remedy in the 1930s but taken off the market by the U.S. Food and Drug Administration in 1938 due to the occurrence of fatal hyperthermia (Tainter et al., 1934, Am. J. Public Health Nations Health 24:1045-1053).

There is a need in the art for compositions useful for the treatment of NAFLD and other diseases and disorders. The present invention addresses this unmet need.

BRIEF SUMMARY OF THE INVENTION

The invention includes a compound of formula (I), or a salt, solvate, N-oxide thereof:

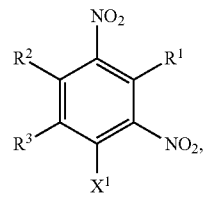

(I)

wherein in (I):

$R^1$, $R^2$ and $R^3$ are each independently selected from the group consisting of H, —$C_1$-$C_6$ alkyl, —$C_3$-$C_6$ cycloalkyl, —$C_1$-$C_6$ alkenyl, —$C_1$-$C_6$ fluoroalkyl, —$C_1$-$C_6$ heteroalkyl, —F, —Cl, —Br, —I, —CN, —$NO_2$, —$R^6$, —$OR^6$, —$SR^6$, —S(=O)$R^6$, —S(=O)$_2R^6$, —NHS(=O)$_2R^6$, —C(=O)$R^6$, —OC(=O)$R^6$, —C(=O)$OR^6$, —OC(=O)$OR^6$, —CH($R^6$)$_2$, —N($R^6$)$_2$, —C(=O)N($R^6$)$_2$, —OC(=O)N($R^6$)$_2$, —NHC(=O)NH($R^6$), —NHC(=O)$R^6$, —NHC(=O)$OR^6$, —C(OH)($R^6$)$_2$, —C($NH_2$)($R^6$)$_2$, and —(CH$_2$)$_m$$X^2$, wherein the alkyl, cycloalkyl and alkenyl groups are independently optionally substituted;

each occurrence of $R^4$ is independently selected from the group consisting of H, —$C_1$-$C_6$ alkyl, —($C_6$-$C_{10}$)aryl, —$C_1$-$C_3$ alkyl-($C_6$-$C_{10}$ aryl), —$C_3$-$C_6$ cycloalkyl, —$C_1$-$C_3$ alkyl-($C_3$-$C_6$ cycloalkyl), —($C_5$-$C_{10}$)heteroaryl, —$C_1$-$C_3$ alkyl-($C_5$-$C_{10}$ heteroaryl), —$C_1$-$C_6$ alkenyl, —$C_1$-$C_6$ fluoroalkyl, —$C_1$-$C_6$ heteroalkyl, —S(=O)$R^6$, —S(=O)$_2R^6$, —NHS(=O)$_2R^6$, —C(=O)$R^6$, —C(=O)$OR^6$, —CH($R^6$)$_2$, —N($R^6$)$_2$, —C(=O)N($R^6$)$_2$, —NHC(=O)NH($R^6$), —NHC(=O)$R^6$, —NHC(=O)$OR^6$, —C(OH)($R^6$)$_2$, —C($NH_2$)($R^6$)$_2$, —(CH$_2$)$_n$P(O)(OR$^6$)$_2$,

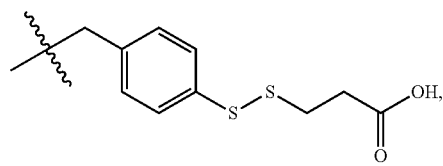

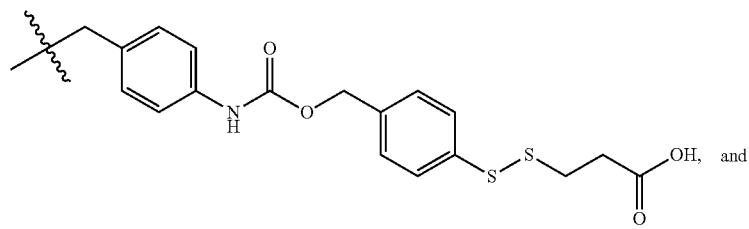

-continued

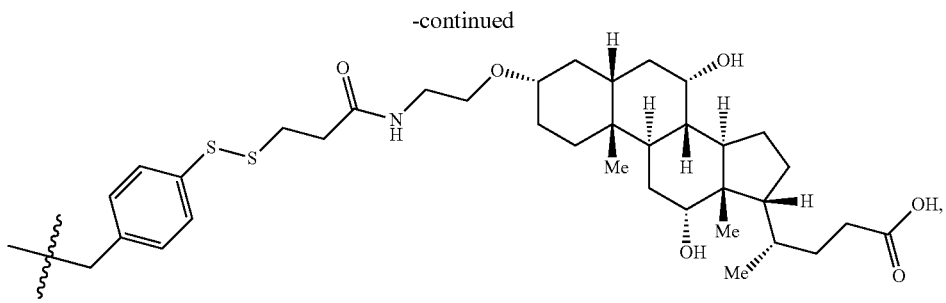

wherein the alkyl, aryl, cycloalkyl, heteroaryl and alkenyl groups are optionally substituted;

each occurrence of $R^5$ is each independently selected from the group consisting of H, —$C_1$-$C_6$ alkyl, —$C_1$-$C_3$ alkyl-($C_3$-$C_6$ cycloalkyl), —$C_1$-$C_3$ alkyl-($C_4$-$C_{10}$ heterocyclyl), —$C_1$-$C_3$ alkyl-($C_6$-$C_{10}$ aryl), —$C_1$-$C_3$ alkyl-($C_5$-$C_{10}$ heteroaryl), and —C(=O)$R^6$, wherein the alkyl, cycloalkyl, heterocyclyl, aryl, and heteroaryl groups are optionally substituted;

each occurrence of $R^6$ is independently selected from the group consisting of H and $C_1$-$C_6$ alkyl, wherein the alkyl groups are optionally substituted;

$X^1$ is $OR^4$, $B(OR^4)_2$, or $BR^4(OR^4)$;

$X^2$ is $N(R^5)_2$, $SR^5$, or $OR^5$;

m is an integer from 1-6; and n is an integer from 0-6, or any combinations thereof.

The invention further includes a pharmaceutical composition comprising a compound of the invention.

The invention further includes a method of preventing or treating a disease or disorder in a subject in need thereof.

The invention further includes a method of increasing energy expenditure in a subject in need thereof.

In certain embodiments, the method comprises administering to the subject a therapeutically effective amount of a compound of the invention.

In certain embodiments, the compound is not 2,4-dinitrophenol, 2,4-dinitrophenyl methyl ether, 2,4-dinitrophenyl boronic acid, 2,4-dinitrophenyl vinyl ether, 2,4-dinitrophenyl allyl ether, 2,4-dinitrophenyl isopropyl ether, 2,4-dinitrophenyl ethyl ether, 1-((4-methoxybenzyl)oxy)-2,4-dinitrobenzene, or (2,4-dinitrophenoxy)methyl dihydrogen phosphate.

In certain embodiments, the compound is not 2,4-dinitrophenol.

In certain embodiments, the compound is selected from the group consisting of N-(2-hydroxy-3,5-dinitrobenzyl)-4-mercaptobutanamide, 2-(1-hydroxypropyl)-4,6-dinitrophenol, 4-(2,4-dinitrophenoxy)pentan-2-ol, 3-(2,4-dinitrophenoxy) cyclohexanol, 2,4-dinitrophenyl dihydrogen phosphate, 3-((4-((2,4-dinitrophenoxy)methyl)phenyl)disulfanyl) propanoic acid, 3-((4-((((4-((2,4-dinitrophenoxy) methyl)phenyl)carbamoyl)oxy)methyl)phenyl) disulfanyl) propanoic acid, (R)-4-((3R,5R,7R,8R,9S,10S,12S,13R,14S,17S)-3-(2-(3-((4-((2,4-dinitrophenoxy)methyl)phenyl) disulfanyl)propanamido)ethoxy)-7,12-dihydroxy-10,13-dimethylhexadecahydro-1H-cyclopenta[a]phenanthren-17-yl)pentanoic acid, a salt, solvate, N-oxide thereof, and any combinations thereof.

In certain embodiments, the compound is at least one selected from the group consisting of: 2,4-dinitrophenyl methyl ether, 2,4-dinitrophenyl boronic acid, 2,4-dinitrophenyl vinyl ether, 2,4-dinitrophenyl allyl ether, 2,4-dinitrophenyl isopropyl ether, 2,4-dinitrophenyl ethyl ether, 1-((4-methoxybenzyl)oxy)-2,4-dinitrobenzene, N-(2-hydroxy-3,5-dinitrobenzyl)-4-mercaptobutanamide, 2-(1-hydroxypropyl)-4,6-dinitrophenol, 4-(2,4-dinitrophenoxy) pentan-2-ol, 3-(2,4-dinitrophenoxy)cyclohexanol, (2,4-dinitrophenoxy)methyl dihydrogen phosphate, 2,4-dinitrophenyl dihydrogen phosphate, 3-((4-((2,4-dinitrophenoxy)methyl)phenyl)disulfanyl) propanoic acid, 3-((4-((((4-((2,4-dinitrophenoxy)methyl)phenyl)carbamoyl)oxy)methyl)phenyl) disulfanyl)propanoic acid, (R)-4-((3R,5R,7R,8R,9S,10S,12S,13R,14S,17S)-3-(2-(3-((4-((2,4-dinitrophenoxy) methyl)phenyl)di sulfanyl)propanamido) ethoxy)-7,12-dihydroxy-10,13-dimethylhexadecahydro-1H-cyclopenta[a]phenanthren-17-yl)pentanoic acid, a salt, solvate, or N-oxide thereof, and any combinations thereof.

In certain embodiments, the composition further comprises at least one pharmaceutically acceptable carrier. In other embodiments, the composition further comprises at least one additional therapeutic agent.

In certain embodiments, the disease or disorder is at least one selected from the group consisting of non-alcoholic fatty liver disease (NAFLD), non-alcoholic steatohepatitis (NASH), hepatic steatosis, type 2 diabetes (T2D), acquired lipodystrophy, lipodystrophy (inherited), partial lipodystrophy, hypertriglyceridemia, obesity, metabolic syndrome, Rett's syndrome, metabolic syndrome associated with aging, metabolic diseases associated with increased reactive oxygen species (ROS), Friedreich's ataxia, and insulin resistance.

In certain embodiments, the subject is afflicted with at least one disease or disorder selected from the group consisting of non-alcoholic fatty liver disease (NAFLD), non-alcoholic steatohepatitis (NASH), hepatic steatosis, type 2 diabetes (T2D), acquired lipodystrophy, lipodystrophy (inherited), partial lipodystrophy, hypertriglyceridemia, obesity, metabolic syndrome, Rett's syndrome, metabolic syndrome associated with aging, metabolic diseases associated with increased reactive oxygen species (ROS), Friedreich's ataxia, and insulin resistance.

In certain embodiments, the therapeutically effective amount of the compound of formula (I) is about 25 μmoles/kg.

In certain embodiments, the subject is further administered at least one additional therapeutic agent. In other embodiments, the pharmaceutical composition and the at least one additional therapeutic agent are co-administered to the subject. In yet other embodiments, the pharmaceutical composition and the at least one additional therapeutic agent are co-formulated.

In certain embodiments, the subject is a mammal. In other embodiments, the mammal is human.

BRIEF DESCRIPTION OF THE DRAWINGS

The following detailed description of specific embodiments of the invention will be better understood when read in conjunction with the appended drawings. For the purpose of illustrating the invention, there are shown in the drawings specific embodiments. It should be understood, however, that the invention is not limited to the precise arrangements and instrumentalities of the embodiments shown in the drawings.

FIG. 1, comprising FIG. 1A is a graph illustrating rectal temperature following IP injection of DNP. FIG. 1I is a graph illustrating plasma creatinine after 5 days of daily treatment with DNPME or vehicle. FIG. 1J is a graph illustrating liver TAG. FIG. 1K is a graph illustrating ALT after 6 weeks of daily treatment in chow-fed rats. FIG. 1L is a graph illustrating AST after 6 weeks of daily treatment in chow-fed rats. FIG. 1N is a graph illustrating creatine after 6 weeks of daily treatment in chow-fed rats. Data are represented as mean±S.E.M. n=4-6 per dose.

FIG. 2, comprising FIG. 2A is a graph illustrating fasting plasma glucose. FIG. 2E is a graph illustrating plasma glucose during an intraperitoneal glucose tolerance test. FIG. 2F is a graph illustrating insulin during an intraperitoneal glucose tolerance test. For FIGS. 2E-2F: Black circles=vehicle treated, red/gray squares=DNPME treated. *$P<0.05$, $P<0.01$, *$P<0.001$. FIG. 2G is a graph illustrating the glucose infusion rate to maintain euglycemia during the hyperinsulinemic-euglycemic clamp. FIG. 2H is a graph illustrating insulin-stimulated glucose metabolism. FIG. 2O is a graph illustrating the effect of DNPME on hepatic flux through pyruvate carboxylase. For FIGS. 2N-2O: n=3 vehicle treated and 6 DNPME treated rats. Rats were fasted overnight (16 hours) prior to each of these studies in FIG. 2. Unless otherwise noted, n=5-8 per group for FIG. 2. Data are represented as mean±S.E.M.

FIG. 3, comprising FIGS. 3A-3G, illustrates the finding that DNPME reverses hyperglycemia, hypertriglyceridemia and hepatic steatosis in a rat model of type 2 diabetes and NAFLD. FIG. 3A is a graph illustrating random plasma glucose concentrations during DNPME treatment. FIG. 3B is a graph illustrating fasting plasma glucose concentrations. FIG. 3C is a graph illustrating fasting plasma triglyceride concentrations. FIG. 3D is a graph illustrating plasma glucose concentrations before and during an intraperitoneal glucose tolerance test. FIG. 3E is a graph illustrating plasma glucose and insulin concentrations before and during an intraperitoneal glucose tolerance test. FIG. 3F is a graph illustrating liver triglyceride content. FIG. 3G is a graph illustrating quadriceps triglyceride content. n=4-7 per group. Data are represented as mean±S.E.M.

FIG. 4, comprising FIG. 4A is a graph illustrating plasma DNP and DNPME concentration after an intraperitoneal injection of DNPME (5 mg/kg). FIG. 4B is a graph illustrating liver DNP and DNPME concentration after an injection of DNPME (5 mg/kg). For FIGS. 4A-4B: red/dark gray squares=DNPME, blue/light gray circles=DNP. FIG. 4C is a graph illustrating tissue concentration of DNP after an injection of DNPME (5 mg/kg). FIG. 4D is a graph illustrating tissue concentration of DNPME after an injection of DNPME (5 mg/kg). FIG. 4E is a graph illustrating tissue concentration of DNP one hour after an injection of DNP (5 mg/kg). FIG. 4F is a graph illustrating plasma DNP concentration after an injection of DNP (25 mg/kg, blue circles) or DNPME (5 mg/kg, red squares). Each time point represents an individual animal. FIG. 4G is a graph illustrating plasma and tissue concentrations of DNP after injection of DNP (25 mg/kg). Tissues were isolated 1 hour after DNP injection. FIG. 4H is a graph illustrating DNP concentration in tissues after 7 days of daily DNPME injections. FIG. 4I is a graph illustrating DNPME concentration in tissues after 7 days of daily DNPME injections. Unless otherwise noted, n=4 per group. Data are expressed as mean±S.E.M FIG. 5, comprising FIGS. 5A-5K, illustrates the screening of liver-targeted DNP compounds. FIG. 5A illustrates the structures of compounds useful in the invention. FIG. 5B is a graph illustrating basal oxygen consumption rate in plated hepatocytes, then oxygen consumption rate with addition of the compounds of FIG. 5A at increasing doses. FIG. 5C is a graph illustrating ALT in rats treated for 5 days with DNP or vehicle. FIG. 5D is a graph illustrating AST in rats treated for 5 days with DNP or vehicle. FIG. 5E is a graph illustrating BUN in rats treated for 5 days with DNP or vehicle. FIG. 5F is a graph illustrating creatine in rats treated for 5 days with DNP or vehicle. FIG. 5G is a graph illustrating hepatic TAG in rats treated for 5 days with DNP or vehicle. For FIGS. 5C-5G, *$P<0.05$, $P<0.01$, *$P<0.001$. FIG. 5H is a graph illustrating rectal temperature in rats treated for 6 weeks with DNPME or vehicle (red/light gray squares=DNPME, black circles=vehicle). FIG. 5I is a graph illustrating 24 hour urine creatinine clearance in rats treated for 6 weeks with DNPME or vehicle. FIG. 5J is a representative image illustrating liver stained with hematoxylin & eosin. FIG. 5K is a representative image illustrating kidney stained with hematoxylin & eosin. Data are mean±SEM.

FIG. 6, comprising FIG. 6A is a graph illustrating body weight at the time of clamp. FIG. 6T is a graph illustrating minimal changes in markers of inflammation following DNPME treatment. Unless otherwise noted, n=5-8 per group. *P<0.05, **P<0.01. Data are mean±S.E.M.

FIG. 7, comprising FIG. 7A is a graph illustrating body weight in an intraperitoneal glucose tolerance test. FIG. 7E is a graph illustrating liver histology in T2D rats. FIG. 7F is a graph illustrating renal histology in T2D rats. FIG. 7G is a graph illustrating fasting plasma glucose in Zucker Diabetic Fatty rats. FIG. 7H is a graph illustrating fasting plasma insulin in Zucker Diabetic Fatty rats. FIG. 7O is a graph illustrating creatine in Zucker Diabetic Fatty rats. n=6-8 per group. Data are presented as mean±S.E.M.

FIG. 8, comprising FIG. 8A is a graph illustrating oxygen consumption. FIG. 8R is a graph illustrating liver AMPK phosphorylation relative to total AMPK, and ACC phosphorylation relative to total ACC. For FIGS. 8G-8R, n=4-7 per group. Data are shown as mean±S.E.M.

FIG. 27 is a table illustrating the LD$_{50}$ dose/effective dose comparison of DNPME to acetaminophen.

DETAILED DESCRIPTION OF THE INVENTION

Figures 1A, 1B, 1C, 1D:
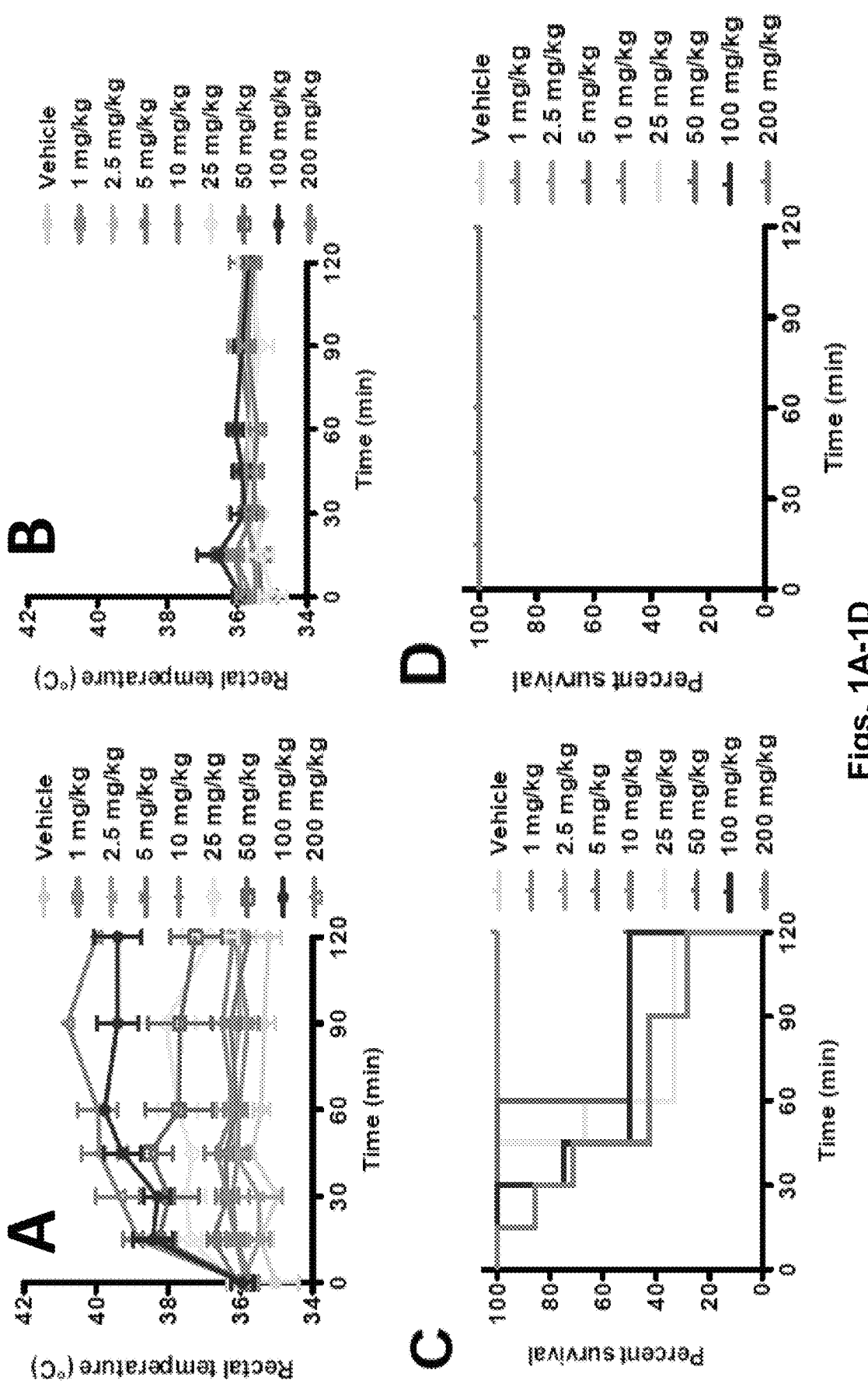
FIGS. 1A-1N, illustrates the safety and efficacy profile of DNPME compared to DNP.
FIG. 1B is a graph illustrating rectal temperature following IP injection of DNPME.
FIG. 1C is a graph illustrating survival acutely following treatment with DNP.
FIG. 1D is a graph illustrating survival acutely following treatment with DNPME.

The present invention relates to the unexpected discovery that derivatives of 2,4-dinitrophenol (DNP) promote increased mitochondrial activity, but do not cause hypothermia and other systemic toxicities associated with DNP. In one aspect, the invention provides a novel method of treating diseases or disorders in a subject in need thereof. In certain embodiments, the disease or disorder is selected from the group consisting of non-alcoholic fatty liver disease (NAFLD), non-alcoholic steatohepatitis (NASH), hepatic steatosis, type 2 diabetes (T2D), acquired lipodystrophy, lipodystrophy (inherited), partial lipodystrophy, hypertriglyceridemia, obesity, metabolic syndrome, Rett's syndrome, metabolic syndrome associated with aging, metabolic diseases associated with increased reactive oxygen species (ROS), Friedreich's ataxia, and insulin resistance. In other embodiments, the method comprises administering to the subject in need thereof a therapeutically effective amount of at least one of the DNP derivatives of the invention.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, ±5%, ±1%, or ±0.1% from the specified value, as such variations are appropriate to perform the disclosed methods.

The term "abnormal," when used in the context of organisms, tissues, cells or components thereof, refers to those organisms, tissues, cells or components thereof that differ in at least one observable or detectable characteristic (e.g., age, treatment, time of day, and the like) from those organisms, tissues, cells or components thereof that display the "normal" (expected) respective characteristic. Characteristics that are normal or expected for one cell or tissue type might be abnormal for a different cell or tissue type.

A disease or disorder is "alleviated" if the severity of a symptom of the disease or disorder, the frequency with which such a symptom is experienced by a patient, or both, is reduced.

A "disease" is a state of health of an animal wherein the animal cannot maintain homeostasis, and wherein if the disease is not ameliorated then the animal's health continues to deteriorate.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, nasal, inhalational, topical, oral, aerosol, buccal, sublingual, rectal, pleural, parenteral, peritoneal, vaginal, intramuscular, subcutaneous, transdermal, epidural, intratracheal, otic, intraocular, ophthalmic, intrathecal and intravenous administration.

As used herein, the term "derivative" refers to a small molecule that differs in structure from the reference molecule (i.e., has a distinct structure from the reference molecule), but retains the essential properties of the reference molecule. A derivative may change its interaction with certain other molecules relative to the reference molecule. A derivative molecule may also include a salt, an adduct, or other variant of the reference molecule.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "DNP" and "2,4-DNP" interchangeably refer to 2,4-dinitrophenol, a salt, solvate or adduct thereof.

An "effective amount" of a delivery vehicle is that amount sufficient to effectively bind or deliver a compound.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "efficacy" refers to the maximal effect ($E_{max}$) achieved within an assay.

As used herein, the term "metabolic disorder" refers to a condition characterized by an alteration or disturbance in metabolic function. "Metabolic" and "metabolism" are terms well known in the art and generally include the whole range of biochemical processes that occur within a living organism.

The terms "patient" and "subject" and "individual" are used interchangeably herein, and refer to any animal, or cells thereof whether in vitro or in situ, amenable to the methods described herein. In certain non-limiting embodiments, the patient, subject or individual is a human.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxy benzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluene sulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the invention include, for example, ammonium salts and metallic salts, including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "potency" refers to the dose needed to produce half the maximal response ($ED_{50}$).

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$)alkyl, particularly ethyl, methyl, isopropyl, isobutyl, n-pentyl, n-hexyl and cyclopropylmethyl.

As used herein, the term "substituted alkyl" means alkyl as defined above, substituted by one, two or three substituents selected from the group consisting of halogen, —OH, alkoxy, —$NH_2$, —$N(CH_3)_2$, —C(=O)OH, trifluoromethyl, —C≡N, —C(=O)O($C_1$-$C_4$)alkyl, —C(=O)$NH_2$, —$SO_2NH_2$, —C(=NH)$NH_2$, and —$NO_2$, preferably containing one or two substituents selected from halogen, —OH, alkoxy, —$NH_2$, trifluoromethyl, —$N(CH_3)_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—SS—CH$_3$ As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are (C$_1$-C$_3$) alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" refers to a mono cyclic or polycyclic non-aromatic radical, wherein each of the atoms forming the ring (i.e. skeletal atoms) is a carbon atom. In certain embodiments, the cycloalkyl group is saturated or partially unsaturated. In other embodiments, the cycloalkyl group is fused with an aromatic ring. Cycloalkyl groups include groups having from 3 to 10 ring atoms. Illustrative examples of cycloalkyl groups include, but are not limi-ted to, the following moieties:

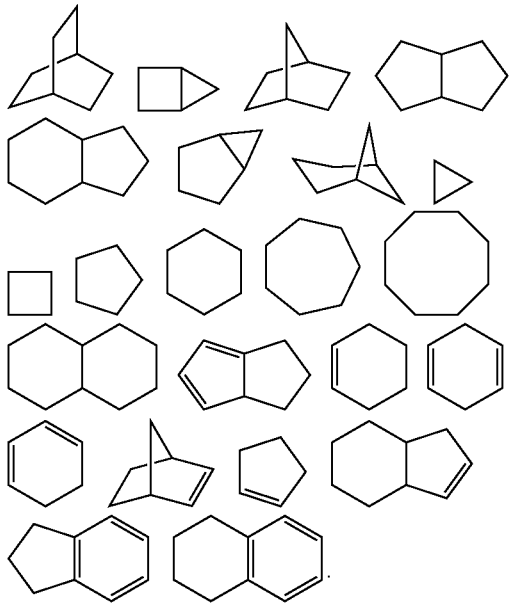

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S and N. In certain embodiments, each heterocycloalkyl group has from 4 to 10 atoms in its ring system, with the proviso that the ring of said group does not contain two adjacent O or S atoms. In other embodiments, the heterocycloalkyl group is fused with an aromatic ring. In certain embodiments, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

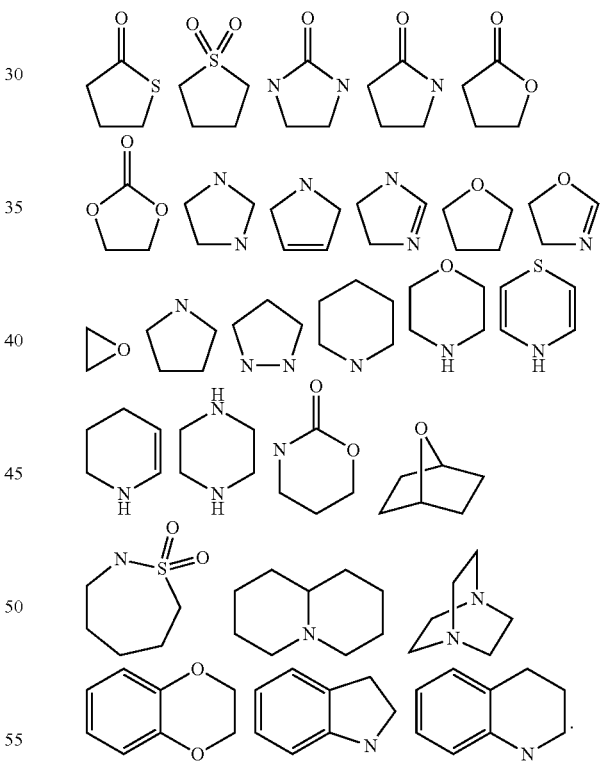

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e. having (4n+2) delocalized π(pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. Preferred examples are phenyl and naphthyl, most preferred is phenyl.

As used herein, the term "aryl-($C_1$-$C_3$)alkyl" means a functional group wherein a one- to three-carbon alkylene chain is attached to an aryl group, e.g., —$CH_2CH_2$-phenyl. Preferred is aryl-$CH_2$— and aryl-$CH(CH_3)$—. The term "substituted aryl-($C_1$-$C_3$)alkyl" means an aryl-($C_1$-$C_3$)alkyl functional group in which the aryl group is substituted. Preferred is substituted aryl($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$)alkyl" means a heteroaryl-($C_1$-$C_3$)alkyl functional group in which the heteroaryl group is substituted. Preferred is substituted heteroaryl-($CH_2$)—.

As used herein, the term "heteroaryl" or "heteroaromatic" refers to a heterocycle having aromatic character. A polycyclic heteroaryl may include one or more rings that are partially saturated. Examples include the following moieties:

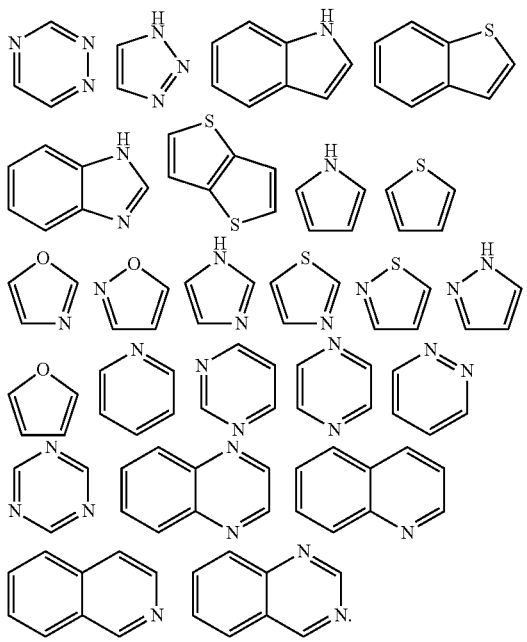

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet other embodiments, the substituents vary in number between one and two.

As used herein, the term "optionally substituted" means that the referenced group may be substituted or unsubstituted. In certain embodiments, the referenced group is optionally substituted with zero substituents, i.e., the referenced group is unsubstituted. In other embodiments, the referenced group is optionally substituted with one or more additional group(s) individually and independently selected from groups described herein.

In certain embodiments, the substituents are independently selected from the group consisting of oxo, halogen, —CN, —$NH_2$, —OH, —$NH(CH_3)$, —$N(CH_3)_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$alkyl, —C(=O)NH[substituted or unsubstituted alkyl, or substituted or unsubstituted phenyl], —C(=O)N[H or alkyl]$_2$, —OC(=O)N[substituted or unsubstituted alkyl]$_2$, —NHC(=O)NH [substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]$_2$, and —C(NH$_2$)[substituted or unsubstituted alkyl]$_2$. In other embodiments, by way of example, an optional substituent is selected from oxo, fluorine, chlorine, bromine, iodine, —CN, —$NH_2$, —OH, —SH, —$NH(CH_3)$, —$N(CH_3)_2$, —$CH_3$, —$CH_2CH_3$, —$CH(CH_3)_2$, —$CF_3$, —$CH_2CF_3$, —$OCH_3$, —$OCH_2CH_3$, —$OCH(CH_3)_2$, —$OCF_3$, —$OCH_2CF_3$, —S(=O)$_2$—$CH_3$, —C(=O)$NH_2$, —C(=O)—$NHCH_3$, —$NHC(=O)NHCH_3$, —C(=O)$CH_3$, and —C(=O)OH. In yet other embodiments, the substituents are independently selected from the group consisting of $C_{1-6}$ alkyl, —OH, $C_{1-6}$ alkoxy, halo, amino, acetamido, oxo and nitro. In yet other embodiments, the substituents are independently selected from the group consisting of $C_{1-6}$ alkyl, $C_{1-6}$ alkoxy, halo, acetamido, and nitro. As used herein, where a substituent is an alkyl or alkoxy group, the carbon chain may be branched, straight or cyclic, with straight being preferred.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to the unexpected discovery that derivatives of 2,4-dinitrophenol (DNP) promote increased mitochondrial activity, but do not cause hypothermia and other systemic toxicities associated with DNP.

The compounds related to DNP derivatives of the invention may be used to treat a disease or disorder such as, but not limited to, non-alcoholic fatty liver disease (NAFLD), non-alcoholic steatohepatitis (NASH), hepatic steatosis, type 2 diabetes (T2D), acquired lipodystrophy, lipodystrophy (inherited), partial lipodystrophy, hypertriglyceridemia, obesity, metabolic syndrome, Rett's syndrome, metabolic syndrome associated with aging, metabolic diseases associated with increased reactive oxygen species (ROS), Friedreich's ataxia, and/or insulin resistance.

In one aspect, the present invention relates to the discovery that administering a liver-targeting mitochondrial uncoupling agent, such as a compound of the invention, to a subject promotes increased energy expenditure in a safe and tolerable manner. There are currently no drugs that promote increased energy expenditure in a safe and tolerable manner. Thus, the compounds of the invention represent a safe and novel class of agents for the treatment of mitochondrial-related diseases and/or disorders.

In one aspect, the present invention provides compounds, and compositions comprising the same, that target the liver. In another aspect, hyperthermia and related toxicities of DNP are on-target effects related to systemic mitochondrial uncoupling, and thus a compound of the invention targeting the liver is an effective and safe approach for the treatment of diseases and disorders because the compound promotes the metabolism of hepatic triglyceride, while avoiding hyperthermia and associated systemic toxicities that typically occur with mitochondrial uncoupling agents.

Diseases or Disorders

The methods, compounds and compositions of the invention are useful for treating and/or preventing a variety of diseases or disorders. In certain embodiments, the disease or disorder is a metabolic disease or disorder. Non-limiting examples of metabolic diseases or disorders include, but are not limited to, hyperglycemia, prediabetes, diabetes (type I and type 2), obesity, NAFLD, insulin resistance, Type 2 Diabetes (T2D), metabolic syndrome and dyslipidemia related to metabolic conditions.

In certain embodiments, the compounds, compositions and methods of the invention may be used to treat or prevent a disease or disorder such as, but not limited to, NAFLD, non-alcoholic steatohepatitis (NASH), hepatic steatosis, acquired lipodystrophy, inherited lipodystrophy, partial lipodystrophy, insulin resistance, Type 2 Diabetes (T2D), obesity, hypertriglyceridemia, metabolic syndrome, metabolic syndrome associated with aging, metabolic diseases associated with increased reactive oxygen species (ROS), Friedreich's ataxia, diseases in which free radical mediated oxidative injury leads to tissue degeneration, and/or diseases in which cells inappropriately undergo apoptosis, and include the treatment of a wide number of diseases, including but not limited to auto-immune disease, congenital muscular dystrophy, fatal infantile myopathy, "later-onset" myopathy, MELAS (mitochondrial encephalopathy, lactic acidosis, and stroke), MIDD (mitochondrial diabetes and deafness), MERRF (myoclonic epilepsy ragged red fiber syndrome), arthritis, NARP (Neuropathy; Ataxia; Retinitis Pigmentosa), MNGIE (Myopathy and external ophthalmoplegia; Neuropathy; Gastro-Intestinal; Encephalopathy), LHON (Leber's; Hereditary; Optic; Neuropathy), Kearns-Sayre disease, Pearson's Syndrome, PEO (Progressive External Ophthalmoplegia), Wolfram syndrome, DIDMOAD (Diabetes Insipidus, Diabetes Mellitus, Optic Atrophy, Deafness), ADPD (Alzheimer's disease; Parkinson's disease), AMFD (ataxia, myoclonus and deafness), CIPO (chronic intestinal pseudoobstruction; myopathy; opthalmoplegia), CPEO (chronic progressive external opthalmoplegia), maternally inherited deafness, aminoglycoside-induced deafness, DEMCHO (dementia; chorea), DMDF (diabetes mellitus; deafness), exercise intolerance, ESOC (epilepsy; strokes; optic atrophy; congenitive decline), FBSN (familial bilateral striatal necrosis), FICP (fatal infantile cardiomyopathy plus a MELAS-associated cardiomyopathy), GER (gastrointestinal reflux), LIMM (lethal infantile mitochondrial myopathy), LDYT (Leber's hereditary optic neuropathy and DYsTonia), MDM (myopathy; diabetes mellitus), MEPR (myoclonic epilepsy; psychomotor regression), MERME (MERRF/MELAS overlap disease), MHCM (maternally inherited hypertrophic cardiomyopathy), MICM (maternally inherited cardiomyopathy), MILS (maternally inherited Leigh syndrome), mitochondrial encephalocardiomyopathy, mitochondrial encephalomyopathy, mitochondrial myopathy, MMC (maternal myopathy; cardio myopathy), multi-system mitochondrial disorder (myopathy; encephalopathy; blindness; hearing loss; peripheral neuropathy), NIDDM (non-insulin dependent diabetes mellitus), PEM (progressive encephalopathy), PME (progressive myclonus epilepsy), Rett's syndrome, SIDS (sudden infant death syndrome, SNHL (sensorineural hearing loss), Leigh's Syndrome, dystonia, schizophrenia, and/or psoriasis.

In certain embodiments, the disease or disorder comprises NAFLD. In other embodiments, the disease or disorder comprises non-alcoholic steatohepatitis (NASH). In yet other embodiments, the disease or disorder comprises hepatic steatosis. In yet other embodiments, the disease or disorder comprises Type 2 Diabetes. In yet other embodiments, the disease or disorder comprises acquired lipodystrophy. In yet other embodiments, the disease or disorder comprises inherited lipodystrophy. In yet other embodiments, the disease or disorder comprises partial lipodystrophy. In yet other embodiments, the disease or disorder comprises hypertriglyceridemia. In yet other embodiments, the disease or disorder comprises obesity. In yet other embodiments, the disease or disorder comprises metabolic syndrome. In yet other embodiments, the disease or disorder comprises insulin resistance. In yet other embodiments, the disease or disorder comprises Rett's syndrome. In yet other embodiments, the disease or disorder comprises metabolic syndrome associated with aging. In yet other embodiments, the disease or disorder comprises metabolic diseases associated with increased reactive oxygen species (ROS). In yet other embodiments, the disease or disorder comprises Friedreich's ataxia.

Compounds

The compounds of the invention may be synthesized using techniques disclosed herein as well as techniques well-known in the art of organic synthesis. The starting materials and intermediates required for the synthesis may be obtained from commercial sources or synthesized according to methods known to those skilled in the art.

In one aspect, the compound of the invention is a targeting mitochondrial uncoupling agent. In certain embodiments, the compound is a liver-targeting mitochondrial uncoupling agent. In other embodiments, the compounds of the invention represent a safe and novel class of agents for the treatment of mitochondrial-related diseases and disorders because the compounds are not systemically toxic.

In one aspect, the compound of the invention is a compound of formula (I), or a salt, solvate, or N-oxide thereof:

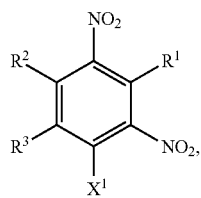

(I)

wherein in (I):

$R^1$, $R^2$ and $R^3$ are each independently selected from the group consisting of H, —$C_1$-$C_6$ alkyl, —$C_3$-$C_6$ cycloalkyl, —$C_1$-$C_6$ alkenyl, —$C_1$-$C_6$ fluoroalkyl, —$C_1$-$C_6$ heteroalkyl, —F, —Cl, —Br, —I, —CN, —$NO_2$, —$R^6$, —$OR^6$, —$SR^6$, —S(=O)$R^6$, —S(=O)$_2R^6$, —NHS(=O)$_2R^6$, —C(=O)$R^6$, —OC(=O)$R^6$, —C(=O)O$R^6$, —OC(=O)O$R^6$, —CH($R^6$)$_2$, —N($R^6$)$_2$, —C(=O)N($R^6$)$_2$, —OC(=O)N($R^6$)$_2$, —NHC(=O)NH($R^6$), —NHC(=O)$R^6$, —NHC(=O)O$R^6$, —C(OH)($R^6$)$_2$, —C($NH_2$)($R^6$)$_2$, and —($CH_2$)$_mX^2$, wherein the alkyl, cycloalkyl and alkenyl groups are independently optionally substituted;

each occurrence of $R^4$ is independently selected from the group consisting of H, —$C_1$-$C_6$ alkyl, —($C_6$-$C_{10}$)aryl, —$C_1$-$C_3$ alkyl-($C_6$-$C_{10}$ aryl), —$C_3$-$C_6$ cycloalkyl, —$C_1$-$C_3$ alkyl-($C_3$-$C_6$ cycloalkyl), —($C_5$-$C_{10}$)heteroaryl, —$C_1$-$C_3$ alkyl-($C_5$-$C_{10}$ heteroaryl), —$C_1$-$C_6$ alkenyl, —$C_1$-$C_6$ fluoroalkyl, —$C_1$-$C_6$ heteroalkyl, —$R^6$, —S(=O)$R^6$, —S(=O)$_2R^6$, —NHS(=O)$_2R^6$, —C(=O)$R^6$, —C(=O)O$R^6$, —CH($R^6$)$_2$, —N($R^6$)$_2$, —C(=O)N($R^6$)$_2$, —NHC(=O)NH($R^6$), —NHC(=O)$R^6$, —NHC(=O)O$R^6$, —C(OH)($R^6$)$_2$, —C($NH_2$)($R^6$)$_2$, —($CH_2$)$_nP(O)(OR^6)_2$,

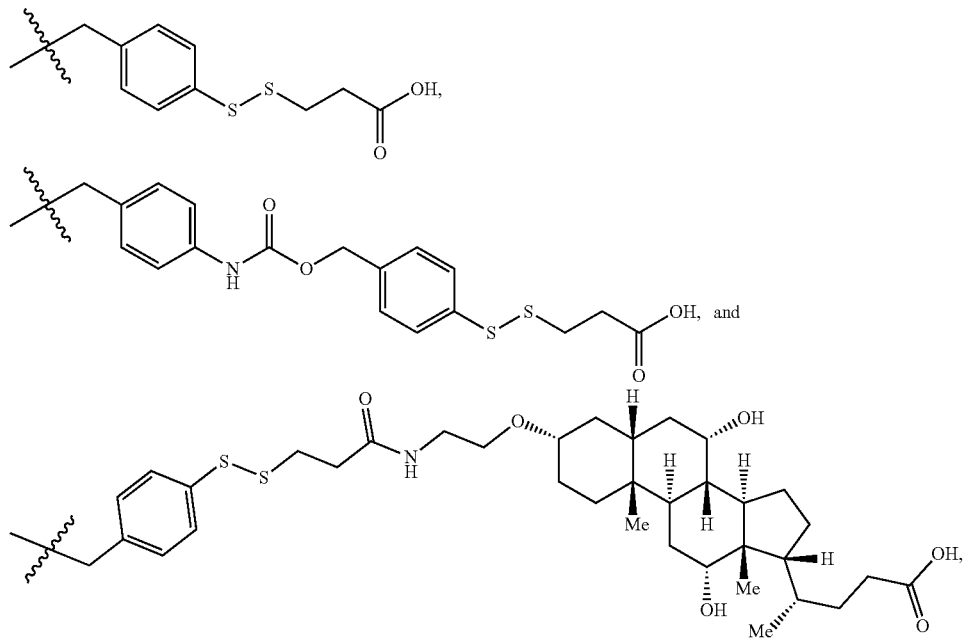

wherein the alkyl, aryl, cycloalkyl, heteroaryl and alkenyl groups are optionally substituted;

each occurrence of $R^5$ is each independently selected from the group consisting of H, —$C_1$-$C_6$ alkyl, —$C_1$-$C_3$ alkyl-($C_3$-$C_6$ cycloalkyl), —$C_1$-$C_3$ alkyl-($C_4$-$C_{10}$ heterocyclyl), —$C_1$-$C_3$ alkyl-($C_6$-$C_{10}$ aryl), —$C_1$-$C_3$ alkyl-($C_5$-$C_{10}$ heteroaryl), and —C(=O)$R^6$, wherein the alkyl, cycloalkyl, heterocyclyl, aryl, and heteroaryl groups are optionally substituted;

each occurrence of $R^6$ is independently selected from the group consisting of H and $C_1$-$C_6$ alkyl, wherein the alkyl groups are optionally substituted;

$X^1$ is $OR^4$, $B(OR^4)_2$, or $BR^4(OR^4)$;

$X^2$ is $N(R^5)_2$, $SR^5$, or $OR^5$;

m is an integer from 1-6; and n is an integer from 0-6, with the proviso that the compound is not 2,4-dinitrophenol.

In certain embodiments, the compound of the invention is selected from the group consisting of: 2,4-dinitrophenyl methyl ether, 2,4-dinitrophenyl boronic acid, 2,4-dinitrophenyl vinyl ether, 2,4-dinitrophenyl allyl ether, 2,4-dinitrophenyl isopropyl ether, 2,4-dinitrophenyl ethyl ether, 1-((4-methoxybenzyl)oxy)-2,4-dinitrobenzene, N-(2-hydroxy-3,5-dinitrobenzyl)-4-mercaptobutanamide, 2-(1- hydroxypropyl)-4,6-dinitrophenol, 4-(2,4-dinitrophenoxy) pentan-2-ol, 3-(2,4-dinitrophenoxy)cyclohexanol, (2,4-dinitrophenoxy)methyl dihydrogen phosphate, 2,4-dinitrophenyl dihydrogen phosphate, 3-((4-((2,4-dinitrophenoxy)methyl)phenyl)disulfanyl) propanoic acid, 3-((4-((((4-((2,4-dinitrophenoxy)methyl)phenyl)carbamoyl)oxy)methyl)phenyl) disulfanyl)propanoic acid, (R)-4-((3R,5R,7R,8R,9S,10S,12S,13R,14S,17S)-3-(2-(3-((4-((2,4-dinitrophenoxy) methyl)phenyl)di sulfanyl)propanamido)ethoxy)-7,12-dihydroxy-10,13-dimethylhexadecahydro-1H-cyclopenta[a]phenanthren-17-yl)pentanoic acid, a salt, solvate, or N-oxide thereof, and any combinations thereof.

The present invention also contemplates phosphate ester and dioxaphosphorinane prodrugs. For general examples of phosphate ester prodrugs, see Heimbach et al., 2003, Int. J. Pharm. 261:81-92, which is incorporated herein by reference in its entirety. For examples of anti-HIV molecules, see Nowicka-Sans et al., 2012, Antimicrob. Agents Chemother. 56:3498-3507 and Kadow et al., 2012, J. Med. Chem. 55:2048-2056, each of which is incorporated herein by reference in its entirety. The anti-HIV prodrugs are thought to be cleaved by alkaline phosphatase (ALP) located on the luminal surface of the mall intestine. ALPs are present throughout the body (especially in the intestine), so premature cleavage of DNP after the intestinal absorption may be problematic. For examples of phosphate ester and dioxaphosphorinane prodrugs, see Erion et al., 2005, J. Pharmacol. Exp. Ther. 312:554-560, which is incorporated herein by reference in its entirety.

In certain embodiments, the compound of the invention is a targeted mitochondrial uncoupling agent. In yet other embodiments, the compound of the invention is a compound of formula (I). In yet other embodiments, the compound of the invention is a DNP derivative.

In one aspect, the present invention includes compositions comprising at least one compound of the invention. In other embodiments, the compound of the invention is a compound of formula (I). In yet other embodiments, the compound of the invention is a DNP derivative. The present invention also includes a composition comprising at least one compound of the invention, wherein the composition optionally further comprise at least one additional therapeutic agent. The invention also includes a pharmaceutical composition comprising at least one compound of the invention and at least one pharmaceutically acceptable carrier.

Synthesis

Compounds of formula (I) may be prepared by the general schemes described herein, using the synthetic method known by those skilled in the art. The following examples illustrate non-limiting embodiments of the invention.

The compounds of the invention may possess one or more stereocenters, and each stereocenter may exist independently in either the (R) or (S) configuration. In certain embodiments, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compounds of the invention may exist as tautomers. All tautomers are included within the scope of the compounds presented herein.

In certain embodiments, compounds described herein are prepared as prodrugs. A "prodrug" refers to an agent that is converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the invention are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In certain embodiments, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In other embodiments, each protective group is removable by a different means. Protective groups that are cleaved under totally disparate reaction conditions fulfill the requirement of differential removal.

In certain embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In certain embodiments, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxy benzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

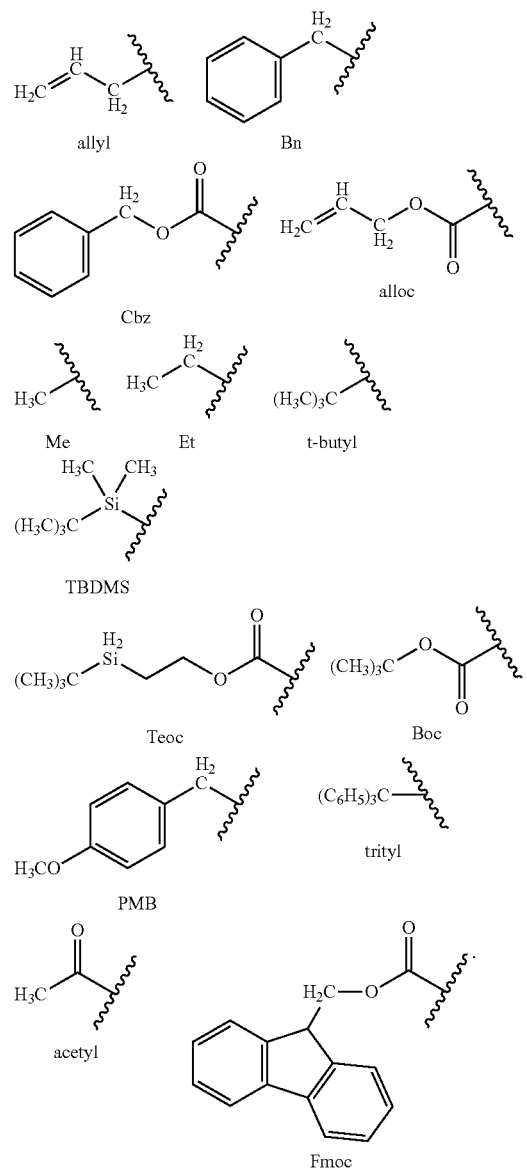

Other protecting groups, plus a detailed description of techniques applicable to the creation of protecting groups and their removal are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Methods

The invention includes a method of treating or preventing a disease or disorder in a subject in need thereof. The method comprises administering to the subject a therapeutically effective amount of a compound of the invention. In certain embodiments, the disease or disorder is selected from the group consisting of non-alcoholic fatty liver disease (NAFLD), type 2 diabetes (T2D), hypertriglyceridemia, obesity, metabolic syndrome, Rett's syndrome, metabolic syndrome associated with aging, metabolic diseases associated with increased reactive oxygen species (ROS), Friedreich's ataxia, and/or insulin resistance.

In certain embodiments of the invention, the effective amount of a therapeutic composition comprising a compound of the invention is greater than about 0.01 mg/kg. In other embodiments, the effective amount of the administered compound is between about 0.01 mg/kg to about 1000 mg/kg and any and all whole or partial increments therebetween, including about 0.1 mg/kg, about 1 mg/kg, about 0.01 mg/kg, about 0.1 mg/kg, about 1 mg/kg, about 10 mg/kg, and about 100 mg/kg. In certain embodiments, the effective amount of the administered compound is about 100 mg/kg. In certain embodiments, the effective amount of the administered compound is about 50 mg/kg. In other embodiments, the effective amount of the administered compound is about 5 mg/kg. In other embodiments, the effective amount of the administered compound is about 2.5 mg/kg.

In certain embodiments of the invention, the effective amount of a therapeutic composition comprising a compound of the invention is greater than about 0.05 μmoles/kg. In other embodiments, the effective amount of the administered compound is between about 0.05 μmoles/kg to about 5000 μmoles/kg and any and all whole or partial increments therebetween, including about 0.5 μmoles/kg, about 5 μmoles/kg, about 0.05 μmoles/kg, about 0.5 μmoles/kg, about 5 μmoles/kg, about 50 μmoles/kg, and about 500 μmoles/kg. In certain embodiments, the effective amount of the administered compound is about 500 μmoles/kg. In certain embodiments, the effective amount of the administered compound is about 250 μmoles/kg. In other embodiments, the effective amount of the administered compound is about 25 μmoles/kg. In other embodiments, the effective amount of the administered compound is about 12.5 μmoles/kg.

The invention also includes a method of increasing energy expenditure in a subject in need thereof, the method comprising administering to the subject a therapeutically effective amount of at least one DNP derivative of the invention, whereby energy expenditure in the subject is increased in the subject, wherein the composition is formulated for sustained release of the DNP derivative of the invention.

In certain embodiments, the method further comprises administering to the subject an additional therapeutic agent useful in treating a disease or disorder. In certain embodiments, administering the compound of the invention to the subject allows for administering a lower dose of the additional therapeutic agent compared to the dose of the additional therapeutic agent alone that is required to achieve similar results in treating or preventing a disease or disorder in the subject. For example, in certain embodiments, the compound of the invention enhances the anti-disease or disorder activity of the additional therapeutic agent, thereby allowing for a lower dose of the therapeutic agent to provide the same effect.

In certain embodiments, the compound of the invention and the additional therapeutic agent are co-administered to the subject. In other embodiments, the compound of the invention and the additional therapeutic agent are co-formulated and co-administered to the subject.

In certain embodiments, the subject is a mammal. In other embodiments, the mammal is a human.

Combination Therapies

The compounds useful within the methods of the invention may be used in combination with one or more additional agents useful for treating a disease or disorder. These additional agents may comprise compounds that are commercially available or synthetically accessible to those skilled in the art. These additional agents are known to treat, prevent, or reduce the symptoms of a disease or disorder.

In non-limiting examples, the compounds useful within the invention may be used in combination with one or more of the following therapeutic agents:

Pulmonary Hypertension Drugs: ambrisentan, bosentan, treprostinil, sildenafil, epoprostenol, treprostenol, iloprost, aldosterone receptor antagonists like spironolactone and eplerenone, angiotensin-converting enzyme inhibitors such as trandolapril, fosinopril, enalapril, captopril, ramipril, moexipril, lisinopril, quinapril, benazepril, and perindopril;

Angiotensin II Inhibitors: eprosartan, olmesmian, telmismian, losartan, valsmian, candesartan, and irbesmian, antianginal agents like nitroglycerin, isosorbide mononitrate, and isosorbide dinitrate, anti-arrhythmic agents including moricizine, quinidine, disopyramide, phenyloin, propafenone, flecamide, mexilitene, lidocaine, procainamide, propranolol, acebutolol, amiodarone, dofetilide, dronedarone, sotalol, ibutilide, diltiazem, verapamil, nifedipine, nimodipine, felodipine, nicardipine, clevidipine, isradipine, bepridil, nisoldipine, adenosine, and digoxin;

β-adrenergic Receptor Antagonists: betaxolol, bisoprolol, metoprolol, atenolol, nebivolol, nadolol, carvedilol, labetalol, timolol, carteolol, penbutolol, pindolol, and esmolol;

Anti-Diabetic Agents: insulin, GLP-1 agonists, DPP4 inhibitors, SGLT-2 inhibitors, secretagogues such as sulfonylurea, tolbutamide, acetohexamide, tolazamide, chlorpropamide, glipizide, glyburide, glimepiride, glibenclamide, gliclazide, meglitinide such as nateglinide, senaglinide, repaglinide, insulin sensitizers such as biguanides, metformin, thiazolidinediones such as rosiglitazone, isaglitazone, darglitazone, englitazone, and pioglitazone;

α-Glucosidase Inhibitors: miglitol, voglibose, emiglitate, and acarbose;

Glucagon-Like Peptide Analogs and Agonists: exenatide, liraglutide, and taspglutide, dipeptidyl peptidase-4 inhibitors like vildagliptin, sitagliptin, and saxagliptin;

Amylin Analogs: pramlintide;

Ligands or Agonists of Peroxisome Proliferator Activated Receptor (PPAR)-α, β, δ, and γ Cholesterol-Lowering Agents: hydroxymethylglutaryl-Coenzyme A (HMG-CoA) reductase inhibitors like statins, such as, e.g., atorvastatin, fluvastatin, lovastatin, pitavastatin, pravastatin, rosuvastatin, and simvastatin;

Agonists of Retinoid X Receptors (RXR): ALRT-268, LG-1268, or LG-1069; glucokinase activators, inhibitors of hepatic enzymes involved in stimulation of gluconeogenesis and/or glycogenolysis, Diuretics: acetazolamide, dichlorphenamide, methazolamide, torsemide, furosemide, bumetanide, ethacrynic acid, amiloride, triamterene, indapamide, metolazone, methylclothiazide, hydrochlorothiazide, chlorothiazide, metolazone, bendroflumethiazide, polythiazide, and chlorthalidone;

Vasodilators: alprostadil, hydralazine, minoxidil, nesiritide, and nitroprusside;

Anti-Lipidemic Agents: cholestyramine, colestipol, clofibrate, gemfibrozil, probucol or dextrothyroxine.

Adipocytokines: leptin, adiponectin, and metreleptin;

Drugs for the treatment of Hyperlipidemia: fibrates, omega fatty acids, fish oil, statins.

A synergistic effect may be calculated, for example, using suitable methods such as, for example, the Sigmoid-$E_{max}$ equation (Holford & Scheiner, 1981, Clin. Pharmacokinet.

6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

A skilled artisan armed with the DNP derivatives of the invention would recognize that the derivatives can be optimized for therapeutic outcome by modulating the route of administration, dosage, and formulation by which the derivative is delivered to the subject in need thereof.

The regimen of administration may affect what constitutes an effective amount. The therapeutic formulations may be administered to the subject either prior to or after the onset of a disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the invention to a patient, preferably a mammal, more preferably a human, may be carried out using known procedures, at dosages and for periods of time effective to treat a disease or disorder in the patient. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder in a patient.

In certain embodiments, the compositions of the invention are formulated using one or more pharmaceutically acceptable excipients or carriers. In certain embodiments, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of G-protein receptor-related diseases or disorders. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Dosing

The therapeutically effective amount or dose of a compound of the invention depends on the age, sex and weight of the patient, the current medical condition of the patient and the progression of a disease or disorder in the patient being treated. The skilled artisan is able to determine appropriate dosages depending on these and other factors.

A suitable dose of a compound of the invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the viral load, to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art recognizes, or is able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the invention. Moreover, all values that fall within these ranges, as well as the upper or lower limits of a range of values, are also contemplated by the present application.

The following examples further illustrate aspects of the invention. However, they are in no way a limitation of the teachings or disclosure of the invention as set forth herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1: Reversal of Hypertriglyceridemia, Fatty Liver and Insulin Resistance by a Novel Liver-Targeted Mitochondrial Uncoupler Liver-targeted DNP derivatives that would be preferentially metabolized by liver and converted to DNP were synthesized and screened. DNP-methyl ether (DNPME) was identified and examined further to determine if it could safely decrease hypertriglyceridemia, NAFLD and insulin resistance without systemic toxicities. Treatment with DNPME both prevented and reversed hypertriglyceridemia, fatty liver and whole-body insulin resistance in high-fat fed rats and decreased hyperglycemia in a rat model of T2D with a clinically acceptable therapeutic index. The reversal of liver and muscle insulin resistance could be attributed to reductions in tissue diacylglycerol content and reductions in PKCε and PKCθ activity in liver and muscle, respectively. These results described herein demonstrate that the beneficial effects of DNP on hypertriglyceridemia, fatty liver and insulin resistance can be dissociated from systemic toxicities and are proof of concept for developing liver-targeted mitochondrial uncoupling agents for the treatment of the related epidemics of NAFLD, metabolic syndrome and type 2 diabetes.

Materials and Methods
Screening of Compounds

To screen compounds, the ability of the compounds to raise oxygen consumption rates in vivo was assessed using the Seahorse Extracellular Flux Analyzer (Seahorse Bioscience, North Billerica, Mass.). Primary hepatocytes were isolated (Neufeld, 1997, Methods. Mol. Biol. 75:145-151) and plated on a collagen-coated 24-well plate (Seahorse Bioscience, North Billerica, Mass.). After a 6-hour incubation period, cells were transferred to the Seahorse XF Analyzer for measurement of oxygen consumption rate. Basal oxygen consumption was measured, then sequential additions of DNP (positive control) or the candidate compounds raised the concentration of the putative uncoupler to 10, 100, 500, or 1000 μM. Absolute oxygen consumption rates were normalized to the oxygen consumption rate measured before the first addition of uncoupler.

Animals

All animals were male. C57BL6J mice were ordered from Jackson Laboratories at 25 g. Sprague-Dawley and Zucker Diabetic Fatty rats weighing 300-400 g were ordered from Charles River Laboratories. All animals were allowed to acclimate for 1-3 weeks before use. Unless otherwise noted, animals were fed normal chow (Harlan 2018 [58% calories from carbohydrate, 24% from protein, 18% from fat], Harlan, Indianapolis, Ind.). Where specified, animals were fed safflower oil based high fat diet (Dyets, Inc., Bethlehem, Pa.) with 60% calories from fat. All animals had ad libitum access to water at all times. Where specified, caloric intake was enriched by free access to 5% sucrose water. Rats used for experiments requiring blood collection underwent surgery under isoflurane anesthesia to place catheters in the jugular vein and internal carotid artery. Another group of rats underwent surgery to place catheters in the antrum of the stomach. All animals were allowed to recover for at least 1 week before any further experiments were performed.

Rats used for the studies to determine whether DNPME could prevent the development of NAFLD were fed high fat diet and sucrose water for 2 weeks, during which time they were concurrently injected with daily 5 mg/kg IP doses of DNPME in 100% DMSO (250 l/kg body weight) or vehicle. Rats used for the NAFLD reversal studies were fed high a fat diet and sucrose water for 1 week, then were given daily injections of DNPME or vehicle for 5 days while continuing the high fat diet and sucrose water. To measure caloric intake, the volume of water and weight of food consumed each day were measured, and calorie content was calculated using the known composition of each item.

To induce mild beta-cell defect and type 2 diabetes, rats were injected with 75 mg/kg nicotinamide and, following a 15 minute wait, the rats were injected with 60 mg/kg streptozotocin. Animals were allowed to recover for 3 days, and those with random plasma glucose between 150 and 350 mg/dl were used for further study. At this time, high fat diet and sucrose water feeding was initiated. After 3 days of feeding, two weeks of daily DNPME or vehicle injections were begun.

Toxicity Studies

For the acute toxicity studies, rats were treated with an IP injection of DNPME in 100% DMSO at doses 1, 2.5, 5, 10, 25, 50, 100, and 200 mg/kg body weight. Rectal temperature was measured with a microprobe thermometer (Physitemp Instruments, Clifton, N.J.) at intervals up to 2 hours after injection of the drug. Rectal temperature was measured weekly in a separate group of rats injected daily with DNPME or vehicle for 6 weeks. A separate group of rats were injected with increasing doses of DNP or DNPME in 100% DMSO to determine the 50% lethal dose ($LD_{50}$). The 50% lethal dose was taken to be the dose at which 50% of rats died within 24 hours of treatment.

To assess renal and hepatic toxicity, a group of catheterized rats was treated with an intraperitoneal (IP) injection of DMSO vehicle or 1, 2.5, 5, 10, 25 50, 100, or 200 mg/kg DNPME in DMSO daily. After five days, the rats were sacrificed and plasma obtained from the intravenous catheter. The COBAS Mira Plus (Roche Diagnostics, Indianapolis, Ind.) was used to measure plasma alanine aminotransferase (ALT), aspartate aminotransferase (AST), and blood urea nitrogen (BUN). Plasma creatinine was measured by liquid chromatography/mass spectrometry/mass sprectrometry (LC/MS/MS). 24 hour creatinine clearance was measured by housing rats treated with DNPME or vehicle in metabolic cages for 24 hours, collecting the urine, and measuring urine creatinine concentration by LC/MS/MS.

Intragastric DNP Infusion

Rats underwent surgery to place catheters in the antrum of the stomach, the jugular vein and carotid artery. Following a week of recovery, the animals were placed in a Covance infusion harness (Instech Solomon, Plymouth Meeting, Pa.) to protect the catheters, and DNP was infused intragastrically at a rate of 2 mg/kg per day for 5 days. An equal volume (2 ml/day) of DMSO vehicle was infused in controls. During this period, rats had free access to safflower oil high fat diet and 5% sucrose water.

Histology Studies

Liver and kidney samples were prepared and stained with hematoxylin & eosin, and analyzed (Kleiner et al., 2005, Hepatology 41:1313-1321).

Glucose Tolerance Tests

Following an overnight fast, rats with a jugular venous line were injected with a 1 g/kg intraperitoneal bolus of 50% dextrose. Blood samples were taken through the venous line before and 5, 10, 20, 30, 45, 60, and 90 min after the dextrose injection. Plasma glucose was measured enzymatically on the YSI Life Sciences 2700 Select Biochemistry Analyzer (Yellow Springs, Ohio), and plasma insulin was measured by radioimmunoassay. Area under the curve was measured from time point A to subsequent time point B according to the following formula:

$$AUC_{A \to B} = \frac{1}{2}(\text{Plasma glc}_A + \text{Plasma glc}_B) \times (\text{Time}_B - \text{Time}_A)$$

The total area under the curve was calculated by adding the area under the curve of each of the subsequent time periods. The insulin area under the curve was calculated in the same way.

Basal and Insulin-Stimulated Glucose Turnover Studies

Hyperinsulinemic-englycemic clamps were performed and basal and insulin-stimulated glucose turnover were measured using $[6,6]^2H$ glucose (Erion et al., 2013, Endocrinology 154:36-44). To measure insulin-stimulated glucose uptake in heart and quadriceps muscle, $[^{14}C]$2-deoxyglucose was injected at the conclusion of the clamp, and tissues processed (Samuel et al., 2007, J. Clin. Invest. 117:739-745).

Insulin Signaling

PKCε translocation in liver and PKCθ translocation in muscle from 6-hour fasted rats in the NAFLD treatment study were measured by Western blot (Choi et al., 2007, Proc. Natl. Acad. Sci. USA 104:16480-16485).

Lipid Concentration Assays

Triacylglycerol (TAG) in liver and quadriceps muscle were extracted (Bligh & Dyer, 1959, Can. J. Biochem. Physiol. 37:911-917) and measured spectrophotometrically with Diagnostic Chemicals triglyceride reagent (Diagnostic Chemicals Ltd [DCL], Charlottetown, Canada). Liver and quadriceps diacylglycerol (DAG) were extracted by homogenization in a buffer containing 20 mM Tris-HCl, 1 mM EDTA, 0.25 mM EGTA, 250 mM sucrose, 2 mM phenylmethylsulfonyl fluoride, and a protease inhibitor mixture (Roche, Indianapolis, Ind.). The cytosolic fragment was isolated from the supernatant after high speed centrifugation for 1 hour. Diacylglycerol (DAG) and ceramide content was measured by liquid chromatography/mass spectrometry/mass spectrometry (Bligh & Dyer, 1959, Can. J. Biochem. Physiol. 37:911-917).

To measure liver triglyceride export, 300 mg/kg of a lipoprotein lipase (LPL) inhibitor, Poloxamer 407 (Sigma, St. Louis, Mo.) was injected, and plasma was sampled at time 0, 1, 2, 3, and 4 hours after treatment. Plasma triglyceride concentration was measured using the DCL triglyceride reagent. Because LPL was assumed to be completely inhibited by this dose of Poloxamer, triglyceride accumulation in plasma was assumed to be proportional to hepatic triglyceride export. Thus, the slope of the least-squares regression of the graph of plasma triglyceride concentration versus time (Microsoft Excel, Redmond, Wash.) was considered to be the TAG export rate. Tissue ceramide content was measured by LC/MS/MS (Yu et al., 2002, J. Biol. Chem. 277:50230-50236).

Measurement of Liver Glycogen Content

Hepatic glycogen content was assessed by amyloglucosidase digestion (Passonneau & Lauderdale, 1974, Anal. Biochem. 60:405-412).

Assessment of Potential Gluconeogenic Markers

Plasma concentrations of twelve inflammatory markers were measured by ELISA (QIAGEN, Valencia, Calif.). Adiponectin was measured by ELISA. Lactate was measured by COBAS, and FGF-21 by ELISA (Millipore).

Assessment of Whole Body Energy Metabolism

Mice were studied during daily IP injections of 5 mg/kg DNPME or vehicle. Comprehensive Animal Metabolic Monitoring System (Columbus Instruments, Columbus, Ohio) was used to measure oxygen uptake and carbon dioxide production, daily caloric intake and energy expenditure, respiratory exchange ratio, and activity throughout the day.

Evaluation of Hepatic Flux Rates in Rats

To measure liver-specific flux through the TCA cycle, a steady-state infusion of $[3-^{13}C]$ lactate (5 min prime 120 µmol/[kg-min], 115 min continuous infusion 40 µmol/[kg-min]) and $[^3H]$ glucose (44 µmol/min) was performed. At 120 min, plasma and livers were isolated, and hepatic fluxes were measured by nuclear magnetic resonance (NMR) and LC/MS/MS.

Measurement of Hepatic Positional Metabolite Enrichment

To measure total glutamate enrichment from livers of rats infused with $[3-^{13}C]$ lactate, ~100 mg frozen liver were homogenized in 400 µL ice-cold 50% acetonitrile. The samples were centrifuged at 10,000 g for 10 min, and the supernatant was isolated. After overnight storage at 4° C., the samples were centrifuged at 10,000 g for 10 min through a Nanosep 100 k Omega filter (Pall Life Sciences). The flow-through was separated on a hypercarb column (Thermo Scientific; 4.6×100 mm; 5 µm particle size) before ionization for multiple reaction monitoring analysis by LC/MS/MS (Applied Biosystems MDS SCIEX, 4000 Q-TRAP).

To measure positional glutamate and alanine enrichment, the liver samples were extracted for nuclear magnetic resonance (NMR) spectroscopy. ~4-6 g ground liver were centrifuged in ~30 mL 7% perchloric acid. The pH of the supernatant was adjusted to 6.5-7.5 using 30% potassium hydroxide and 7% perchloric acid as needed, and the extract was dehydrated by lyophilizing for 2-3 days. The extract was resuspended in 500 µL potassium phosphate buffer: 2.4 mM NaCOOH, 30 mM $K_2HPO_4$, 10 mM $KH_2PO_4$, 20 mM DMSO (internal standard) in 100% $D_2O$. $^{13}C$ NMR spectra were collected using the AVANCE 500-MHz NMR spectrometer (Bruker Instruments).

Spectra were acquired with relaxation time=1 s, dummy scans=32, and number of scans=8,192 per block×3 blocks. Correction factors for differences in $T_1$ relaxation times were determined from fully relaxed spectra of natural abundance glutamate and glucose solutions. The total glutamate enrichment by LC/MS/MS was divided algebraically according to the peak areas of $[^{13}C]$ glutamate for each carbon corrected for T1 relaxation times.

Total glucose enrichment in the NMR extract was determined by derivatizing 20 µL of the NMR extract with 100 µL methanol, then drying overnight in a Speed-Vac. The extract was then resuspended in 75 µL 1:1 acetic anhydride: pyridine and heated for 20 min at 65° C. The sample was cooled and quenched with 25 µL methanol. The total m+1 glucose enrichment of each sample was measured by gas chromatography/mass spectrometry (Shulman et al., 1985, J. Clin. Invest. 76:757-764). m+2, m+3, m+4, m+5, and m+6 enrichment were found to be negligible (<5% of m+1 enrichment at steady-state). $^{13}C$ NMR spectra were used to determine relative concentrations of $[^{13}C]$ glucose. As for glutamate, the total glucose enrichment by mass spectrometry was divided algebraically to measure the enrichment at each glucose carbon.

To measure positional alanine enrichment from $[3-^{13}C]$ lactate infused rat livers, liver samples were extracted for NMR as described above, and the enrichment at $[2-^{13}C]$ and $[3-^{13}C]$ alanine was measured by proton-observed, carbon-edited NMR (Alves et al., 2011, Hepatology 53:1175-1181).

Measurement of Absolute Hepatic Flux Rates

Livers from rats infused with [3-$^{13}$C] lactate and [$^3$H] glucose were extracted with perchloric acid (Alves et al., 2011, Hepatology 53:1175-1181). Basal glucose turnover was measured (Maggs, 1998, Annals of Internal Medicine 128:176-185); as these rats were overnight fasted with low hepatic glycogen concentrations (FIG. 6P), all glucose production was presumed to be from gluconeogenesis. It was assumed that gluconeogenesis was 90% hepatic and 10% renal; from whole-body gluconeogenesis data, the absolute hepatic gluconeogenesis could then be calculated. [3-$^{13}$C] lactate infusion permitted the measuring of the percent gluconeogenesis from pyruvate (flux through pyruvate carboxylase, VPC) according to the following equation:

$$\text{Gluconeogenesis from pyruvate} = \frac{[1-^{13}C] + [2-^{13}C] + [5-^{13}C] \text{ glucose}}{[2-^{13}C] + [3-^{13}C] \text{ glutamate}}.$$

Flux could be expressed through PC relative to TCA cycle flux using the following equation:

$$V_{ana}/V_{tca} = (C4^*Glu - C2^*Glu)/[(C2^*Glu + C3^*glu) - (C3^*Pyr + C2^*Pyr)]$$

because the absolute $V_{PC}$ had previously been calculated as described above, $V_{TCA}$ could be back-calculated from these data. Finally, using the following equation:

$$\frac{V_{PDH}}{V_{TCA}} = \frac{[4-^{13}C] \text{ gluamate}}{[3-^{13}C \text{ alaine}]};$$

from the calculated $V_{TCA}$, $V_{PDH}$ could be determined using this equation, and the contribution of fatty acid oxidation to the TCA cycle could be determined as the difference between $V_{TCA}$ and $V_{PDH}$.

Measurement of Plasma and Tissue DNP and DNPME Concentrations

LC/MS/MS method development and analysis were performed on the Applied Biosystems 4000 QTRAP (Foster City, Calif.), equipped with a Shimadzu ultrafast liquid chromatography (UFLC) system. Electrospray ionization (ESI) source with negative-ion detection was shown as the most sensitive for both qualitative and quantitative analysis of DNP and DNPME. The quantitative analysis of DNP was monitored in MRM mode with an ion pair (183.0/109.0). The preferred parameters are: curtain gas 25; collision gas 9, probe temperature 480° C.; ion source gas 1 20; ion source gas 2 25; declustering potential (DP) −45 V; entrance potential (EP) −10 V; collision energy (CE) −35 V and collision cell exit potential −12 V.

The molecular radical anion of DNPME is unstable at the ionization temperature due to the labile methyl-oxygen ether bond, but the fragmented DNP anion is one of the most abundant peaks for DNPME using the parameters optimized for DNP, thus both DNP and DNPME can be quantitated by the same method. A Hibar LiChrosorb analytical HPLC column (RP-C8, 4×125 mm, particle size 5 μM) (Merck KGaA, Darmstadt, Germany) was used to separate DNP and DNPME using an isocratic flow (250 μl/min) of 15% 10 mM ammonium formate and 85% methanol/water (95/5). The retention time was about 4 min for DNP, and about 7 min for DNPME. Deuterated 2,4-dinitrophenol (DNP-D$_3$) and deuterated DNP-methyl ether (DNPME-D$_6$) were used as the internal standards for DNP and DNPME quantitation, respectively.

Extraction from Plasma Samples for LC/MS/MS Analysis

Plasma samples (10-100 μL) were mixed with 2.0 ml pre-chilled chloroform/methanol (v/v: 2/1) containing 0.01% BHT in 5 ml glass vials, to which was added 250 μl water together with 10 nmol DNP-D$_3$ and 10 nmol DNPME-D$_6$ as the internal standards. The mixtures were vortexed for 10 seconds before centrifugation at 4,000 rpm for 10 min. The bottom organic layer was carefully collected and dried with a steady stream of nitrogen gas. The residual was reconstituted in 200 μl methanol for LC/MS/MS analysis for DNP and/or DNPME metabolites.

Extraction from Various Tissue Samples for LC/MS/MS Analysis

Frozen tissue samples (~100 mg) were weighed and suspended in 2 ml microcentrifuge tubes with 1.6 ml pre-chilled chloroform/methanol (v/v: 2/1) containing 0.01% BHT and one metal bead, and then added 10 nmol DNP-d$_3$ (Cambridge Isotopes, Andover, Mass.) and 10 nmol DNPME-d$_6$ (synthesized as described above) as the internal standards. The tissue samples were disrupted with Qiagen TissueLyser at 30 Hz for 15 min, and then transferred into 5 ml glass vials, followed by addition of 0.5 ml chloroform and 250 μl water into each samples. The samples were centrifuged at 4,000 rpm for 10 min after vortexed for 10 seconds. The bottom organic layer was collected and dried with a gentle flow of nitrogen. The residual was reconstituted in 200 μl methanol for LC/MS/MS analysis of DNP and/or DNPME metabolites.

Kinetics Studies

To evaluate the kinetics of DNP and DNPME, a 5 mg/kg dose of DNPME was injected in six rats at time zero. Rats were sacrificed at 1, 2, 4, 6, 12, and 24 hours to isolate the liver, and plasma was drawn through a venous catheter at each time point. Plasma and liver were isolated and immediately frozen in liquid nitrogen. Plasma and liver concentrations of DNP and DNPME were measured by LC/MS/MS.

To compare tissue concentrations of DNPME and DNP with various injection protocols, separate groups of rats (n=4 per group) were treated with DNPME or DNP as follows:

(i) 5 mg/kg DNPME, (ii) 5 mg/kg DNP, (iii) 25 mg/kg DNP

The DNPME injected rats were sacrificed 4 hours after the last injection, while the DNP injected rats were sacrificed 1 hour after the last injection, times which in the previous kinetics studies had been determined to represent the peak plasma concentrations of DNP with the respective injections. Plasma and tissues (liver, heart, white adipose tissue, quadriceps, brain, and kidney) were isolated.

Mitochondrial Respiration Studies

Isolated mitochondria from liver and brain of overnight fasted rats were prepared (Andrews et al., 2008, Nature 454:846-851). Tissues were homogenized on ice in 10-20× volume of isolation buffer containing 215 mM mannitol, 75 mM sucrose, 0.1% BSA, 1 mM EGTA, 20 mM HEPES at pH 7.2, and centrifuged for 10 min at 1000 g. The supernatant was then isolated and centrifuged for 10 min at 8000 g. After the high-speed centrifugation, the pellet was resuspended in BSA-free isolation buffer and washed by centrifugation. A Bradford assay was used to measure the protein concentration of each mitochondrial sample. Samples were diluted to 2 mg/ml with BSA free isolation buffer and stored on ice for further study. The Seahorse XF24 Analyzer (Seahorse Biosciences, North Billerica, Mass.) was used to measure mitochondrial respiration in samples plated at 10 μg/well in respiration buffer (215 mM mannitol, 75 mM sucrose, 3 mM $MgCl_2$, 2.5 mM inorganic phosphates, 0.1% BSA, 25 mM MOPS, 10 mM pyruvate, 2.5 mM malate, 2.5 mM glutamate, 5 mM succinate, 2 mM ADP, and 1 μg/ml oligomycin at pH 7.2). Oxygen consumption was measured before and after the addition of DNP or DNPME (0, 3.125, 6.25, and 12.5 μM).

Measurement of Tissue Energetics

Livers from rats sacrifice by decapitation were isolated within 15 seconds, and quadriceps muscle within 40 seconds. ~50 mg of tissue were homogenized in a buffer of 50% methanol, 10 μM EDTA, 2 mM ammonium acetate, and 20 μM taurine-$d_4$. Following a 20 minute spin at 20,000 rcf and 4° C., the supernatant was kept on ice for 20 min, then spun again at 16,000 rcf in filter tubes for 5 min. The flow-through was separated on a C18 5 μm 100 Å 4.6×100 mm column (Phenomenex, Torrance, Calif.) before ionization for multiple reaction monitoring (MRM) analysis by LC/MS/MS (Applied Biosystems/MDS SCIEX, 5000 Q-TRAP). Each analyte was eluted isocratically in 12 uM ammonium formate/5% methanol at a flow rate of 400 μl/min. Individual ion pairs were designated for each analyte, and the relative concentrations were determined by manual integration.

Statistical Analysis

All data are expressed as mean±SEM. Significance was determined using the two-tailed unpaired Student's t-test. Differences with a P-value less than 0.05 were considered significant.

Derivatives of DNP

It was hypothesized that a liver-targeted mitochondrial uncoupling agent might be an effective and safe approach for the treatment of NAFLD and insulin resistance by promoting the oxidation of hepatic triglyceride, while avoiding hyperthermia and associated systemic toxicities that typically occur with classical mitochondrial uncoupling agents.

Figure 5A:
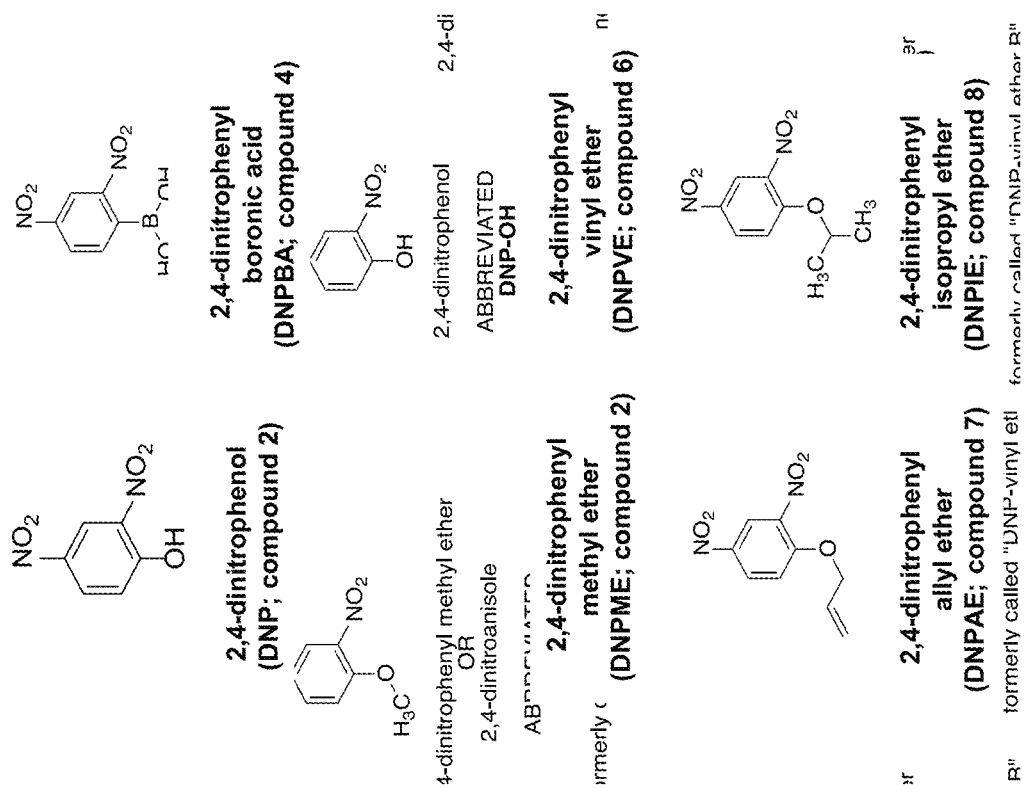
Figures 5B, 5C, 5D, 5E:
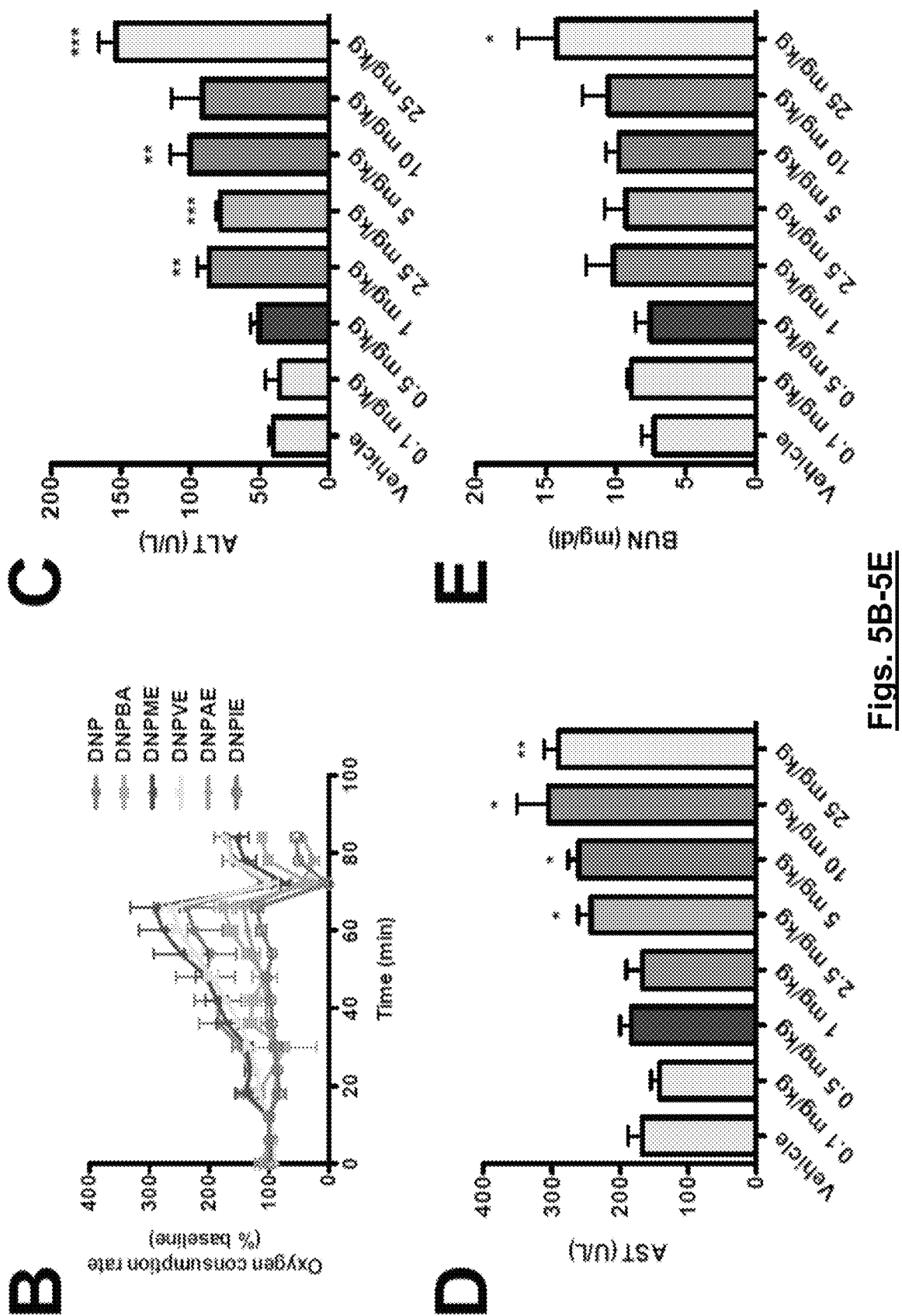

It was hypothesized that targeting DNP to the liver would reduce hypertriglyceridemia, hepatic lipid content and improve insulin sensitivity without DNP-associated toxicities. Several derivatives of DNP were synthesized, and it was hypothesized that these derivatives would be preferentially taken up and metabolized in the liver by the cytochrome P-450 system. The derivatives were screened in isolated hepatocytes for their ability to promote increased oxygen consumption (FIGS. 5A-5B).

From this screen two compounds which raised oxygen consumption rates with similar potencies to DNP were identified (DNP-methyl ether (DNPME) and DNP-vinyl ether (DNPVE) (Ibrahim et al., 1986, Appl. Biochem. Biotechnol. 12:199-213; Stresser and Kupfer, 1998, Biochem. Pharmacol. 55:1861-1871; Zamora et al., 2003, J. Med. Chem. 46:2313-2324).

DNPME In Vivo Metabolic Characterization Studies

Figures 1E, 1F, 1G, 1H:
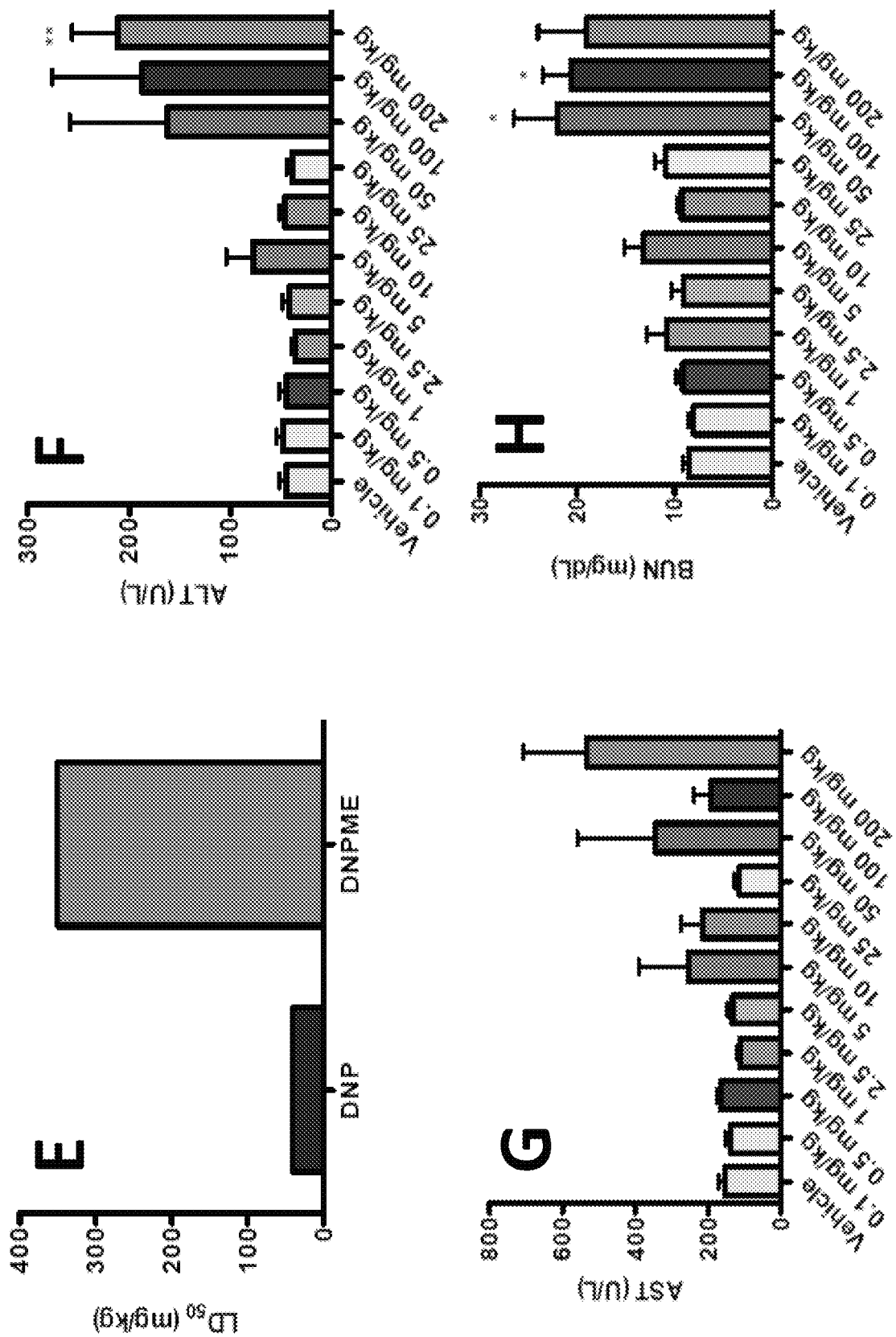
FIG. 1E is a graph illustrating the $LD_{50}$ of DNP and DNPME.
FIG. 1F is a graph illustrating plasma AST after 5 days of daily treatment with DNPME or vehicle.
FIG. 1G is a graph illustrating plasma ALT after 5 days of daily treatment with DNPME or vehicle.
FIG. 1H is a graph illustrating plasma BUN after 5 days of daily treatment with DNPME or vehicle.
Figure 1M:
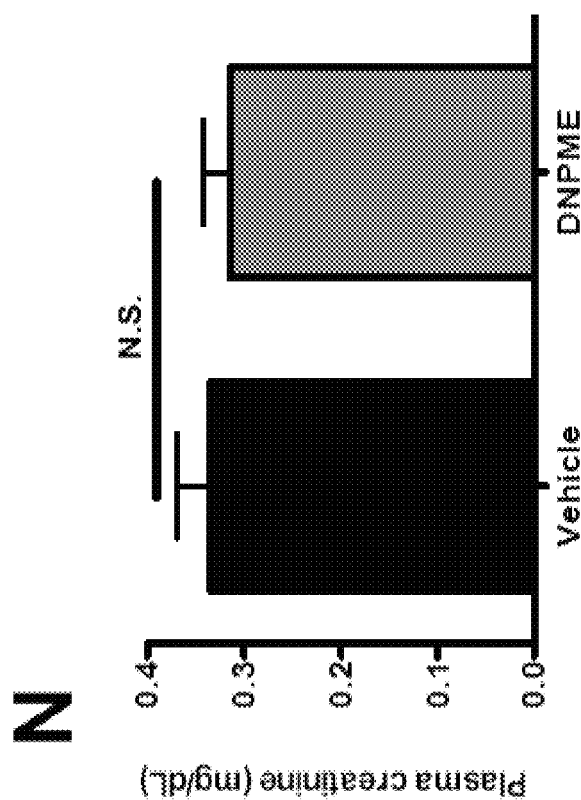
FIG. 1M is a graph illustrating BUN after 6 weeks of daily treatment in chow-fed rats.
Figure 1N:
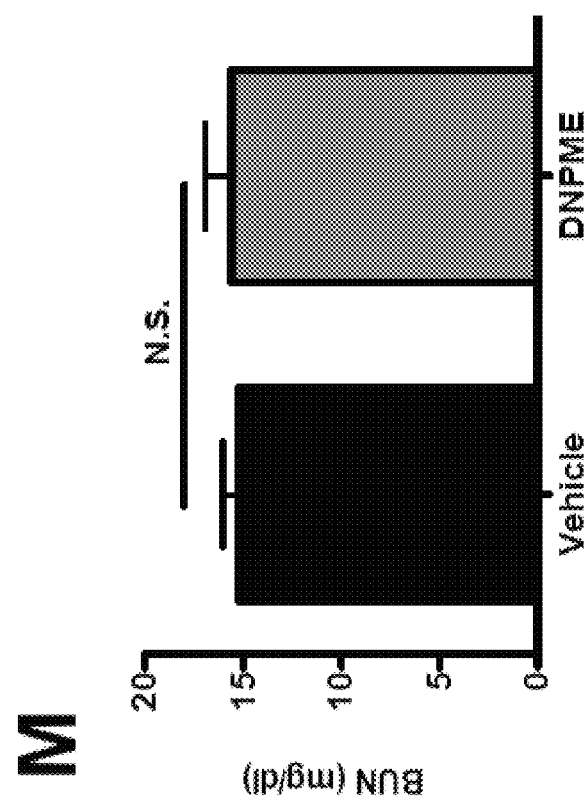

DNPME was selected for further in vivo metabolic characterization studies due to its improved stability under acidic conditions. In contrast to DNP, which caused a large, dose-dependent increase in rectal temperatures and rapid dose-dependent mortality at doses above 10 mg/kg, DNPME caused no such effects after an injection up to 200 mg/kg (FIGS. 1A-1D). Consistent with these findings, the $LD_{50}$ dose of DNPME was almost tenfold higher than that of DNP (FIG. 1E). Five days of daily treatment with DNPME caused no appreciable hepatic or renal toxicity at daily doses below 50 mg/kg (FIGS. 1F-1I), but daily doses above 2.5 mg/kg were effective at reducing hepatic triglyceride accumulation in rats fed a high-fat diet and sucrose supplemented (5%) drinking water (FIG. 1J).

In contrast, the toxic threshold of chronic DNP treatment was determined to be 1 mg/kg, whereas the lowest dose that was effective at lowering liver TAG was 5 mg/kg (FIGS. 5C-5G); thus the ratio of effective to toxic dose was 0.2 for DNP compared to 10 for DNPME. From these data it was found that DNPME had a favorable therapeutic index ($LD_{50}$/$ED_{50}$) of 70. The lowest effective daily dose of DNPME (5 mg/kg), which was tenfold lower than the minimal dose where any indication of hepatic or systemic toxicities was observed, was selected to further characterize its effects on hepatic steatosis and insulin action in vivo. This therapeutic index compares favorably with other drugs that are in common use such as acetaminophen, which has a $LD_{50}$/$ED_{50}$ of 13. Six weeks of daily treatment with DNPME at this dose caused no differences in liver or renal function tests, liver or renal histology, or rectal temperature (FIGS. 1K-1N, 5J-5K).

DNPME Studies in Rat Model of NAFLD

Figures 2A, 2B, 2C, 2D:
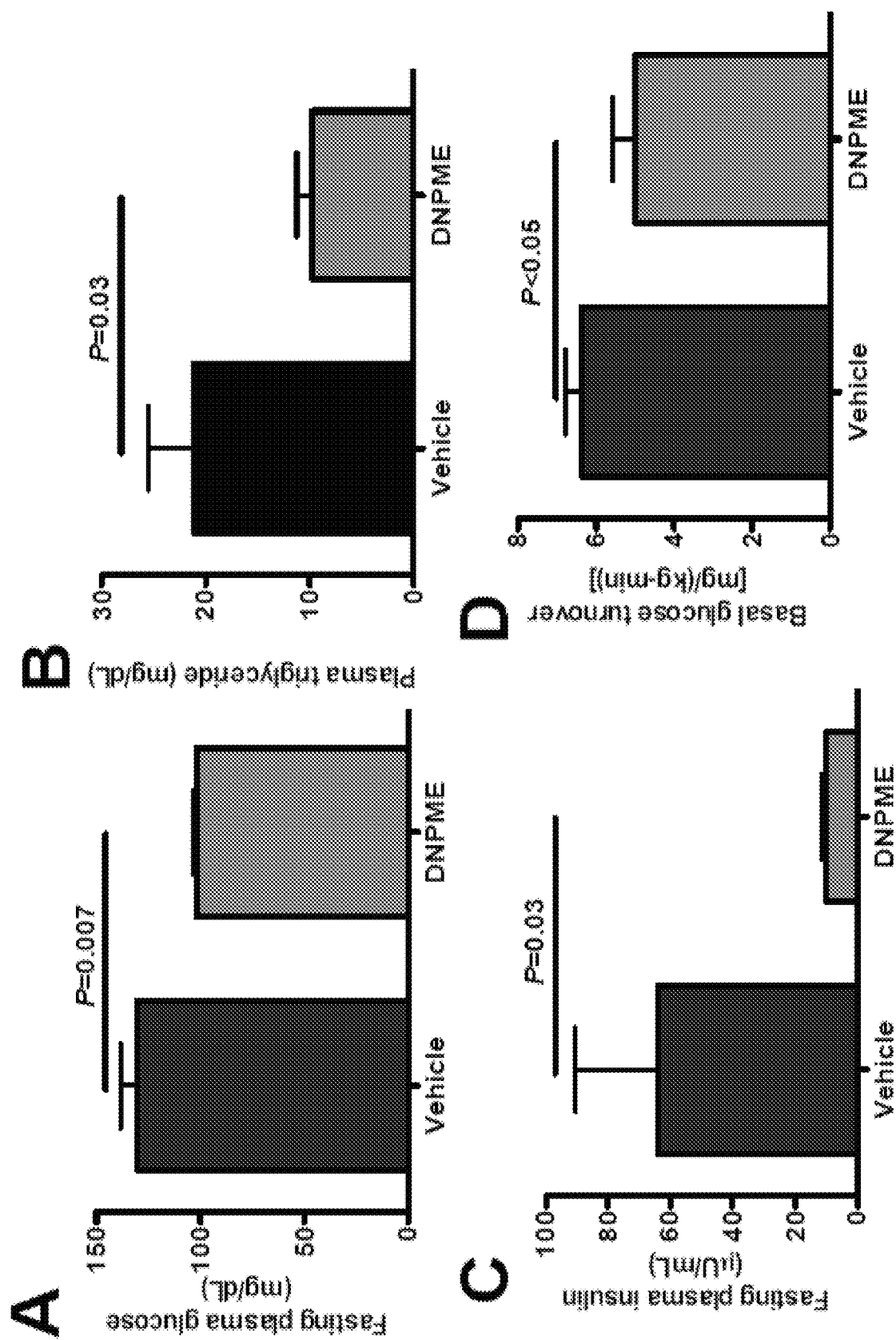
FIGS. 2A-2O, illustrates the finding that DNPME reverses NAFLD, hypertriglyceridemia as well as liver and muscle insulin resistance in fats.
FIG. 2B is a graph illustrating fasting plasma triglyceride.
FIG. 2C is a graph illustrating fasting plasma insulin.
FIG. 2D is a graph illustrating basal glucose turnover.
Figures 6A, 6B, 6C, 6D:
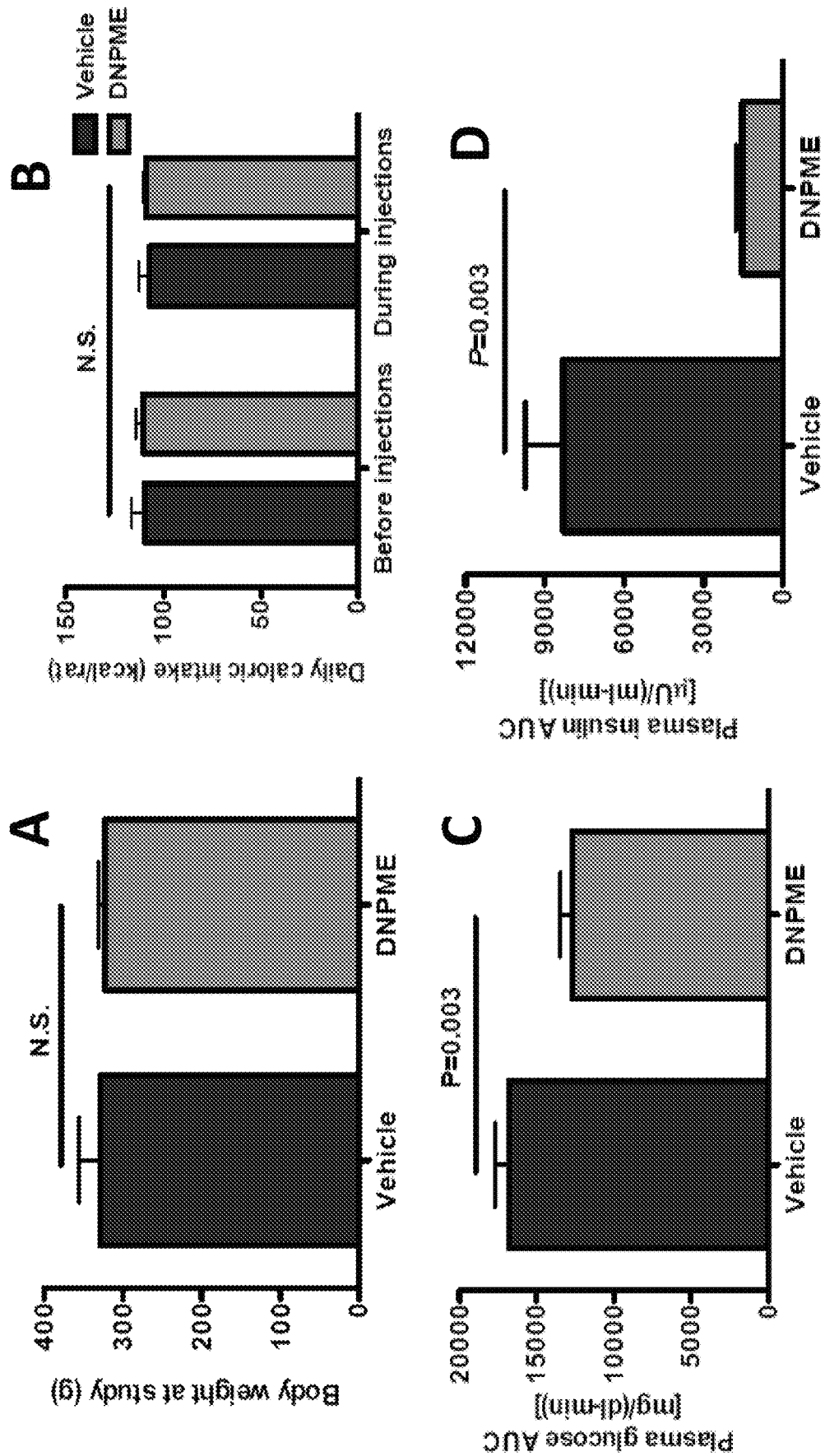
FIGS. 6A-6T, illustrates the finding that DNPME reverses NAFLD and insulin resistance.
FIG. 6B is a graph illustrating food intake before and during injections of DNPME or vehicle.
FIG. 6C is a graph illustrating plasma glucose concentrations area under the curve during an intraperitoneal glucose tolerance test.
FIG. 6D is a graph illustrating plasma insulin concentrations area under the curve during an intraperitoneal glucose tolerance test.
Figures 6E, 6F, 6G, 6H:
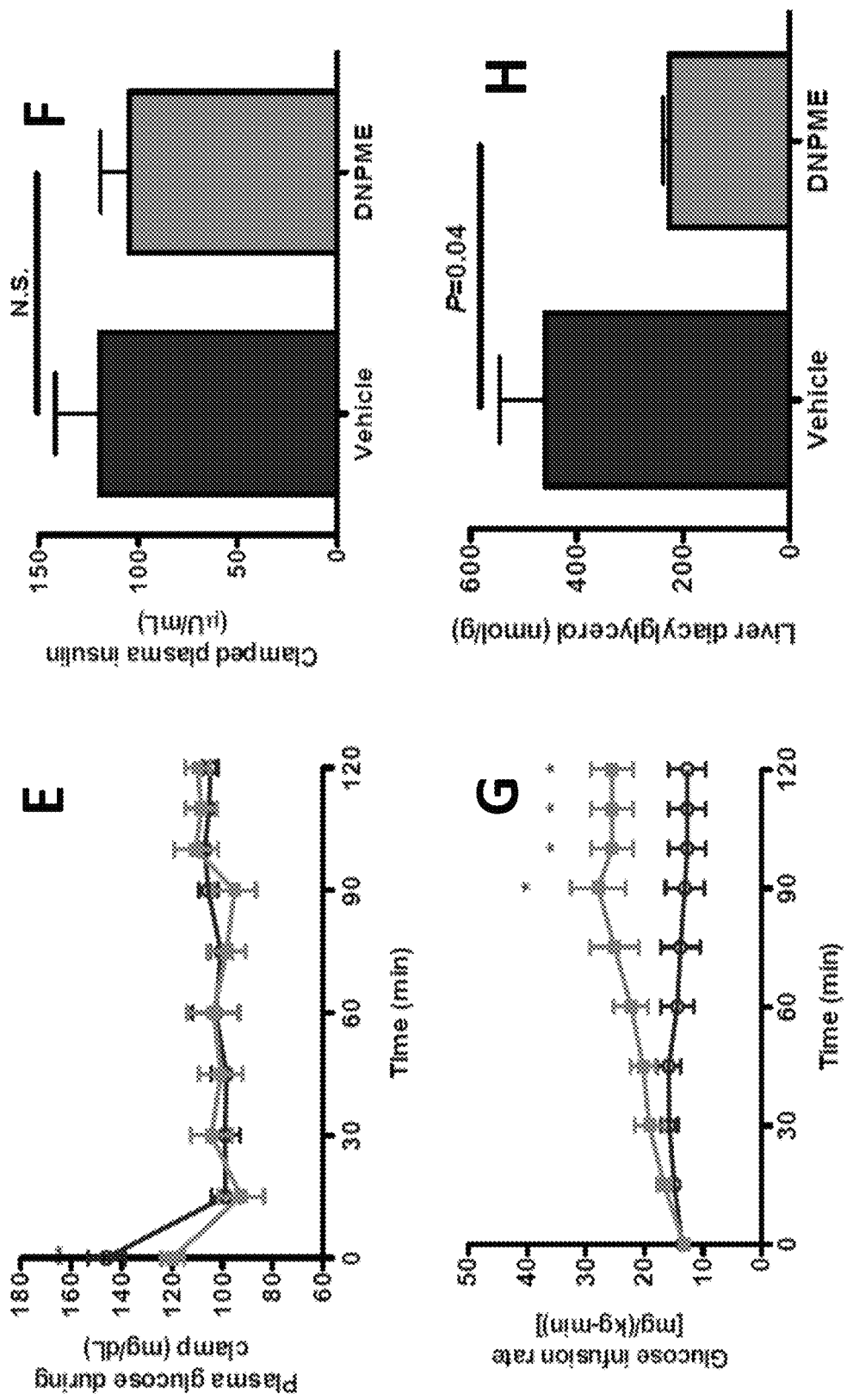
FIG. 6E is a graph illustrating plasma glucose during the hyperinsulinemic-euglycemic clamp.
FIG. 6F is a graph illustrating plasma insulin concentrations at the end of the clamp.
FIG. 6G is a graph illustrating glucose infusion rate required to maintain euglycemia. For FIGS. 6E and 6G: black circles=vehicle treated, red/lgray squares=DNPME treated.
FIG. 6H is a graph illustrating liver DAG content.
Figures 6I, 6J, 6K, 6L:
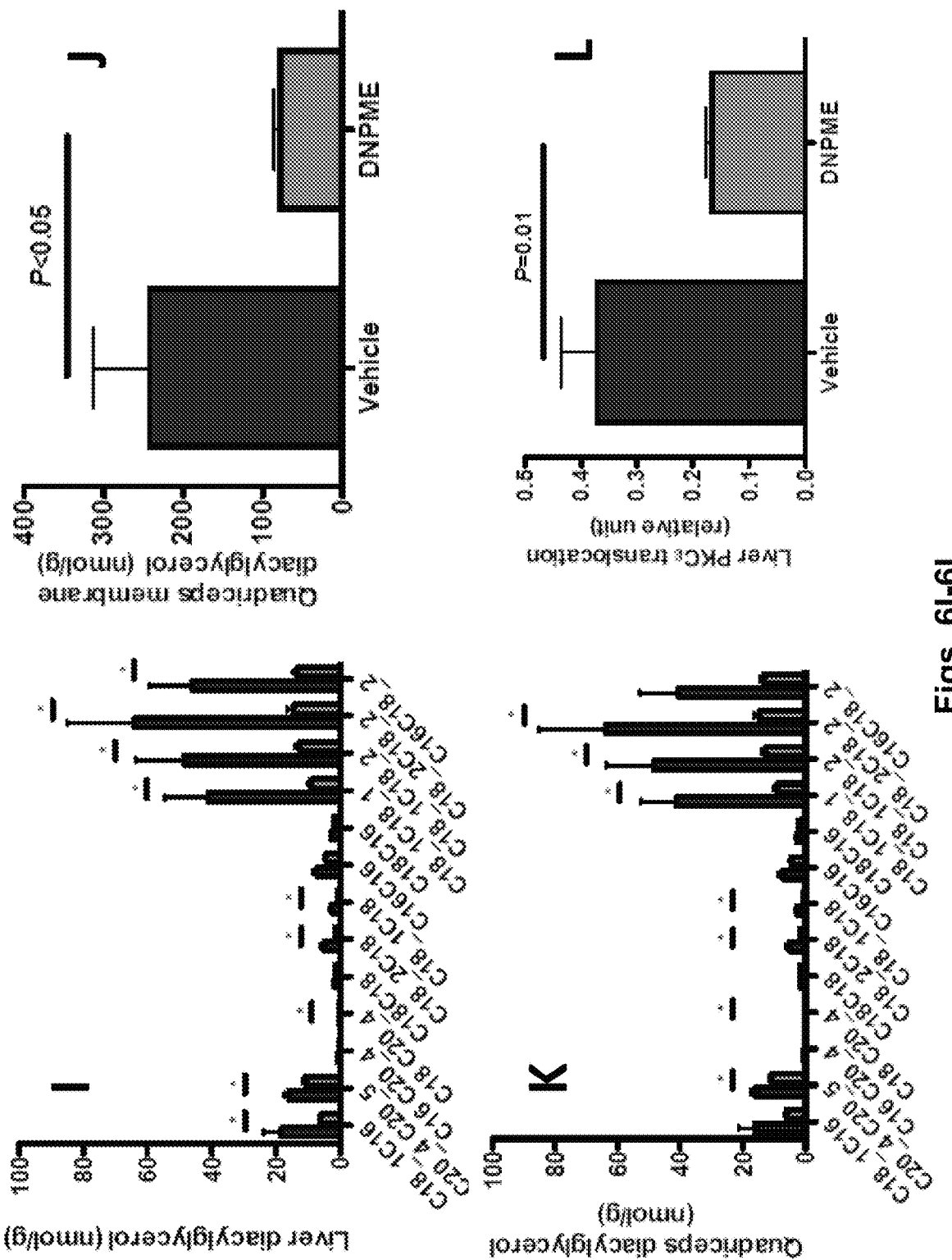
FIG. 6I is a graph illustrating individual DAG species.
FIG. 6J is a graph illustrating quadriceps muscle DAG.
FIG. 6K is a graph illustrating individual DAG species.
FIG. 6L is a graph illustrating liver PKCε translocation (n=10 per group).
Figures 6M, 6N, 6O, 6P:
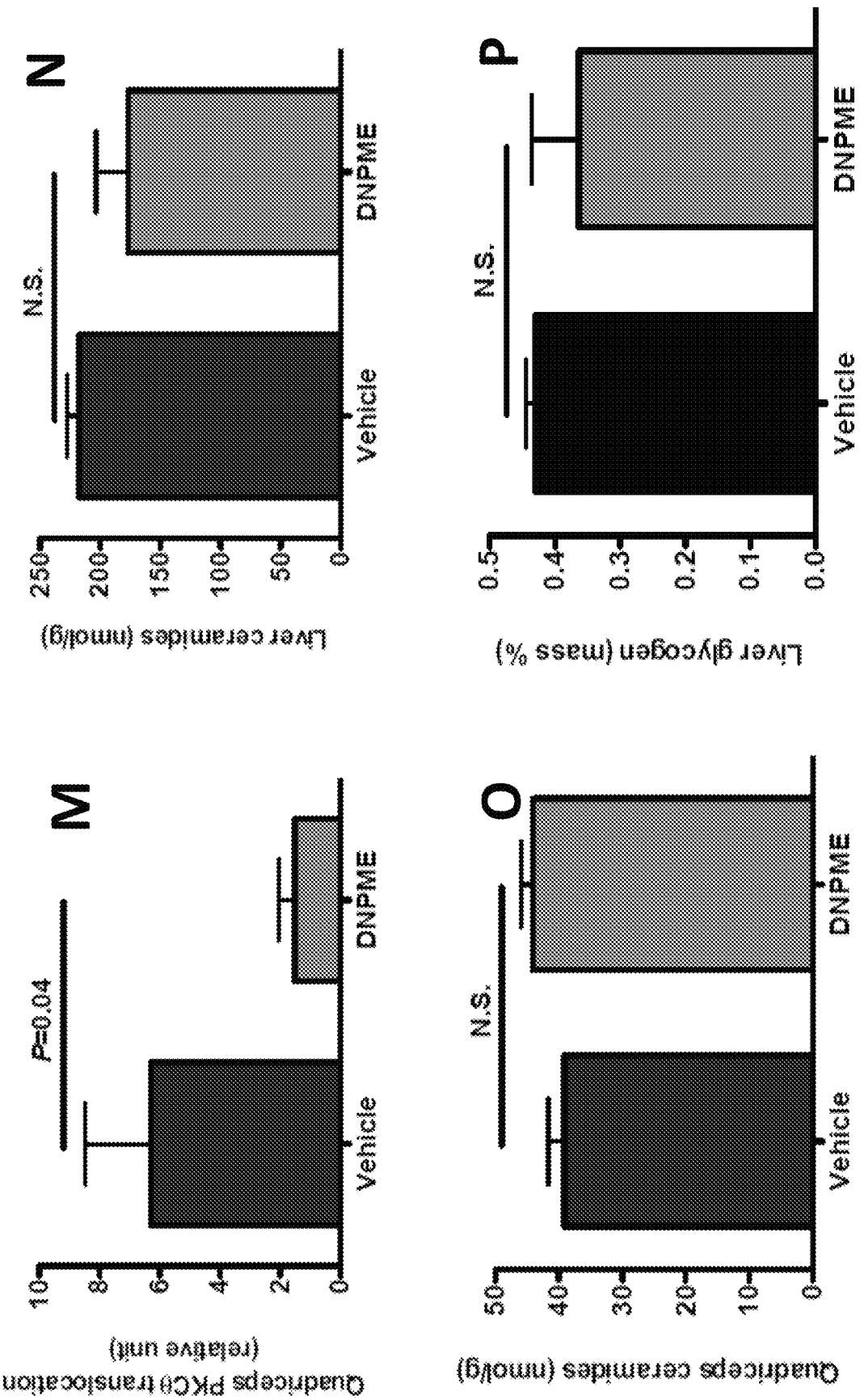
FIG. 6M is a graph illustrating quadriceps PKCθ translocation (n=10 per group).
FIG. 6N is a graph illustrating liver ceramide content.
FIG. 6O is a graph illustrating muscle ceramide content.
FIG. 6P is a graph illustrating liver glycogen content.
Figures 6Q, 6R, 6S, 6T:
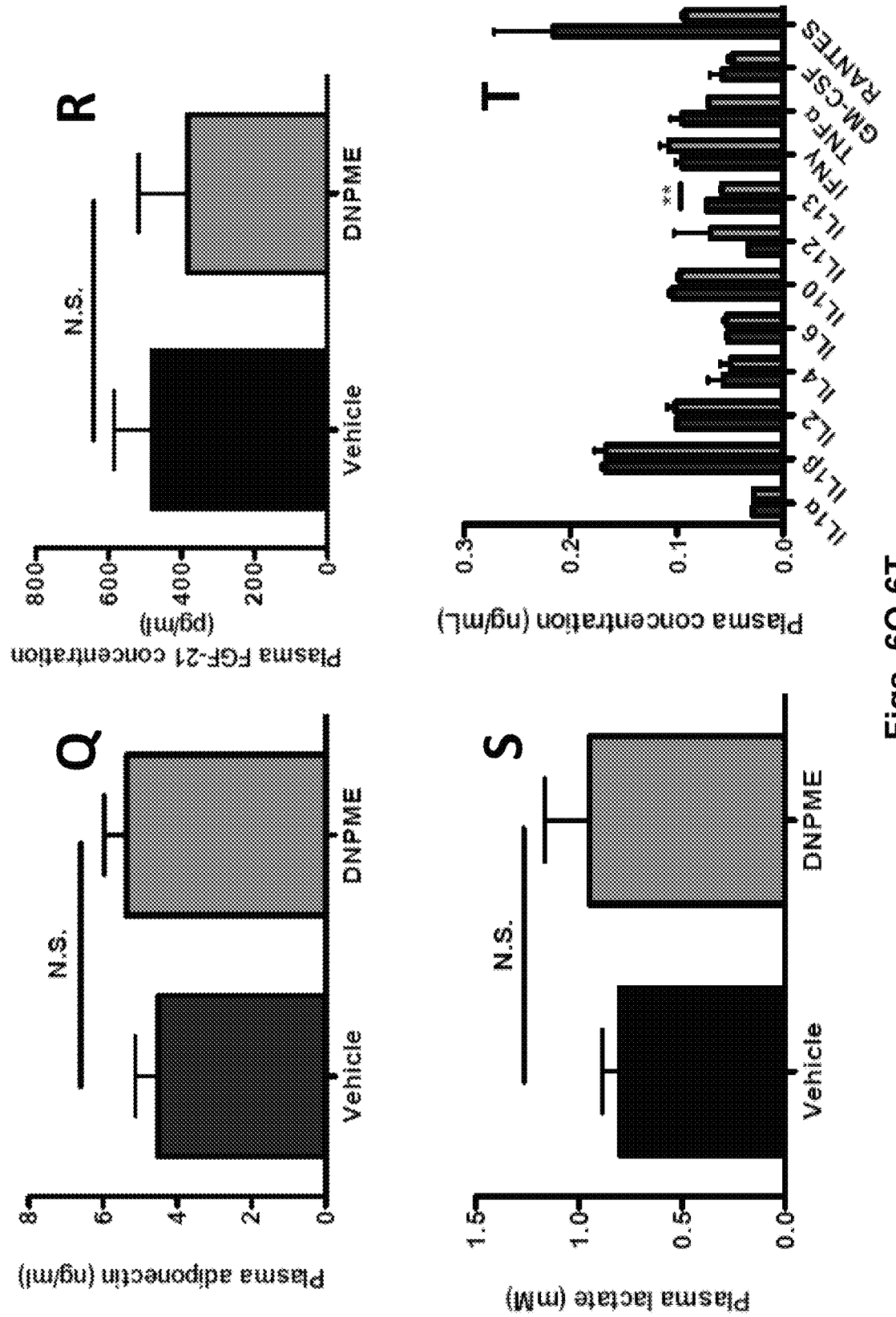
FIG. 6Q is a graph illustrating plasma adiponectin concentration.
FIG. 6R is a graph illustrating plasma FGF-21 concentration.
FIG. 6S is a graph illustrating plasma concentration of inflammatory markers; n=3 per group.
Figures 7A, 7B, 7C, 7D:
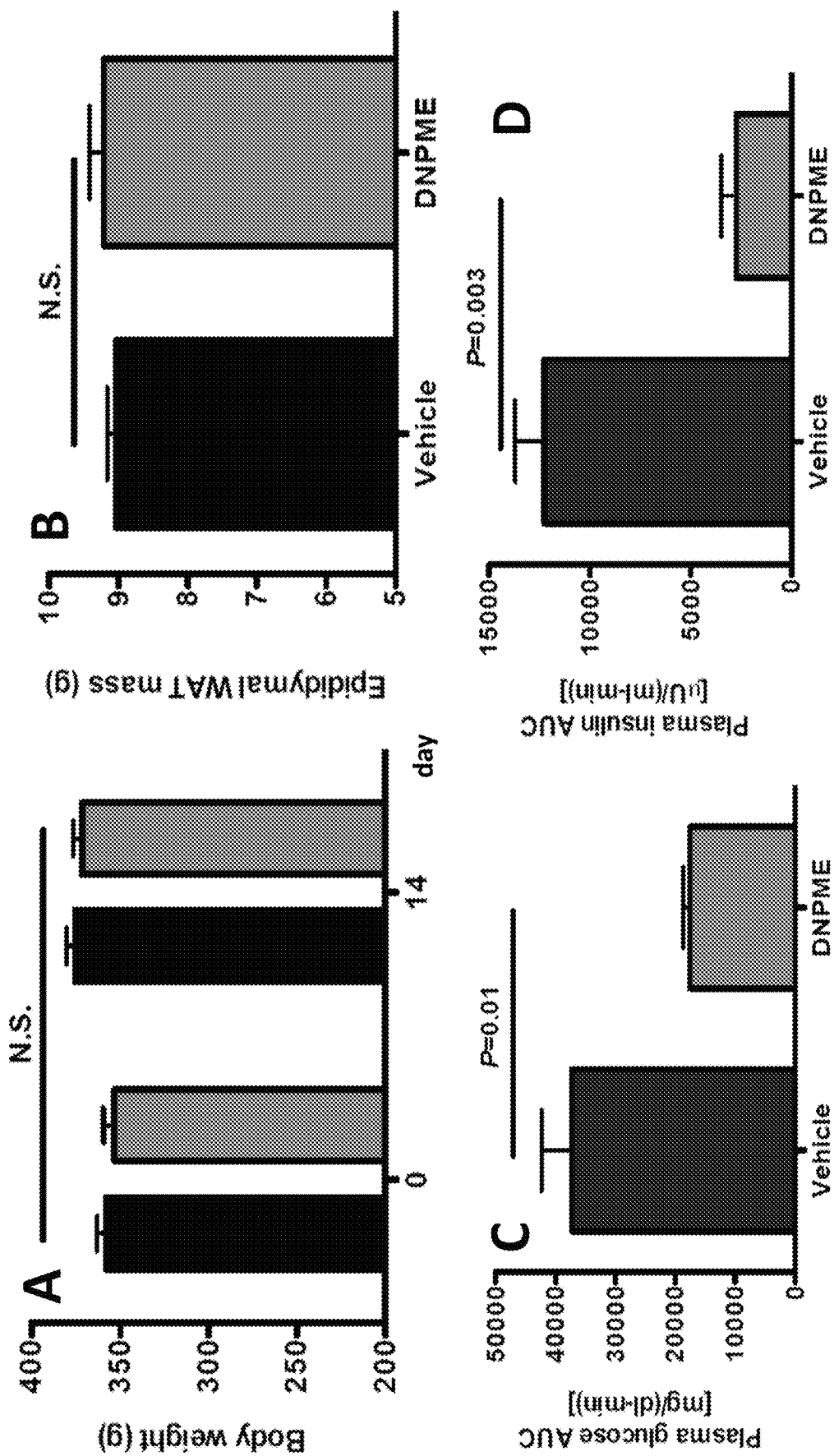
FIGS. 7A-7O, illustrates the finding that 14 days of DNPME treatment reverses hyperglycemia and glucose intolerance in rat models of type 2 diabetes (T2D).
FIG. 7B is a graph illustrating WAT weight in an intraperitoneal glucose tolerance test.
FIG. 7C is a graph illustrating insulin area under the curve in an intraperitoneal glucose tolerance test.
FIG. 7D is a graph illustrating glucose area under the curve in an intraperitoneal glucose tolerance test. For FIGS. 7A-7D, rats were treated with low dose streptozotocin treatment and 3-day high fat feeding; n=5-7 per group.
Figures 7I, 7J, 7K, 7L:
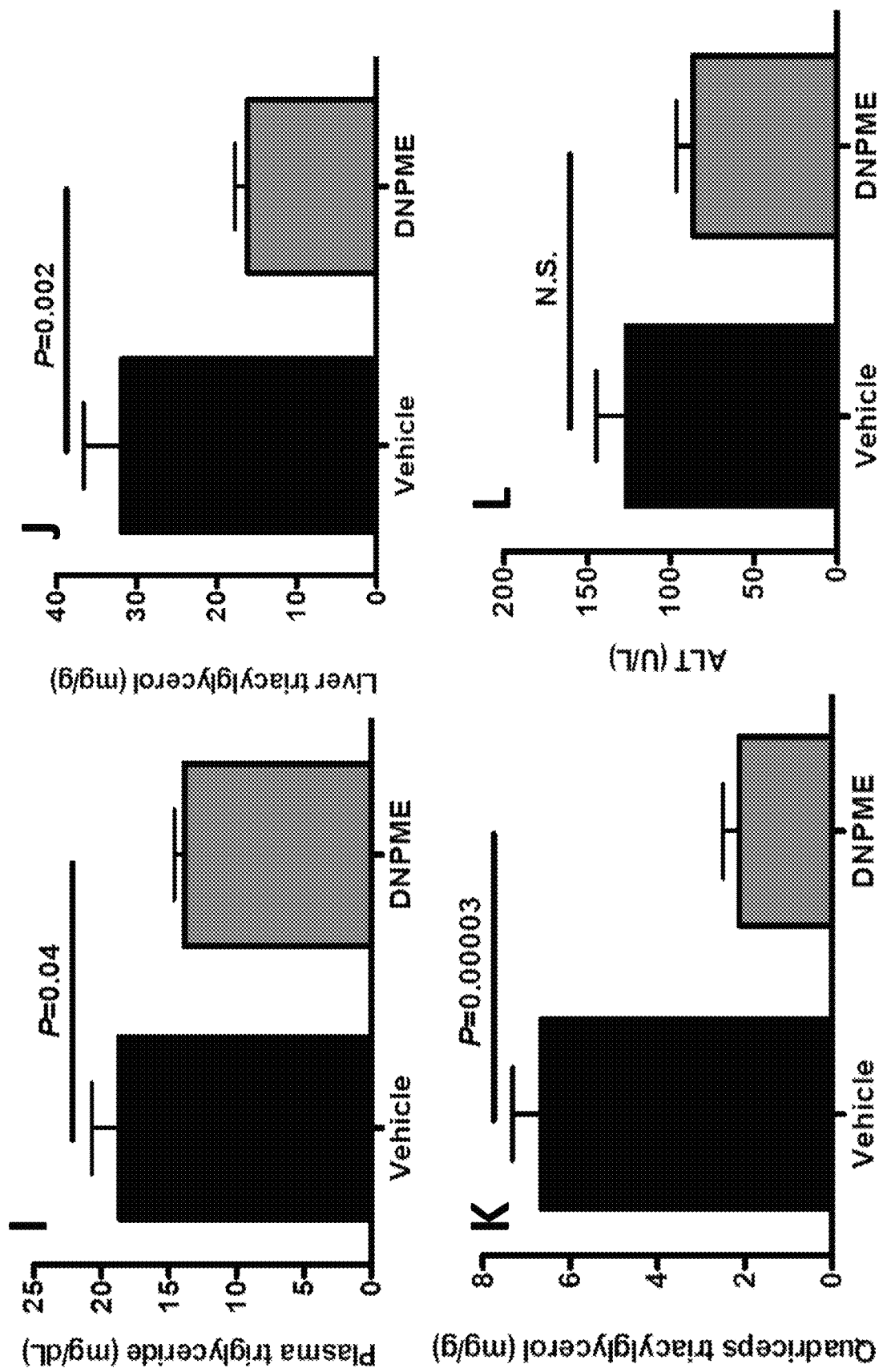
FIG. 7I is a graph illustrating triglycerides in Zucker Diabetic Fatty rats.
FIG. 7J is a graph illustrating liver triglycerides in Zucker Diabetic Fatty rats.
FIG. 7K is a graph illustrating quadriceps triglycerides in Zucker Diabetic Fatty rats.
FIG. 7L is a graph illustrating plasma ALT in Zucker Diabetic Fatty rats.
Figure 7M:
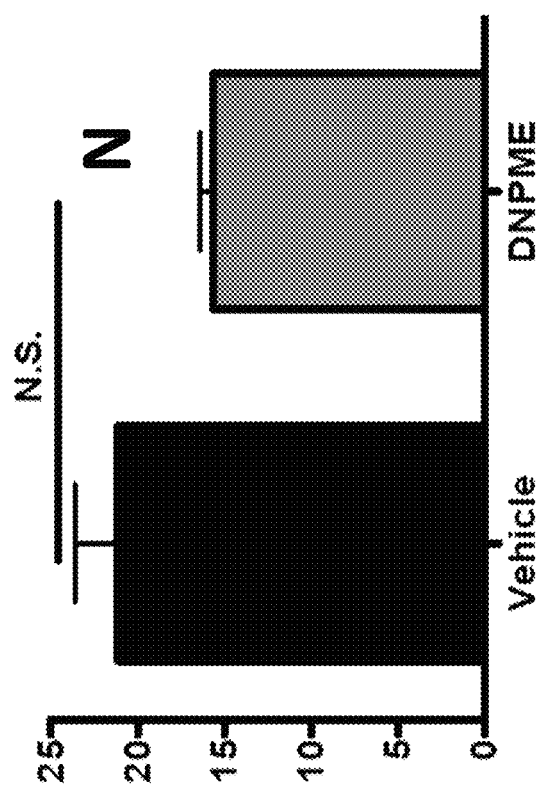
FIG. 7M is a graph illustrating AST in Zucker Diabetic Fatty rats.
Figure 7N:
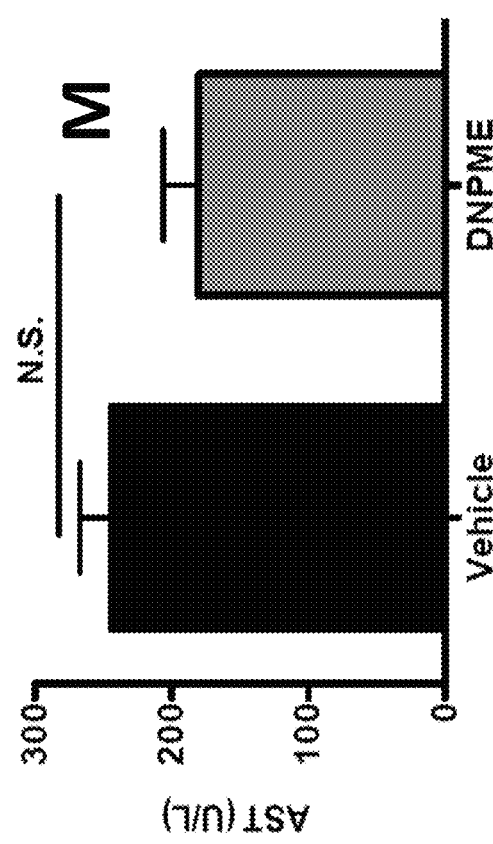
FIG. 7N is a graph illustrating BUN in Zucker Diabetic Fatty rats.
Figure 7O:
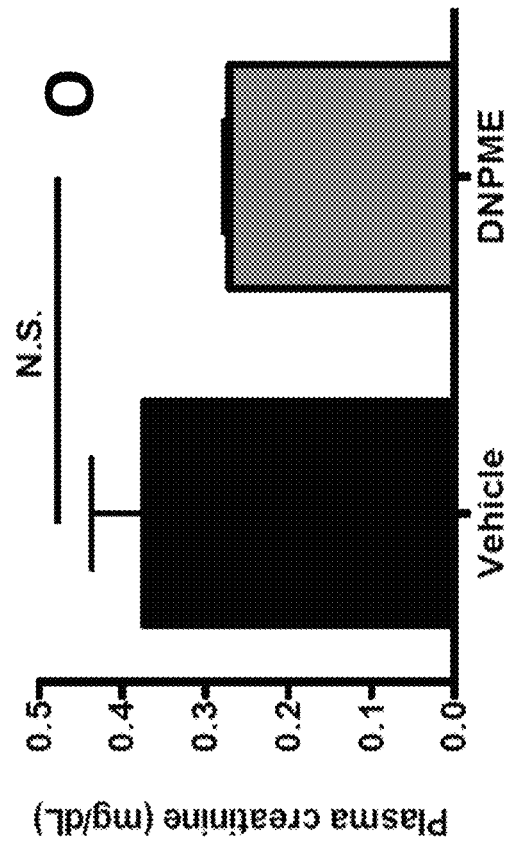

The striking safety and efficacy profiles of DNPME led to the examination of whether DNPME treatment could reverse pre-existing hypertriglyceridemia, hepatic steatosis and insulin resistance in a rat model of NAFLD. To this end, hepatic steatosis was induced in rats by feeding them a high fat diet with sucrose-supplemented drinking water. The rats were then treated with DNPME or vehicle daily for 5 days. The rats treated with DNPME had lower fasting plasma glucose, triglyceride and insulin concentrations compared to the vehicle treated animals (FIGS. 2A-2C), despite identical body weight at the time of study, and identical food intake during the treatment period (FIGS. 6A-6B). Consistent with the reduced fasting plasma glucose and insulin concentrations, DNPME-treated rats had a 20% reduction in basal endogenous glucose production (FIG. 2D). DNPME-treated rats were also much more glucose tolerant as reflected by marked reductions in plasma glucose and insulin concentrations in response to an intraperitoneal glucose tolerance test (FIGS. 2E-F and 6C-6D).

Figures 2I, 2J, 2K, 2L:
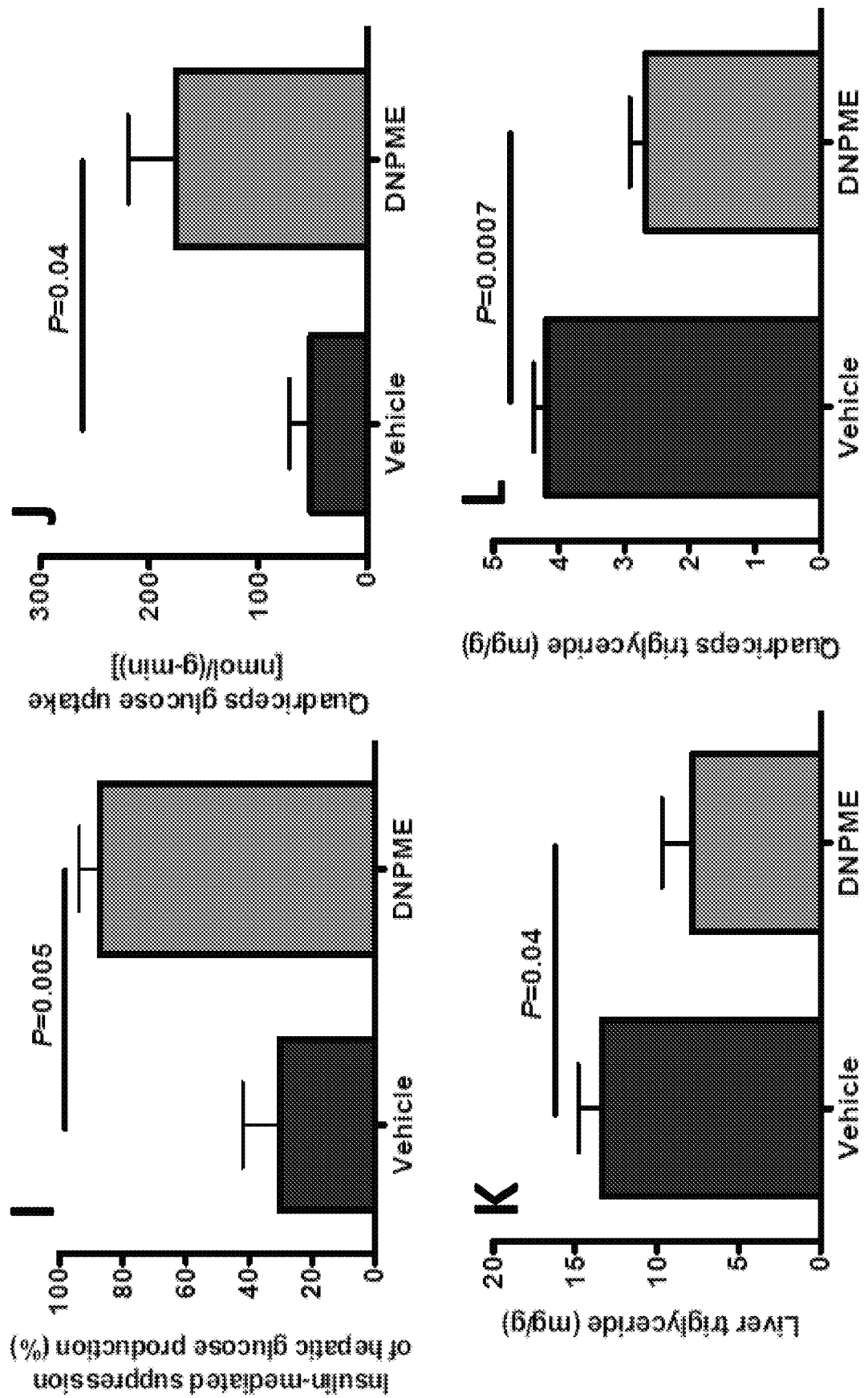
FIG. 2I is a graph illustrating insulin-mediated suppression of hepatic glucose production.
FIG. 2J is a graph illustrating insulin-stimulated glucose uptake in quadriceps.
FIG. 2K is a graph illustrating liver TAG.
FIG. 2L is a graph illustrating quadriceps TAG.

DNPME-treated rats also manifested markedly increased whole body insulin responsiveness as reflected by a greater than three-fold increase in the glucose infusion rate required to maintain euglycemia during the hyperinsulinemic-euglycemic clamp (FIGS. 2G and 6E-6G). Although not wishing to be bound by any particular theory, this increase in whole body glucose insulin responsiveness in the DNPME-treated rats was likely attributed to improvements in both hepatic and peripheral insulin sensitivity (FIGS. 2H-2I). The increased insulin-stimulated peripheral glucose metabolism was associated with a more than two-fold increase in insulin-stimulated glucose uptake in skeletal muscle (FIG. 2J). The marked improvement in hepatic and peripheral insulin sensitivity was associated with 40-50% reductions in liver and muscle TAG (FIGS. 2K-2L) and diacylglycerol (DAG) content (FIGS. 6H-6K). Consistent with the reduced liver and muscle DAG concentration, reduced protein kinase C (PKC)ε and PKCθ translocation were observed in liver and muscle respectively in DNPME-treated rats (FIGS. 6L-6M) (Griffin et al., 1999, Diabetes 48:1270-1274; Yu et al., 2002, J. Biol. Chem. 277:50230-50236, Samuel et al., 2004, J. Biol. Chem. 279:32345-32353; Samuel et al., 2007, J. Clin. Invest. 117:739-745). In contrast there were no observed differences in liver or muscle ceramide content or alterations in plasma pro-gluconeogenic inflammatory cytokine, adiponectin, FGF-21, or lactate concentration in the DNPME control animals despite this marked improvement in insulin sensitivity (FIGS. 6N-6T). The reduced liver lipid content was associated with a 50% reduction in liver TAG export (FIG. 2M), highlighting a causal role for NAFLD in the development of whole-body insulin resistance, and the potential to treat liver and muscle insulin resistance by promoting increased hepatic fat oxidation.

Figures 2M, 2N, 2O:
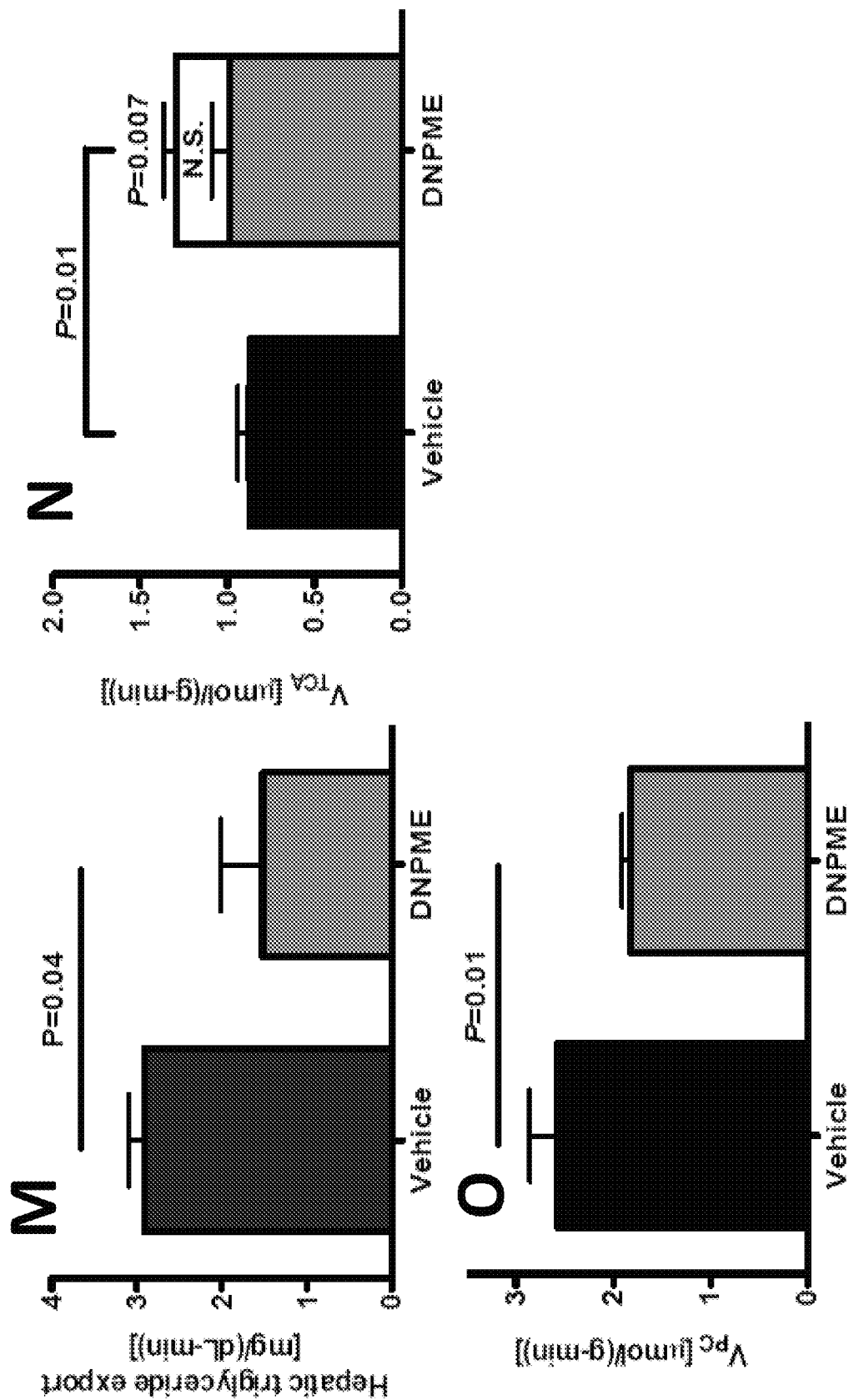
FIG. 2M is a graph illustrating liver VLDL production.
FIG. 2N is a graph illustrating the effect of DNPME on liver TCA cycle flux and substrate contributions to the TCA cycle.

In order to determine if DNPME reduced hepatic lipid content and VLDL production by promoting increased hepatic mitochondrial uncoupling in vivo, liver-specific rates of oxidative flux pathways were measured, and a 50% increase in rates of hepatic TCA flux was observed (FIG. 2N). Consistent with the reduced basal glucose production and fasting plasma glucose concentrations measured in DNPME treated rats, these animals also exhibited a 30% reduction in hepatic pyruvate carboxylase flux (FIG. 2O).

DNPME Studies in Rat Model of Type II Diabetes

Given the profound effects of DNPME to reduce ectopic lipid content in liver and skeletal muscle and improve whole body insulin sensitivity in both the NAFLD prevention and reversal studies, it was examined whether DNPME treatment would improve fasting and postprandial plasma glucose and insulin profiles in a rat model of T2D. The effect of 14 days of DNPME vs. vehicle treatment in a well-established rat model of T2D was examined (Masiello et al., 1998, Diabetes 47:224-229; Reed et al., 2000, Metab. Clin. Exp. 49:1390-1394; Samuel et al., 2009, Proc. Natl. Acad. Sci. USA 106:12121-12126; Samuel et al., 2004, J. Biol. Chem. 279:32345-32353).

Figures 3E, 3F, 3G:
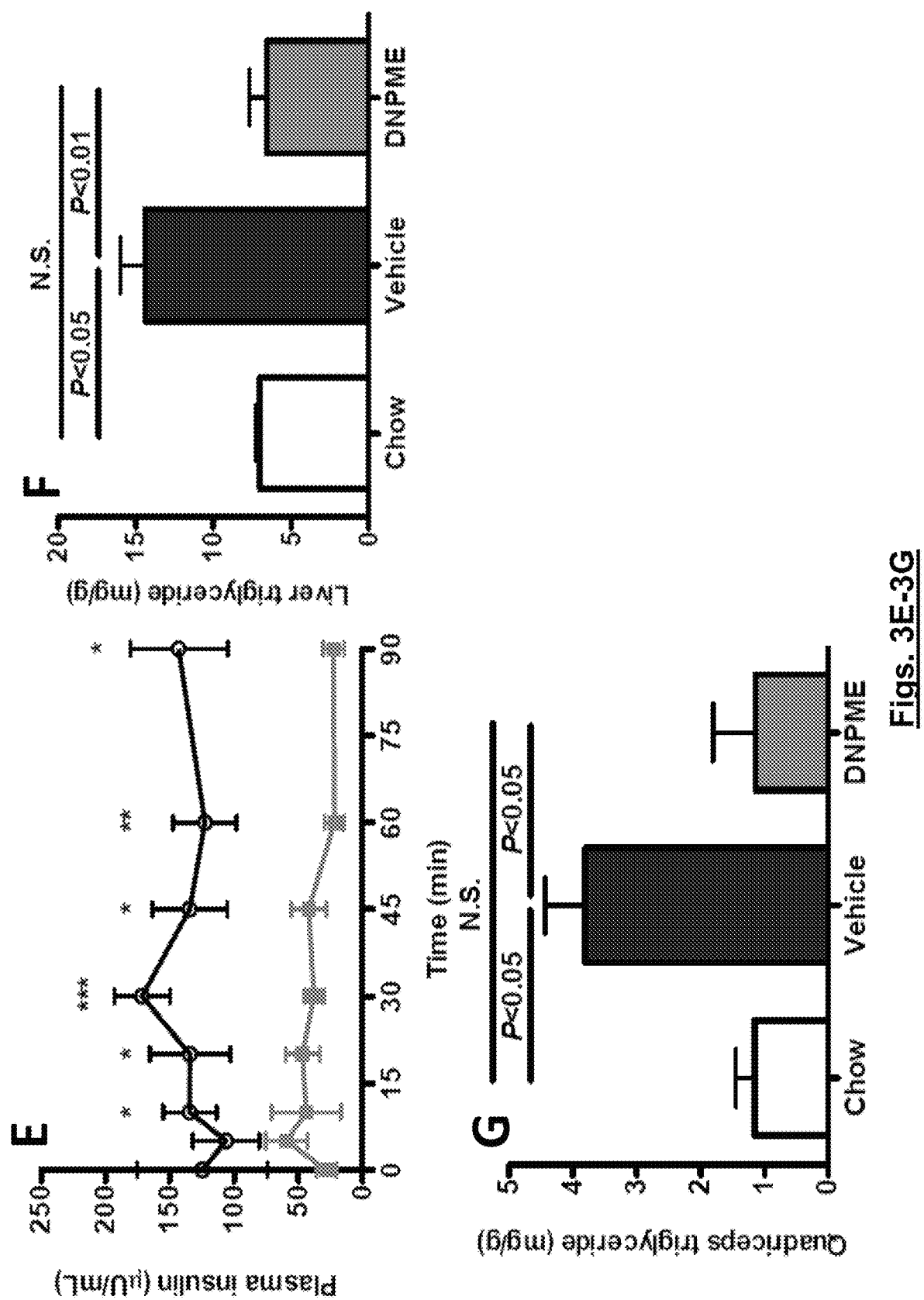
Figure 5F:
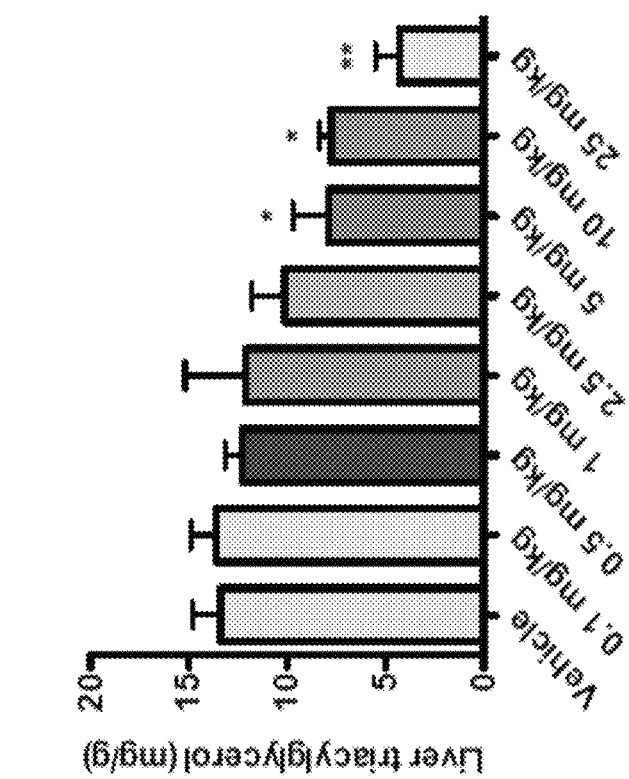
Figure 5G:
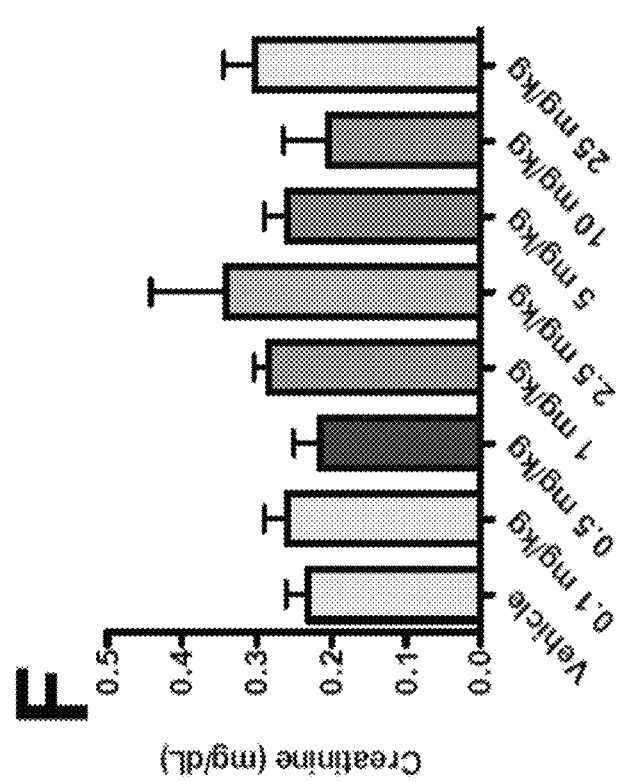
Figures 5H, 5I:
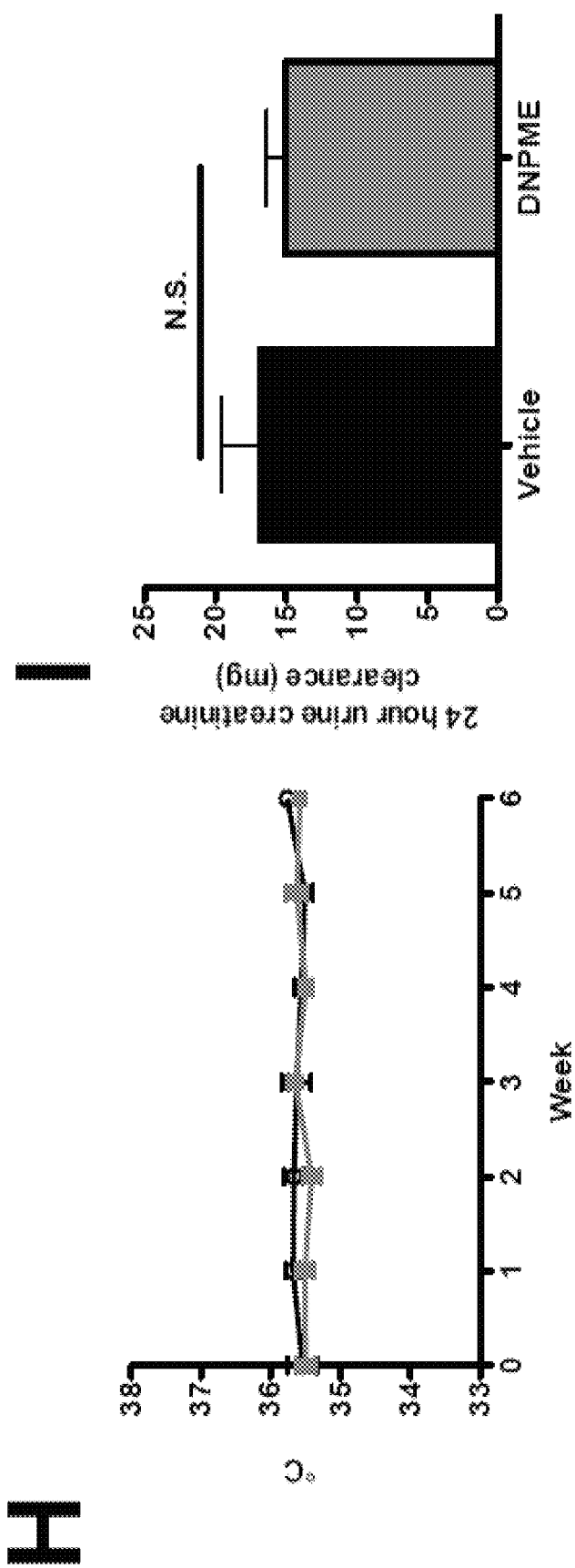

Despite having no difference in body weight or white adipose tissue weight, and consistent with a primarily hepatic uncoupling effect and unchanged whole-body metabolism, DNPME treatment normalized fasting plasma glucose and triglyceride concentrations (FIGS. 3A-3C). DNPME treatment also resulted in a marked improvement in glucose tolerance, reflecting improved whole-body insulin sensitivity (FIGS. 3D-3E, 7C-7D). Finally, and consistent with the results in the other insulin resistant rodent models of NAFLD, DNPME treatment caused a marked reduction in both liver and muscle TAG content (FIGS. 3F-3G) without any indication of renal or hepatic histopathology (FIGS. 5E-5F). To further test the hypothesis that DNPME treatment ameliorates hyperglycemia in a rat model of chronic type 2 diabetes, 5 day treatment studies on Zucker Diabetic Fatty (ZDF) rats concurrently fed high fat diet and sucrose water were performed. Similar to the results in the T2D model previously described elsewhere herein, DNPME treatment resulted in reductions in fasting plasma glucose, insulin and liver triglyceride concentrations with no indication of liver or renal dysfunction (FIGS. 7G-7O).

Metabolic Cage Studies

Figure 8A:
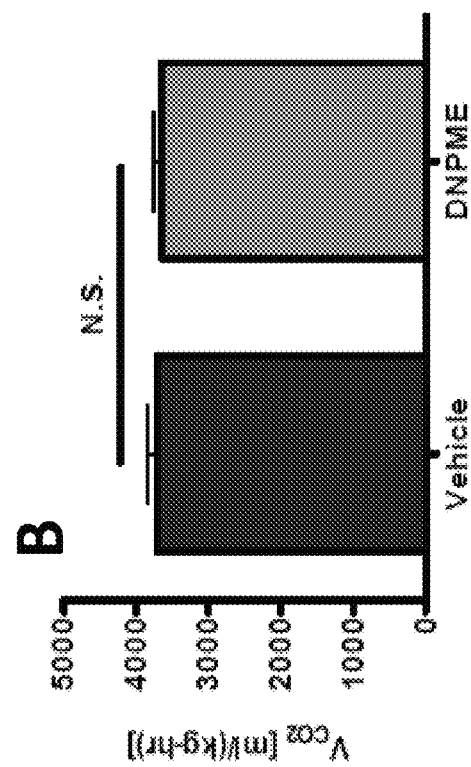
FIGS. 8A-8R, illustrates basal metabolism in DNPME treated mice and in 5 day DNPME-treated rats in vitro.
Figure 8B:
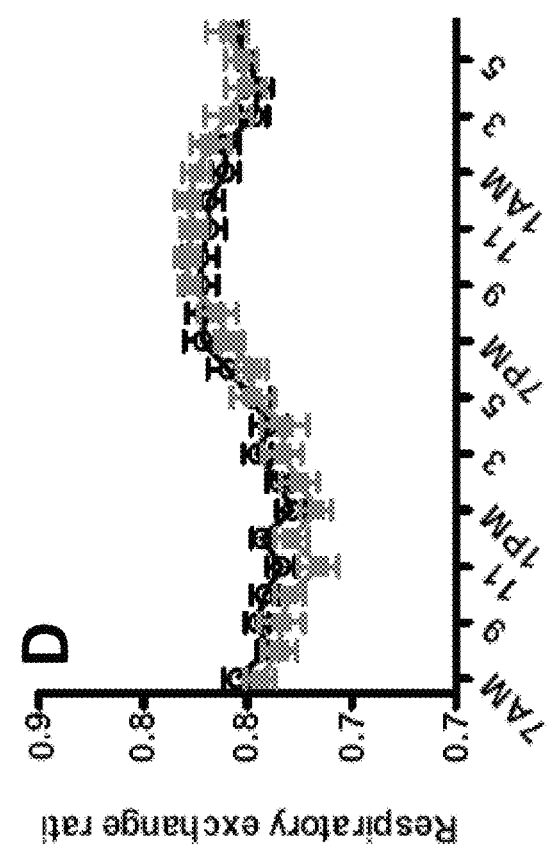
FIG. 8B is a graph illustrating carbon dioxide production.
Figure 8C:
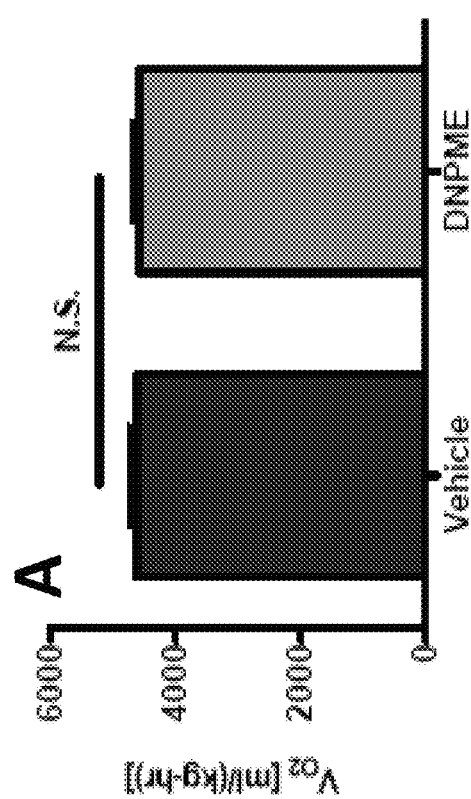
FIG. 8C is a graph illustrating energy expenditure throughout the day.
Figure 8D:
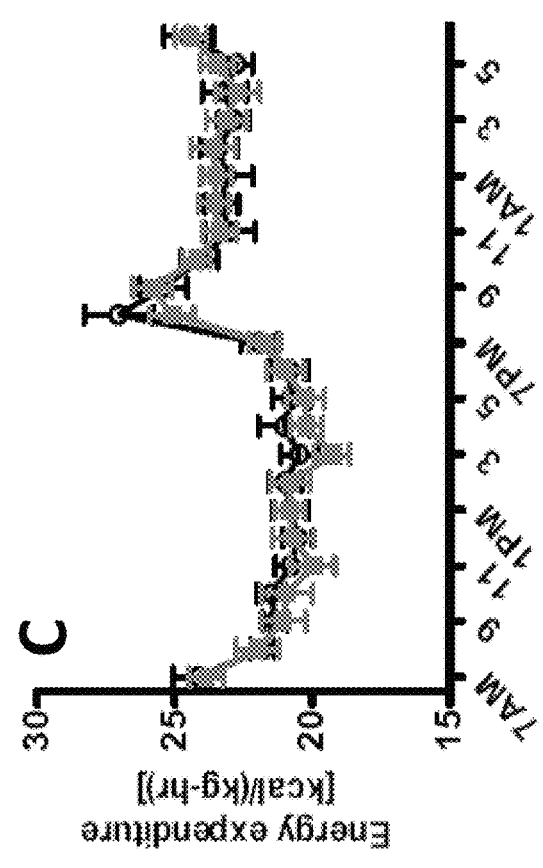
FIG. 8D is a graph illustrating respiratory exchange ratio throughout the day.
Figure 8E:
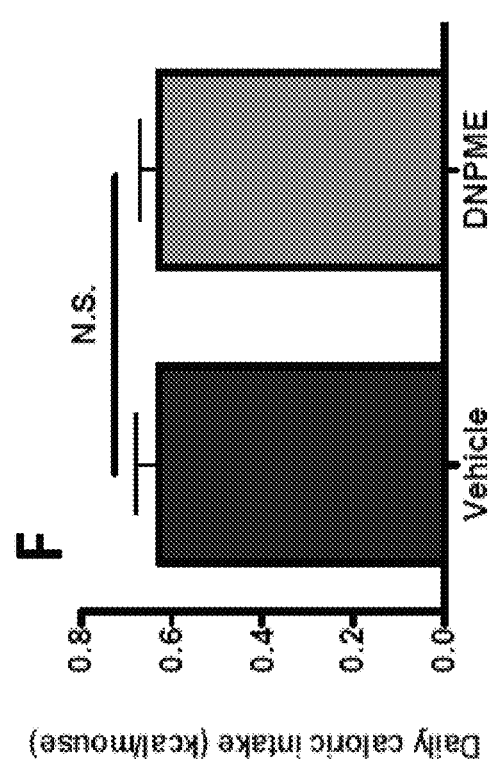
FIG. 8E is a graph illustrating activity throughout the day.
Figure 8F:
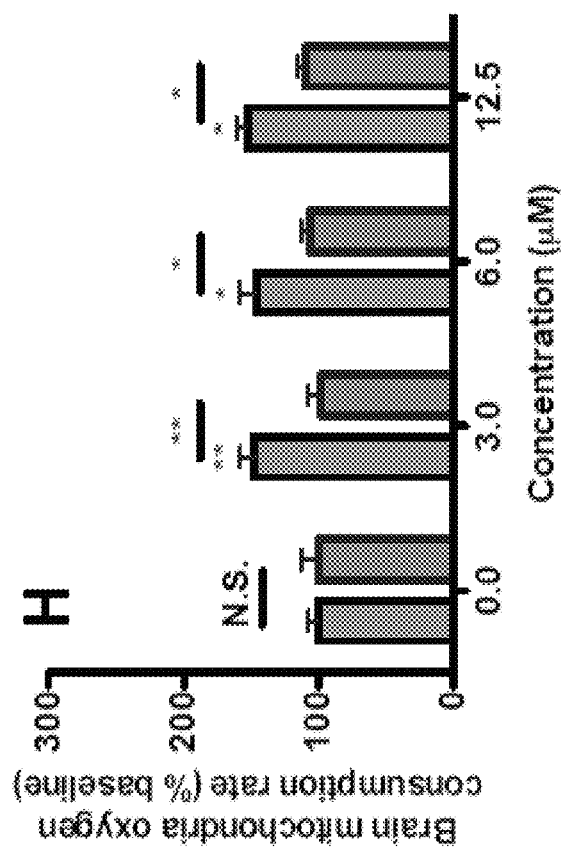
FIG. 8F is a graph illustrating daily caloric intake. For FIGS. 8C-8E: black circles=vehicle treated, red/gray squares=DNPME treated. For FIGS. 8A-8F, n=8 per group.
Figure 8G:
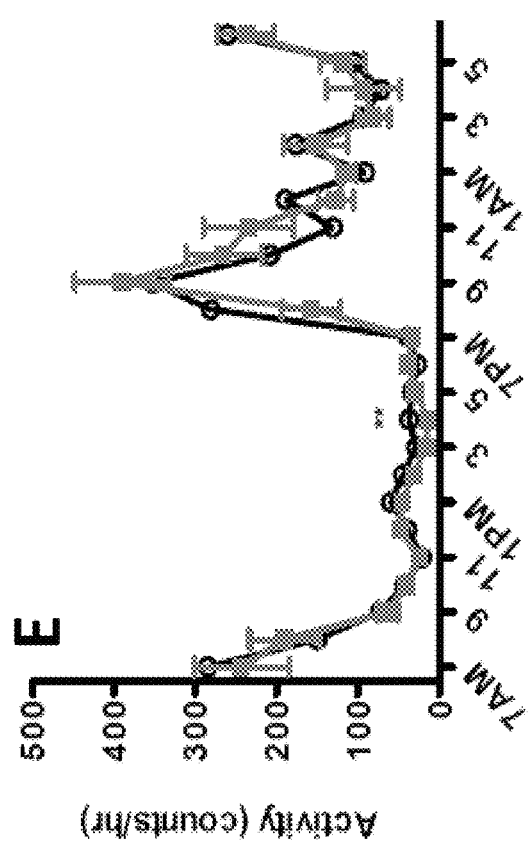
FIGS. 8G-8K are a series of graphs illustrating oxygen consumption rate in isolated mitochondria obtained from liver (FIG. 8G), brain (FIG. 8H), heart (FIG. 8I), quadriceps (FIG. 8J), and kidney (FIG. 8K) after the addition of varying doses of DNP (blue/light gray) or DNPME (red/dark gray). Statistics over individual bars refer to differences from oxygen consumption rate at 0 µM by 2-tailed paired t-test. If statistics are not listed over certain bars, there was no significant difference from 0 µM. In all panels, *P<0.05, **P<0.01.
Figure 8H:
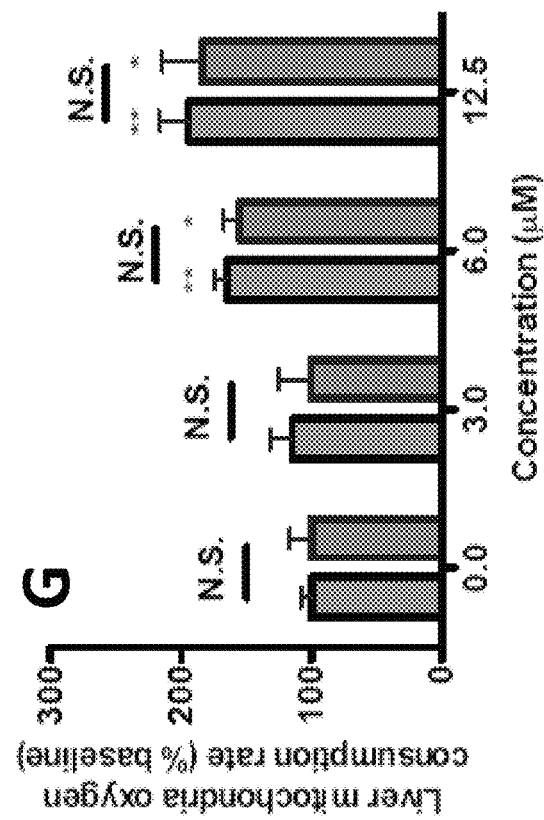
Figures 8I, 8J, 8K, 8L:
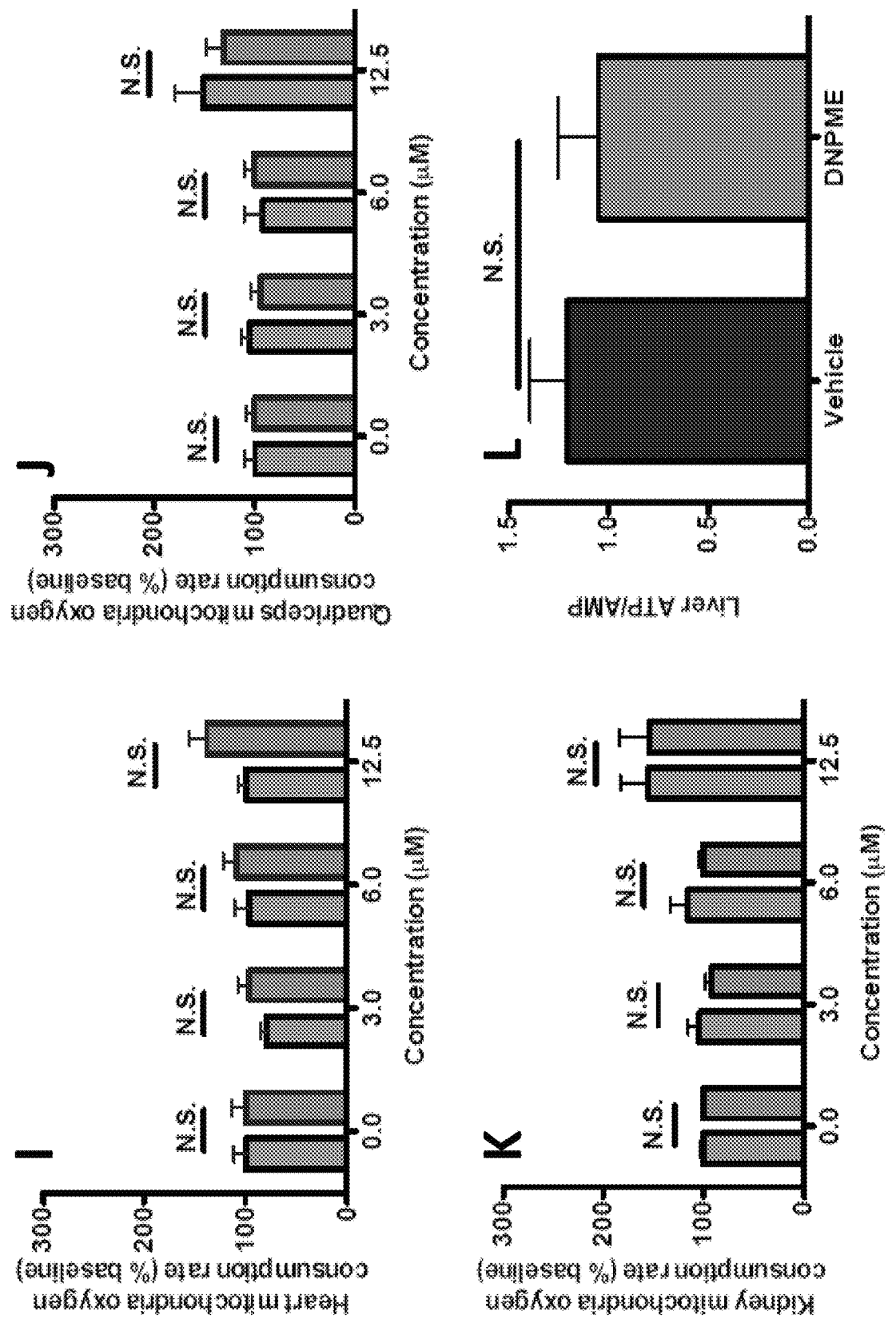
FIG. 8L is a graph illustrating liver ATP/AMP.
Figures 8M, 8N, 8O, 8P:
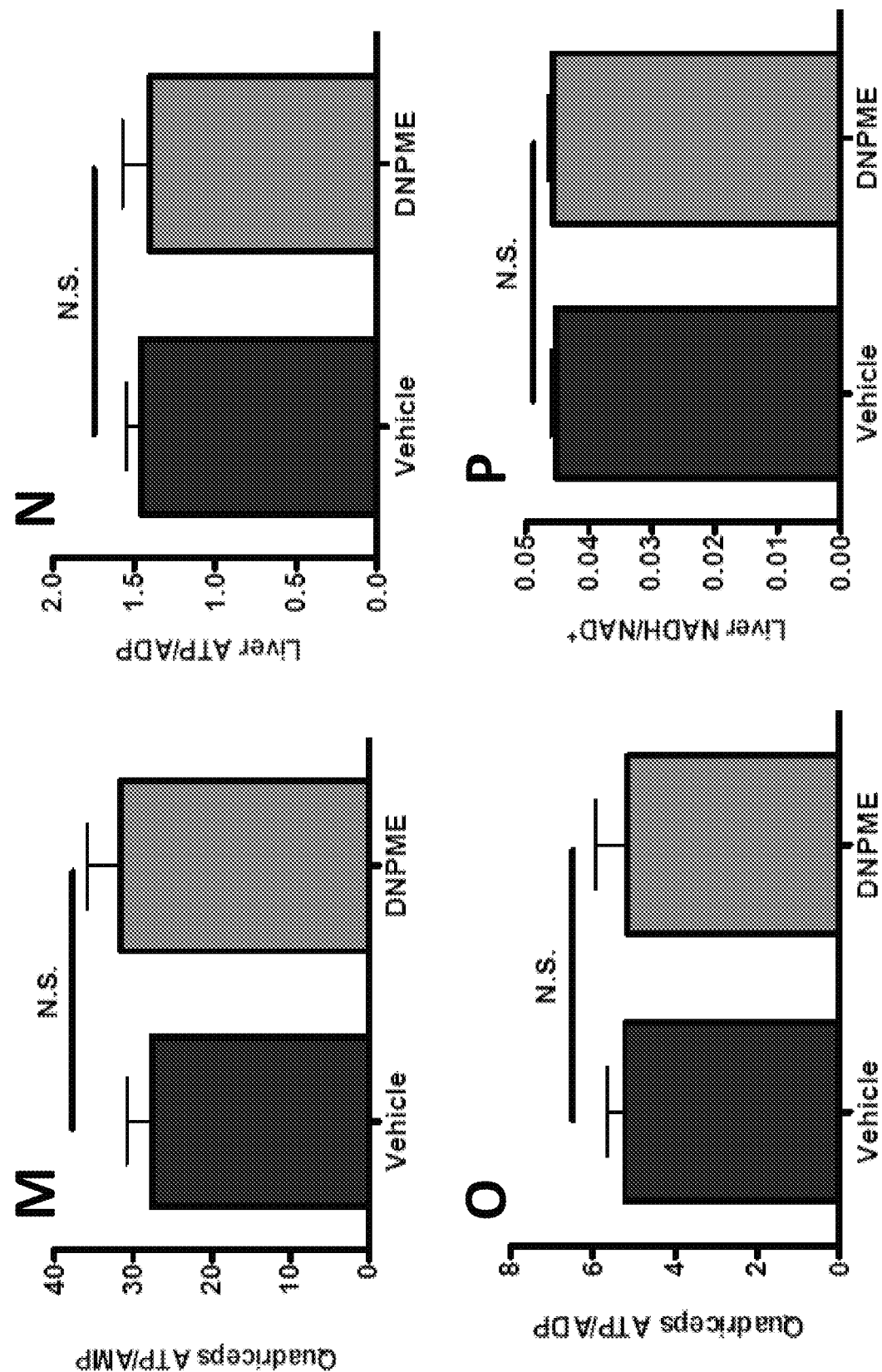
FIG. 8M is a graph illustrating quadriceps ATP/AMP.
FIG. 8N is a graph illustrating liver ATP/ADP.
FIG. 8O is a graph illustrating quadriceps ATP/ADP.
FIG. 8P is a graph illustrating liver NADH/NAD$^+$.
Figures 8Q, 8R:
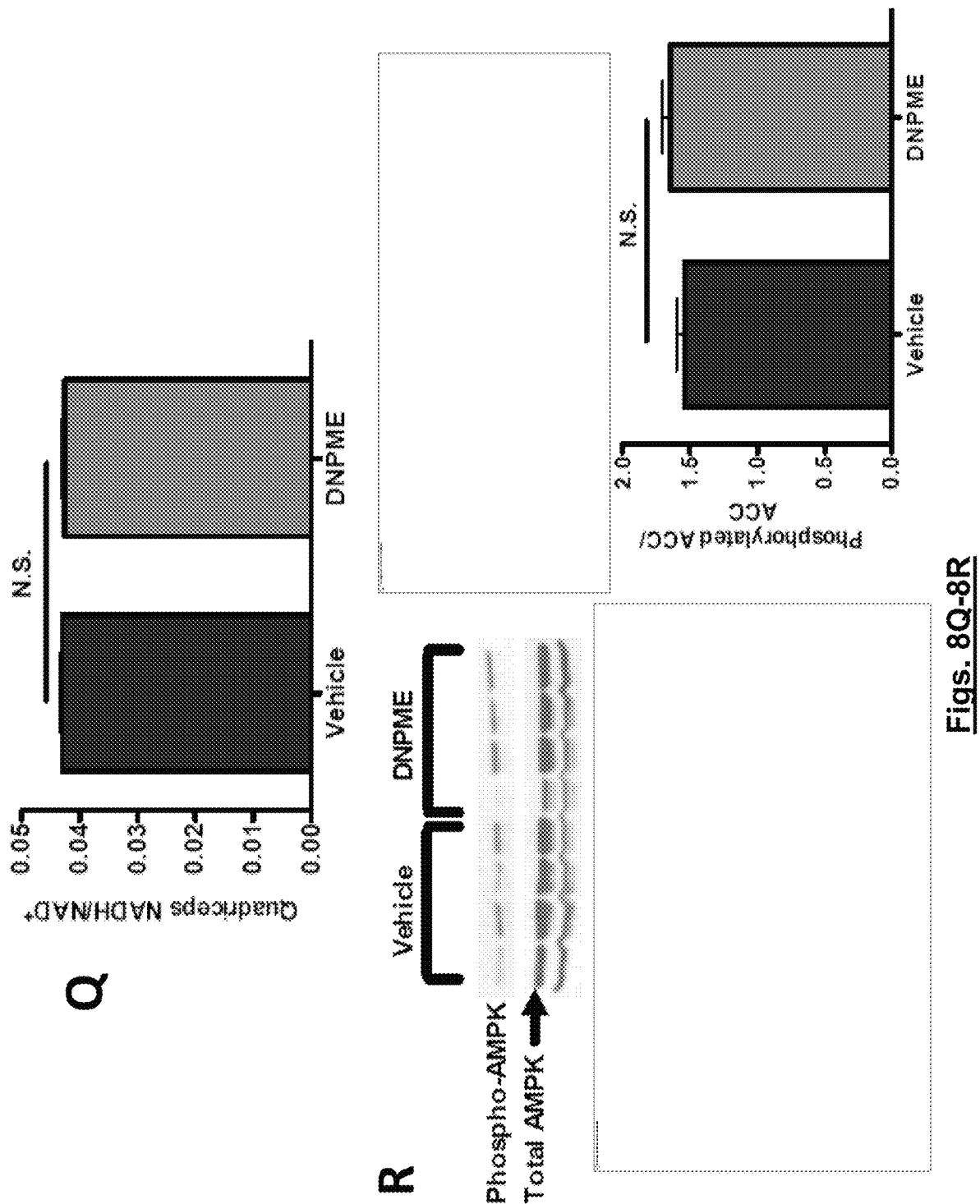
FIG. 8Q is a graph illustrating quadriceps NADH/NAD$^+$.
Figure 9:
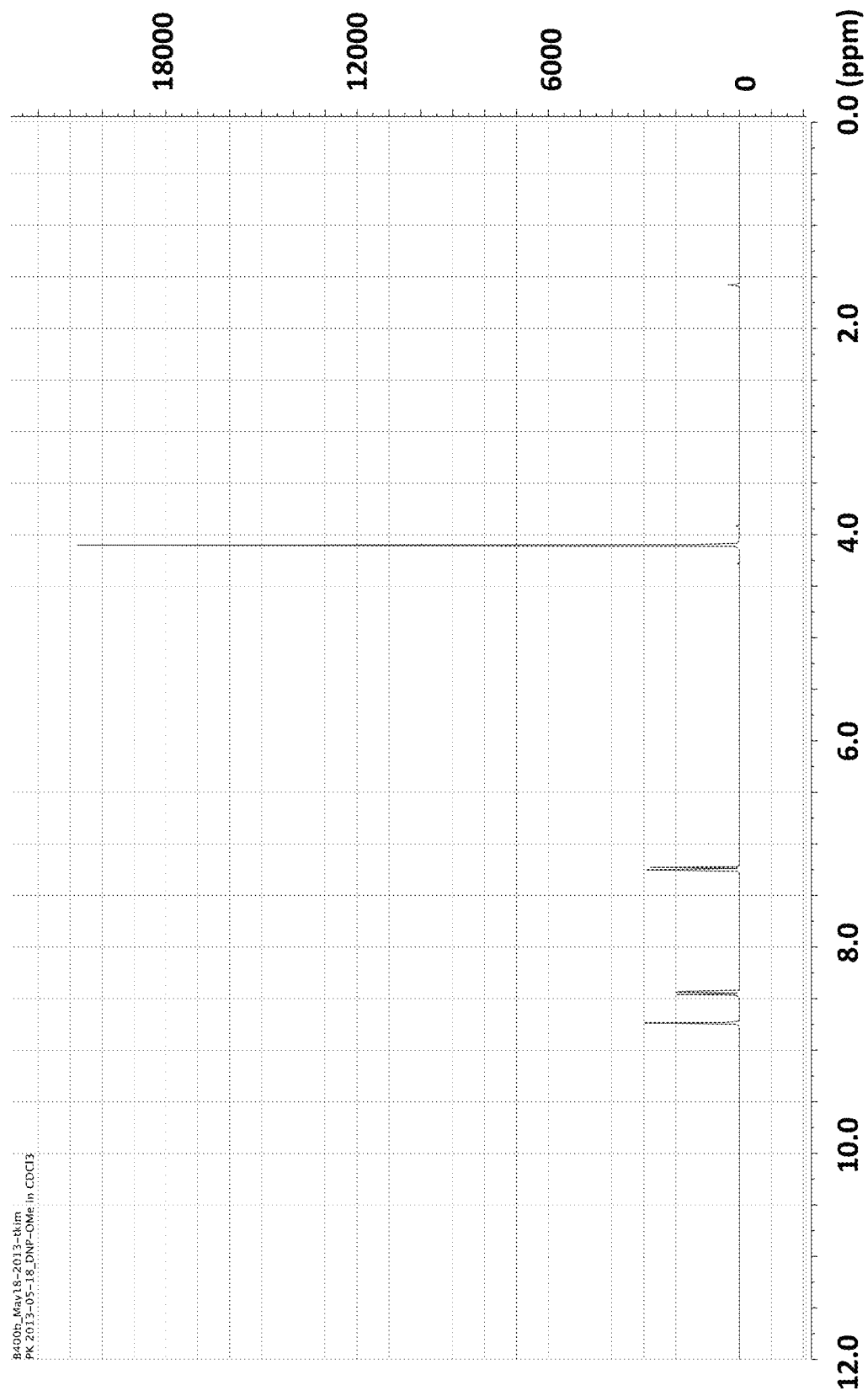
FIG. 9 illustrates the $^1$H NMR spectrum of DNPME (compound 2) in $CDCl_3$.
Figure 10:
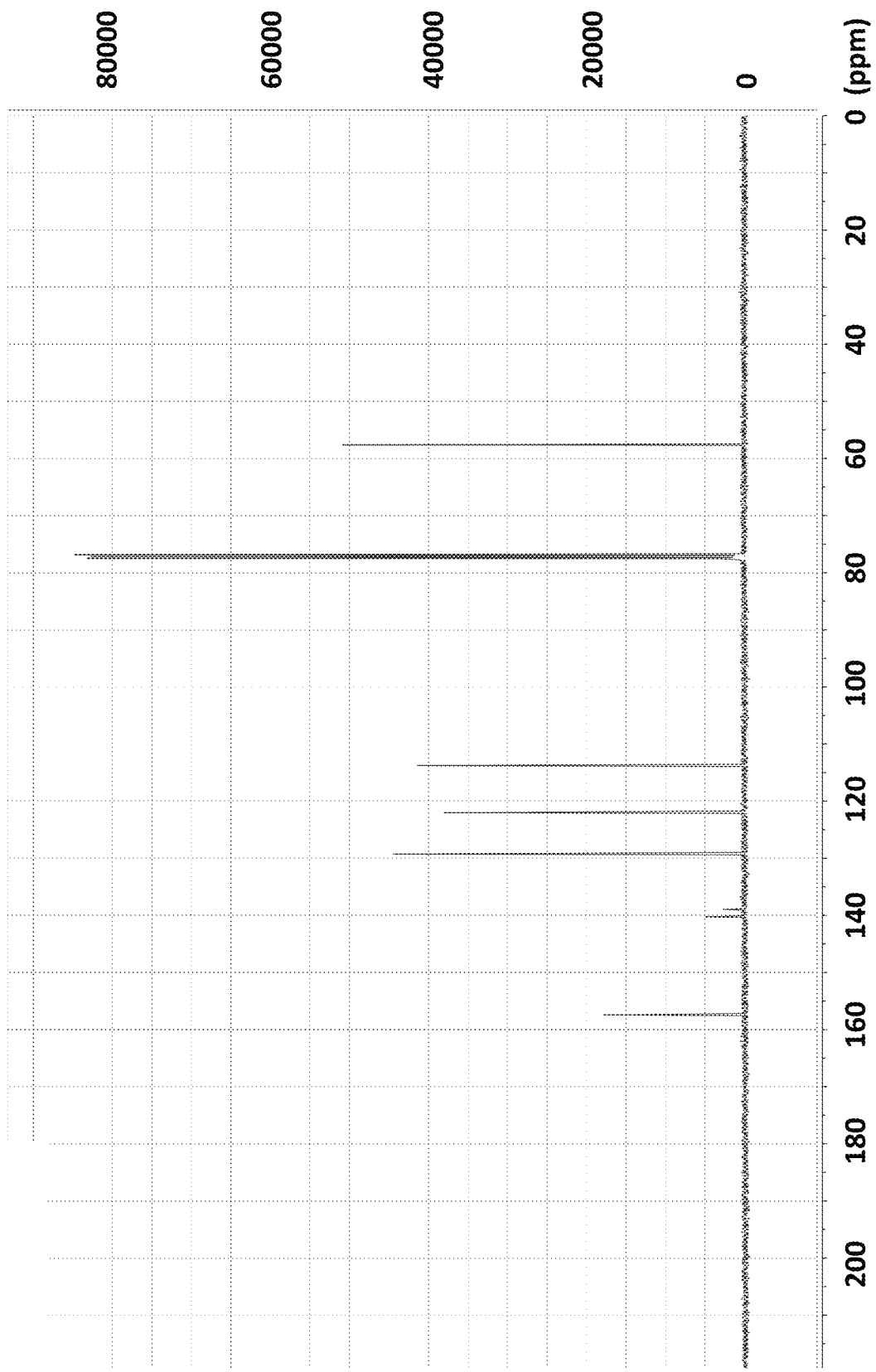
FIG. 10 illustrates the $^{13}$C NMR spectrum of DNPME (compound 2) in $CDCl_3$.
Figure 11:
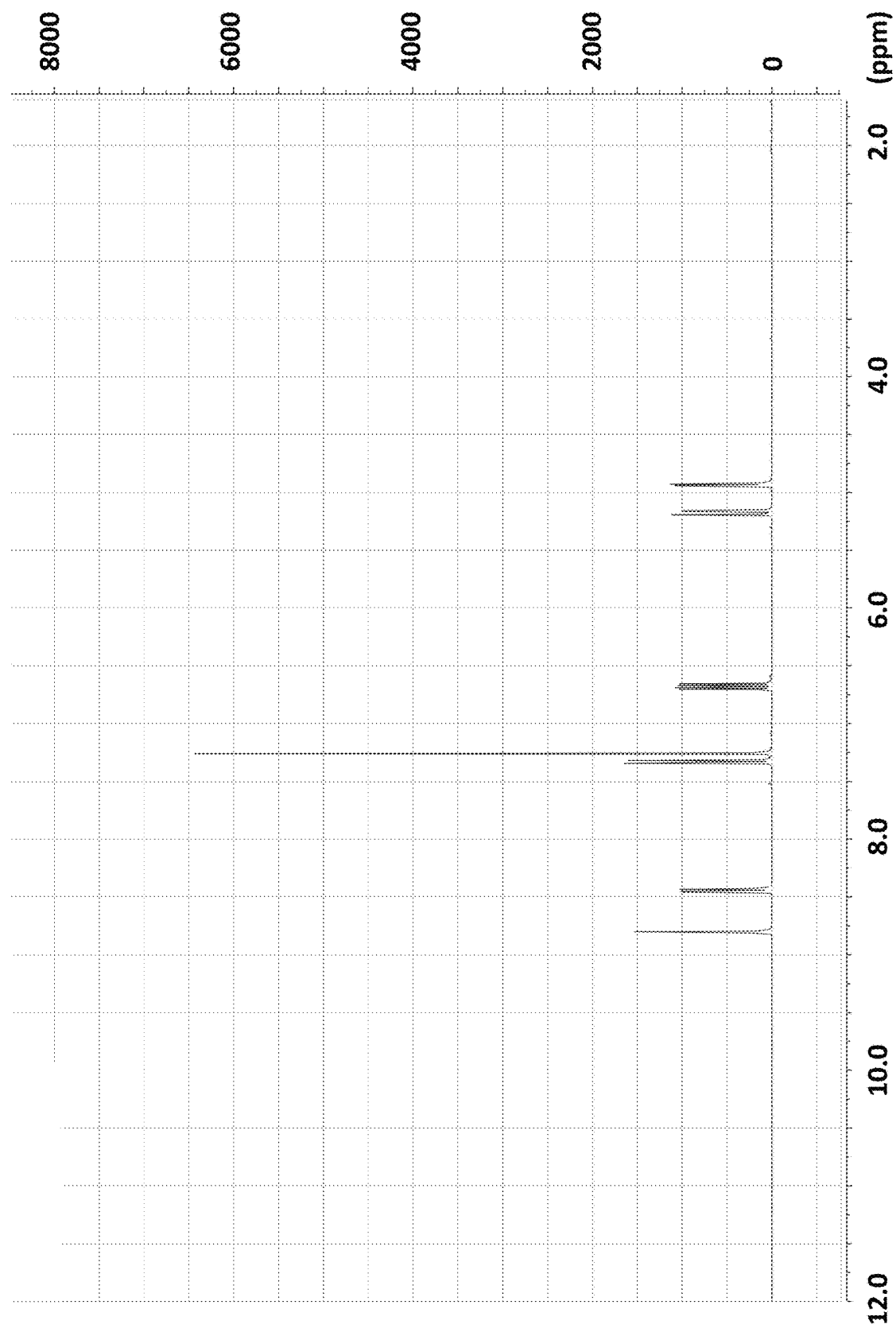
FIG. 11 illustrates the 1H NMR spectrum of DNPVE (compound 6) in $CDCl_3$.
Figure 12:
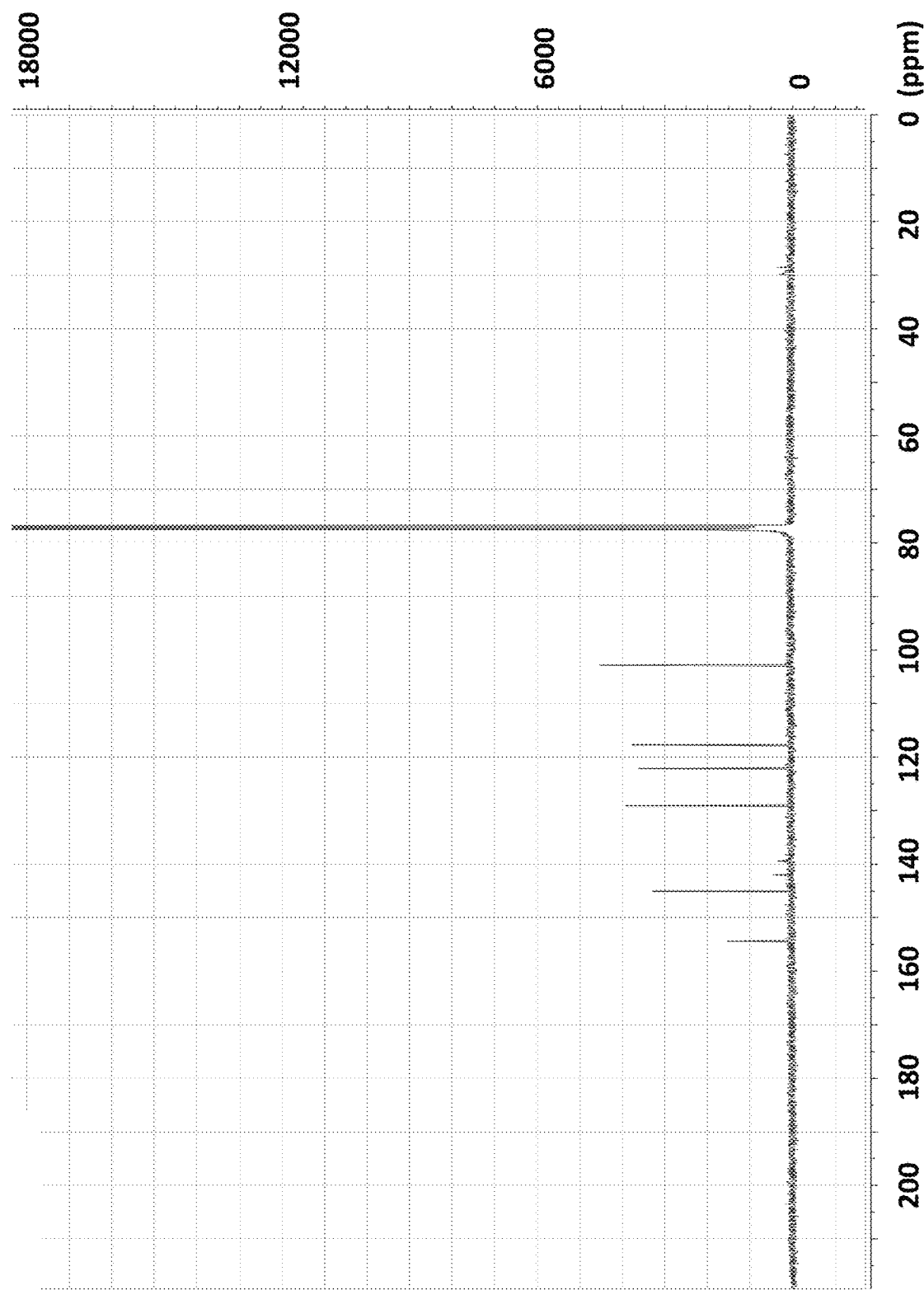
FIG. 12 illustrates the $^{13}$C NMR spectrum of DNPVE (compound 6) in $CDCl_3$.
Figure 13:
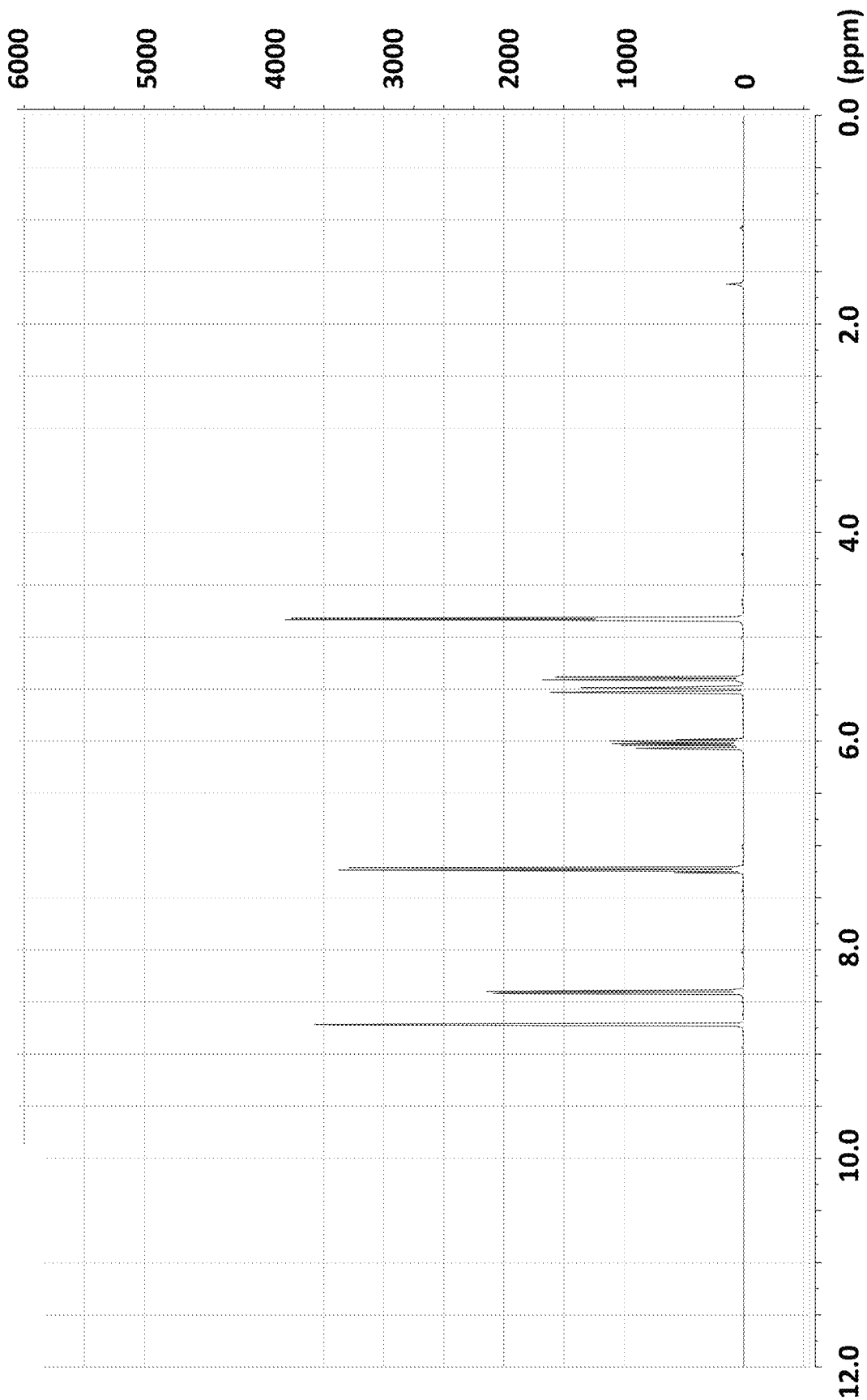
FIG. 13 illustrates the $^1$H NMR spectrum of DNPAE (compound 7) in $CDCl_3$.
Figure 14:
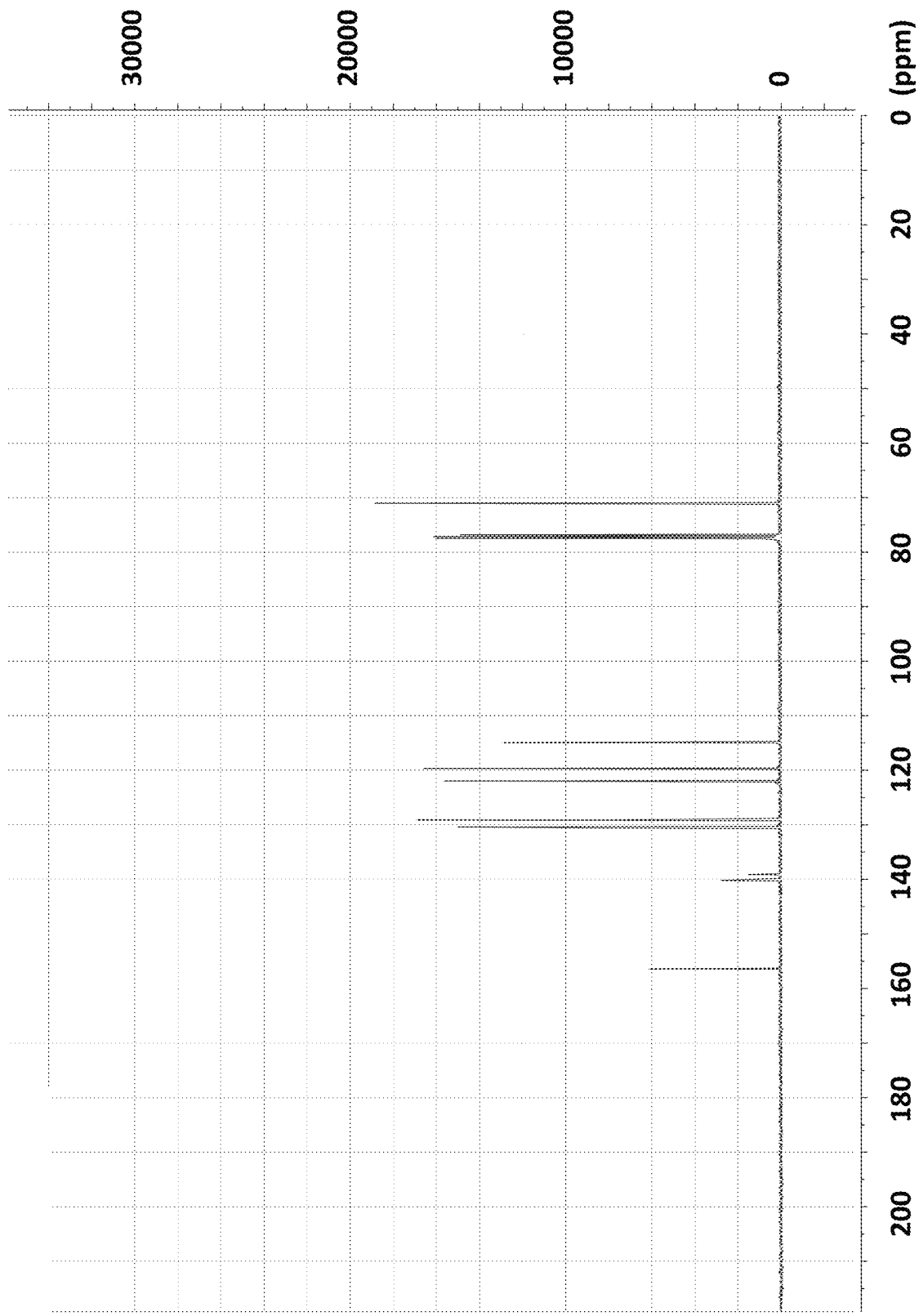
FIG. 14 illustrates the $^{13}$C NMR spectrum of DNPAE (compound 7) in $CDCl_3$.
Figure 15:
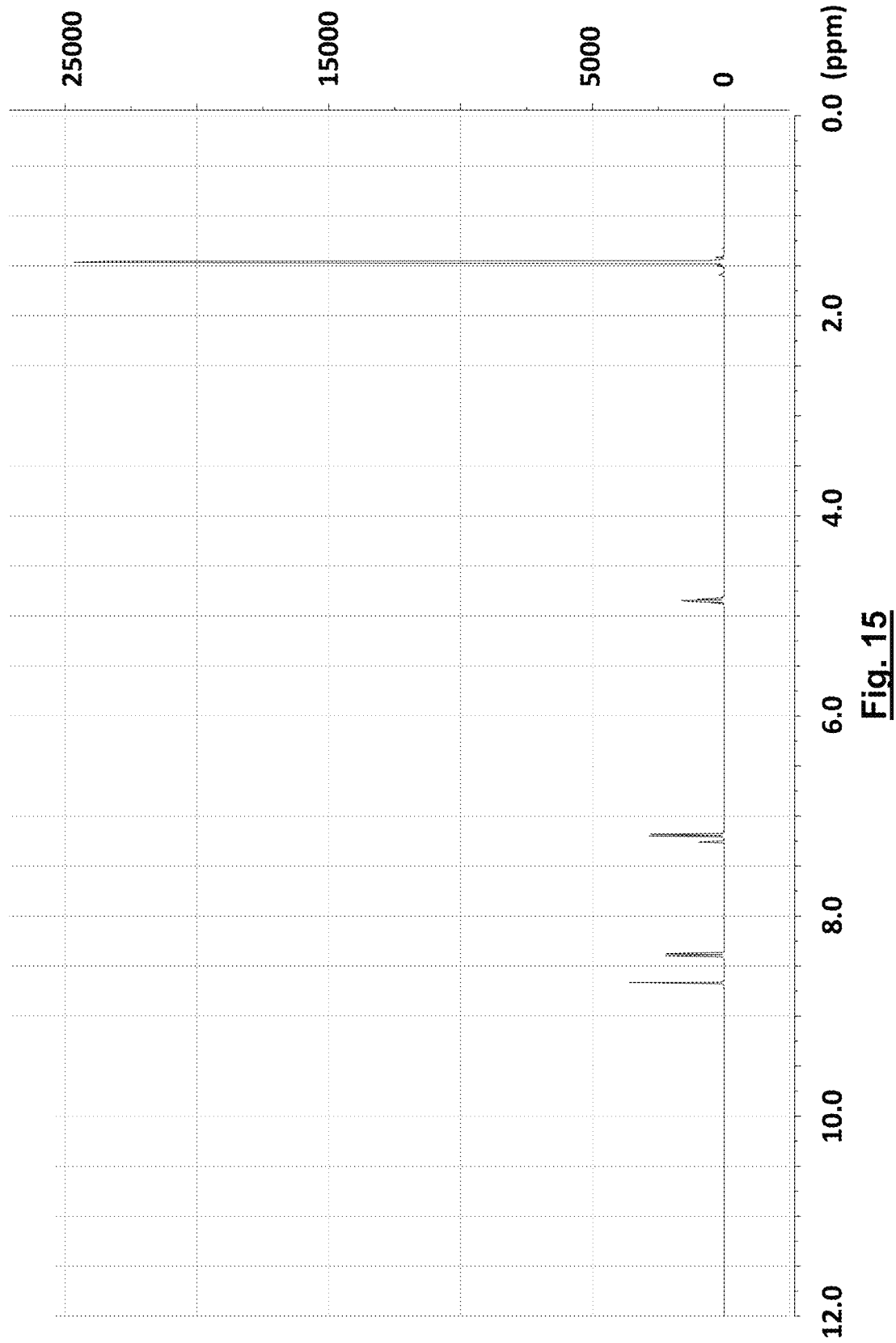
FIG. 15 illustrates the $^1$H NMR spectrum of DNPIE (compound 8) in $CDCl_3$.
Figure 16:
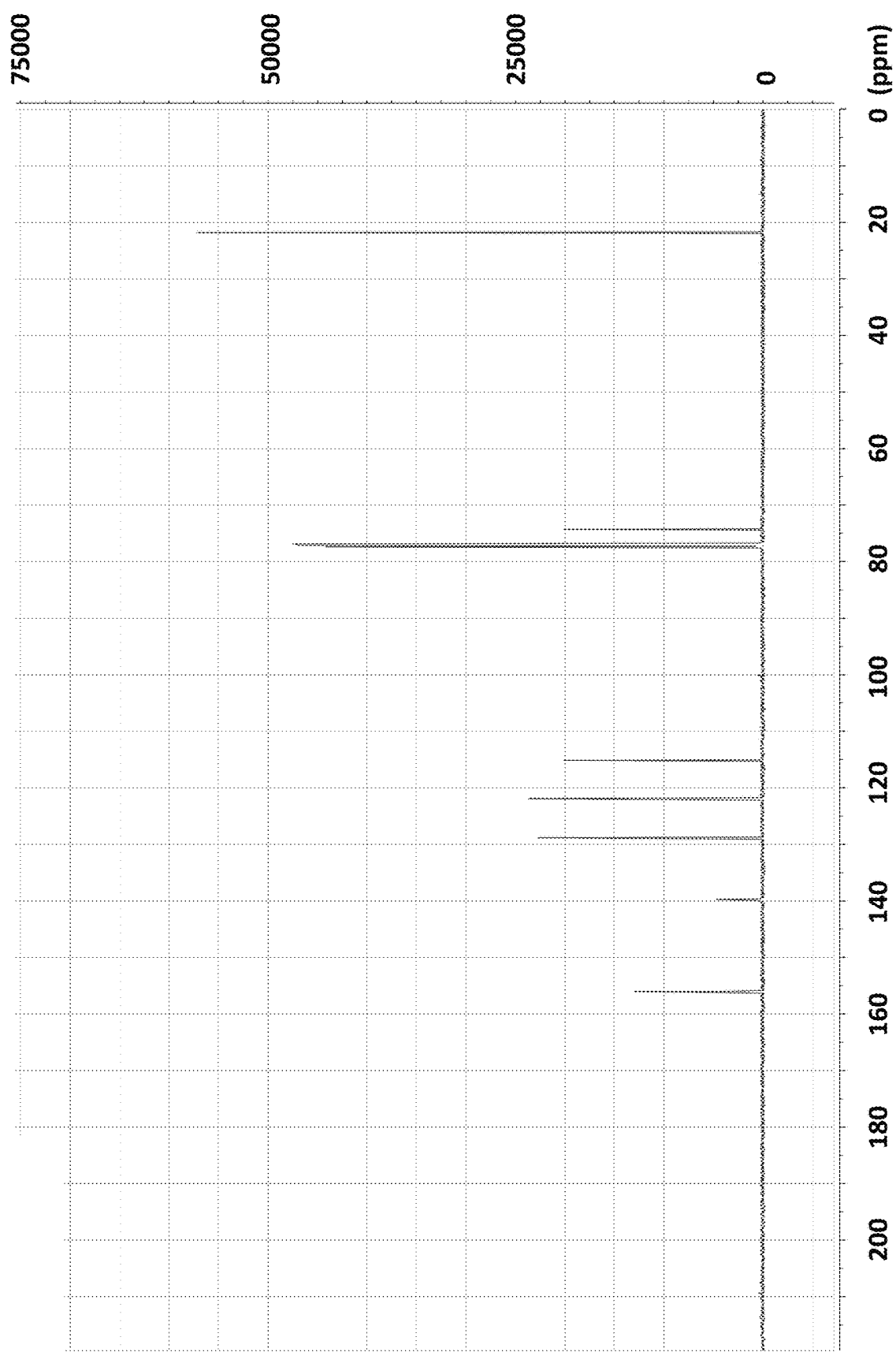
FIG. 16 illustrates the $^{13}$C NMR spectrum of DNPIE (compound 8) in $CDCl_3$.
Figure 17:
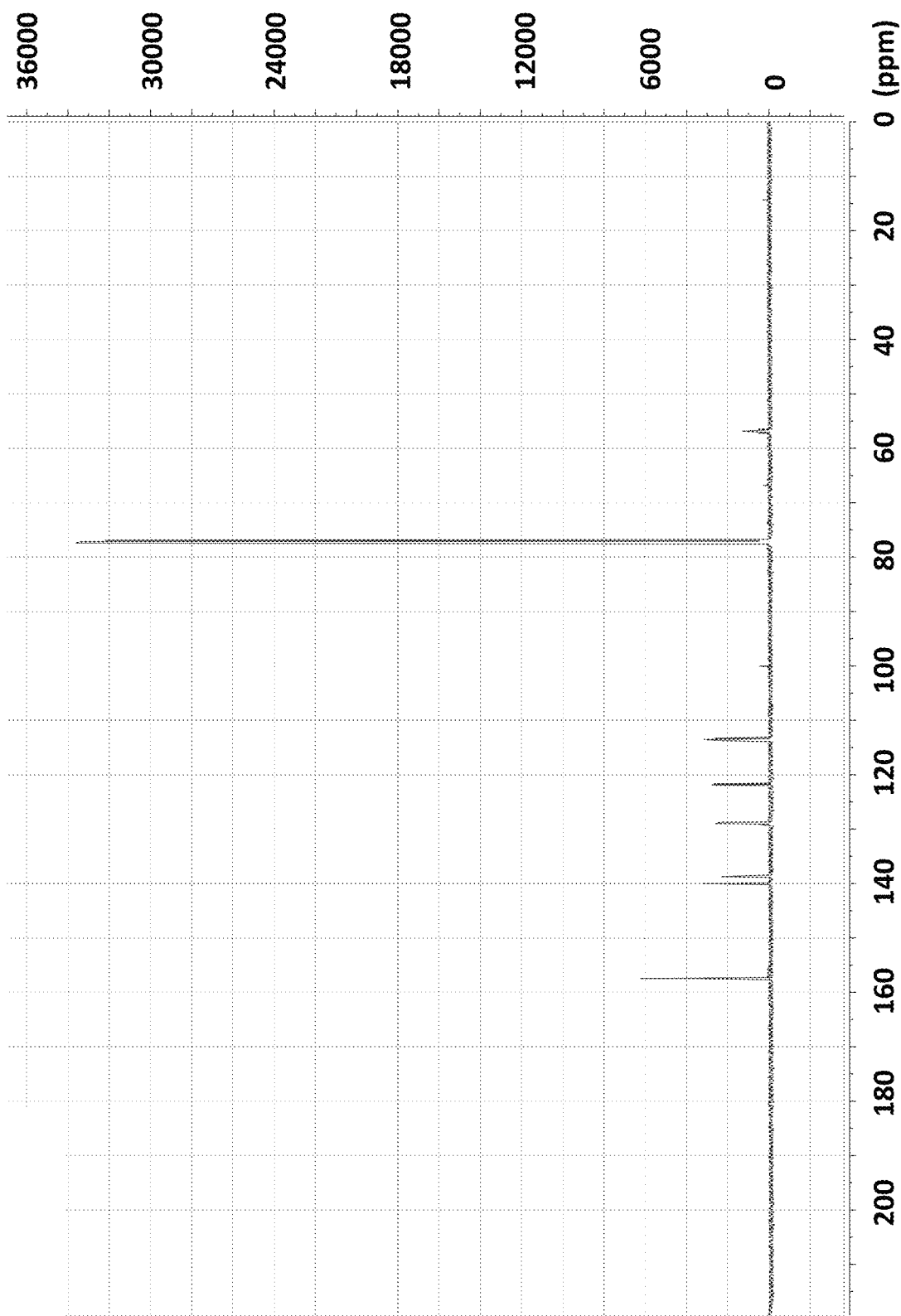
FIG. 17 illustrates the $^{13}$C NMR spectrum of DNPME-d$_6$ (compound 9) in $CDCl_3$.
Figure 18:
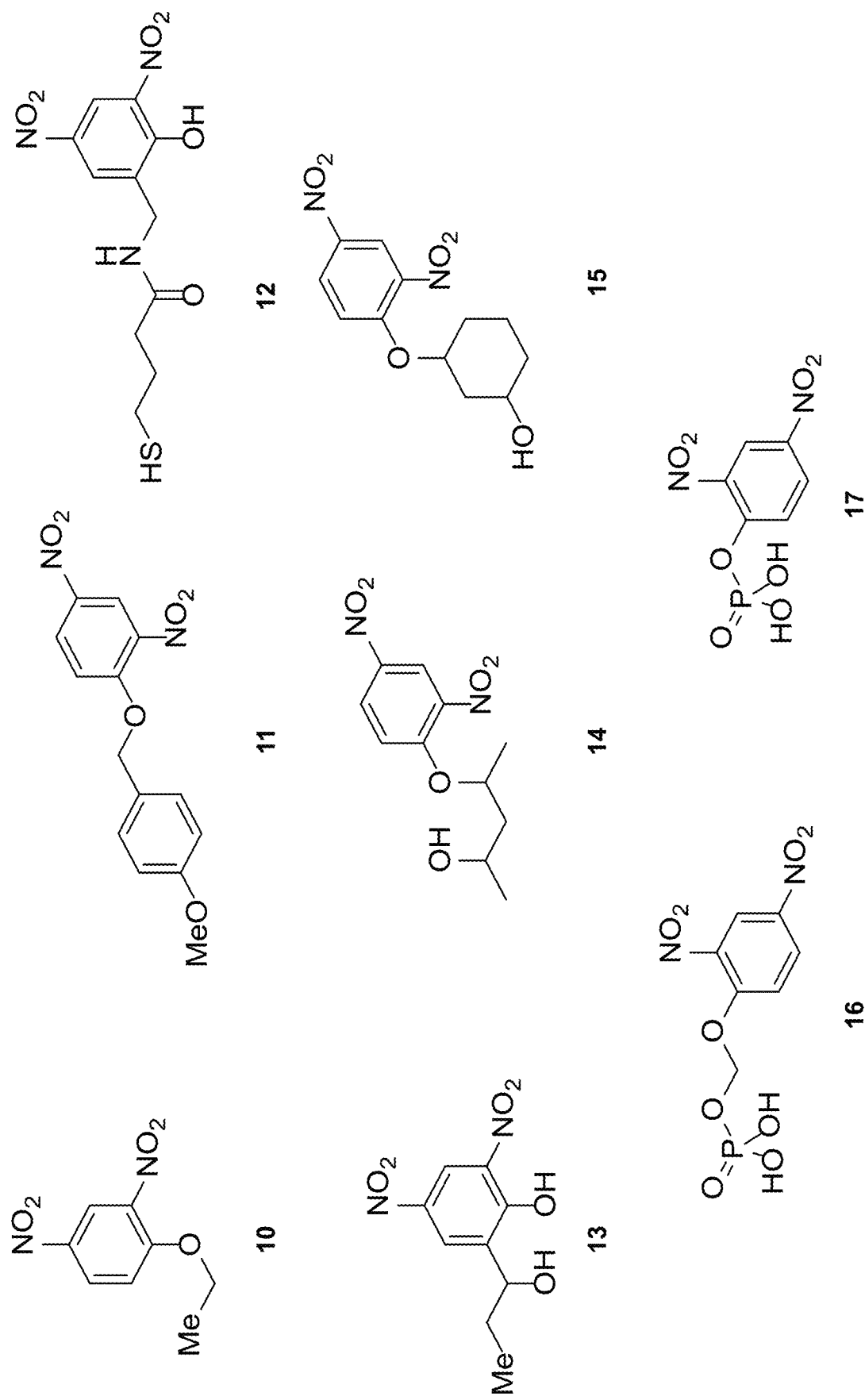
FIG. 18 illustrates the structures of exemplary compounds useful in the invention: 2,4-dinitrophenyl ethyl ether (compound 10), 1-((4-methoxybenzyl)oxy)-2,4-dinitrobenzene (MBn-DNP; compound 11), N-(2-hydroxy-3,5-dinitrobenzyl)-4-mercaptobutanamide (MBAM-DNP; compound 12), 2-(1-hydroxypropyl)-4,6-dinitrophenol (HP-DNP; compound 13), 4-(2,4-dinitrophenoxy)pentan-2-ol (compound 14), 3-(2,4-dinitrophenoxy)cyclohexanol (compound 15), (2,4-dinitrophenoxy)methyl dihydrogen phosphate (compound 16), and 2,4-dinitrophenyl dihydrogen phosphate (compound 17).
Figure 19:
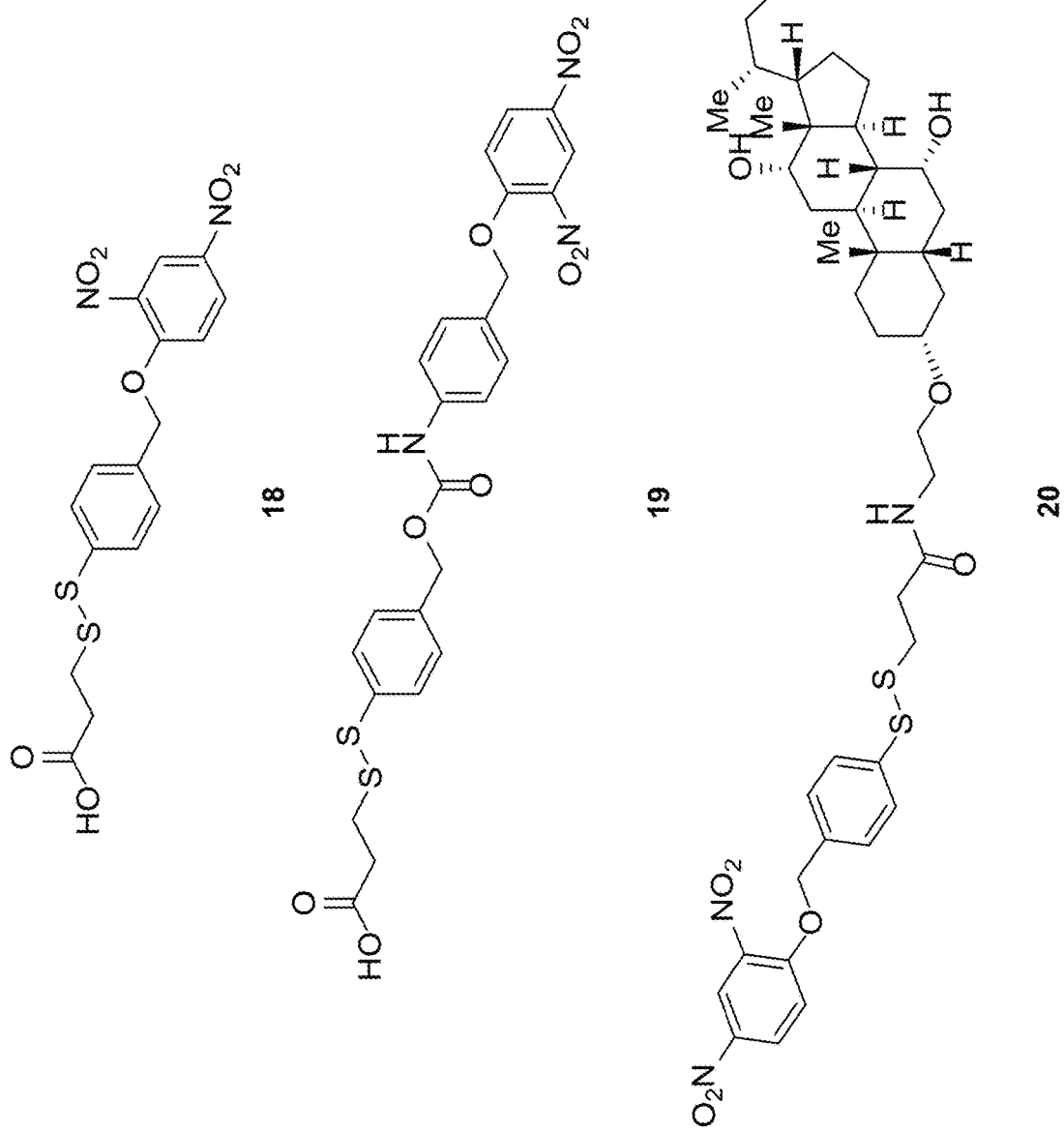
FIG. 19 illustrates the structures of exemplary compounds useful in the invention: 3-((4-((2,4-dinitrophenoxy)methyl)phenyl)disulfanyl)propanoic acid (compound 18), 3-((4-((((4-((2,4-dinitrophenoxy)methyl)phenyl)carbamoyl)oxy)methyl)phenyl)disulfanyl) propanoic acid (compound 19), and (R)-4-((3R,5R,7R,8R,9S,10S,12S,13R,14S,17S)-3-(2-(3-((4-((2,4-dinitrophenoxy)methyl)phenyl)disulfanyl)propanamido)ethoxy)-7,12-dihydroxy-10,13-dimethylhexadecahydro-1H-cyclopenta[a]phenanthren-17-yl)pentanoic acid (compound 20).
Figure 20:
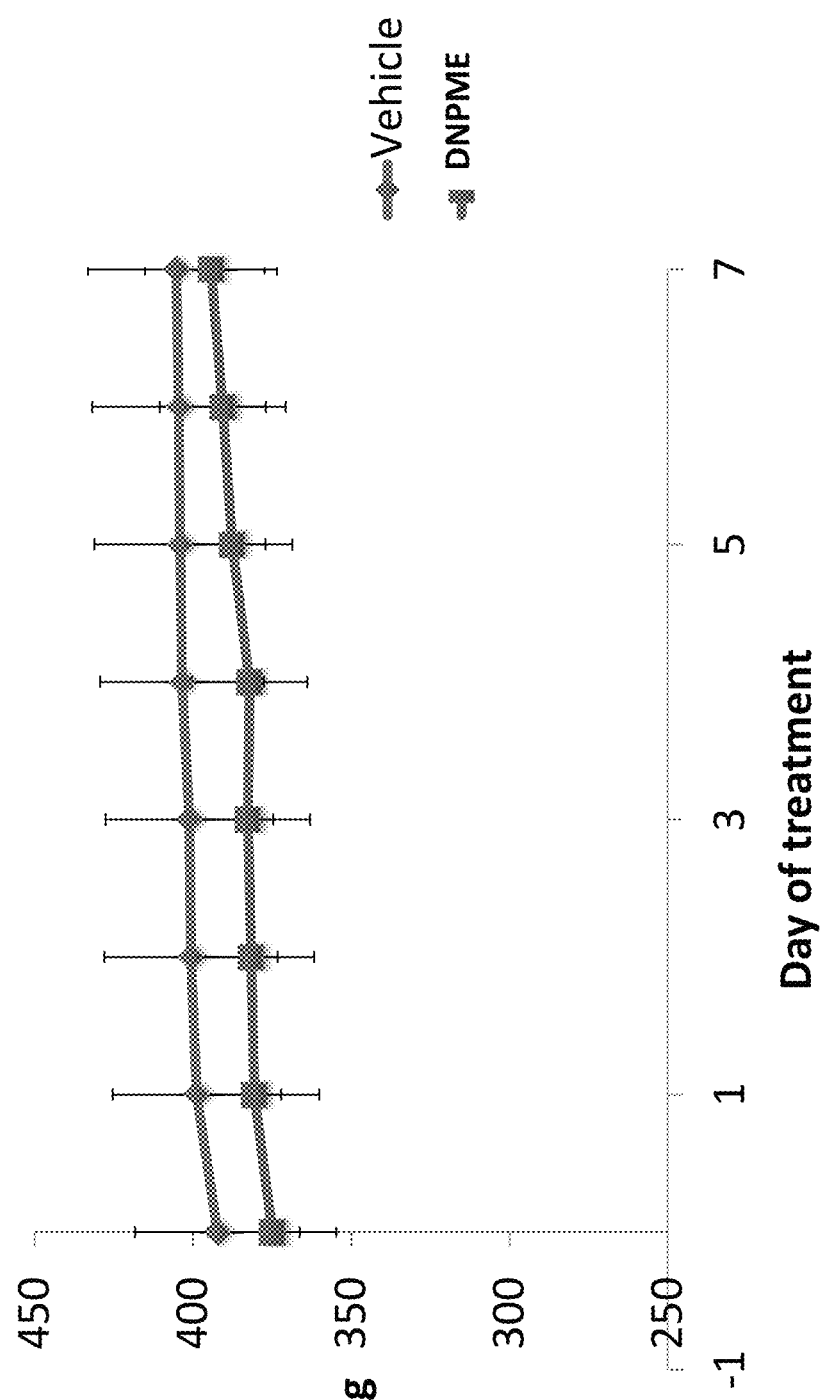
FIG. 20 is a graph illustrating the finding that body weight does not differ between rats treated with vehicle or with 7 days of DNPME treatment.
Figure 21:
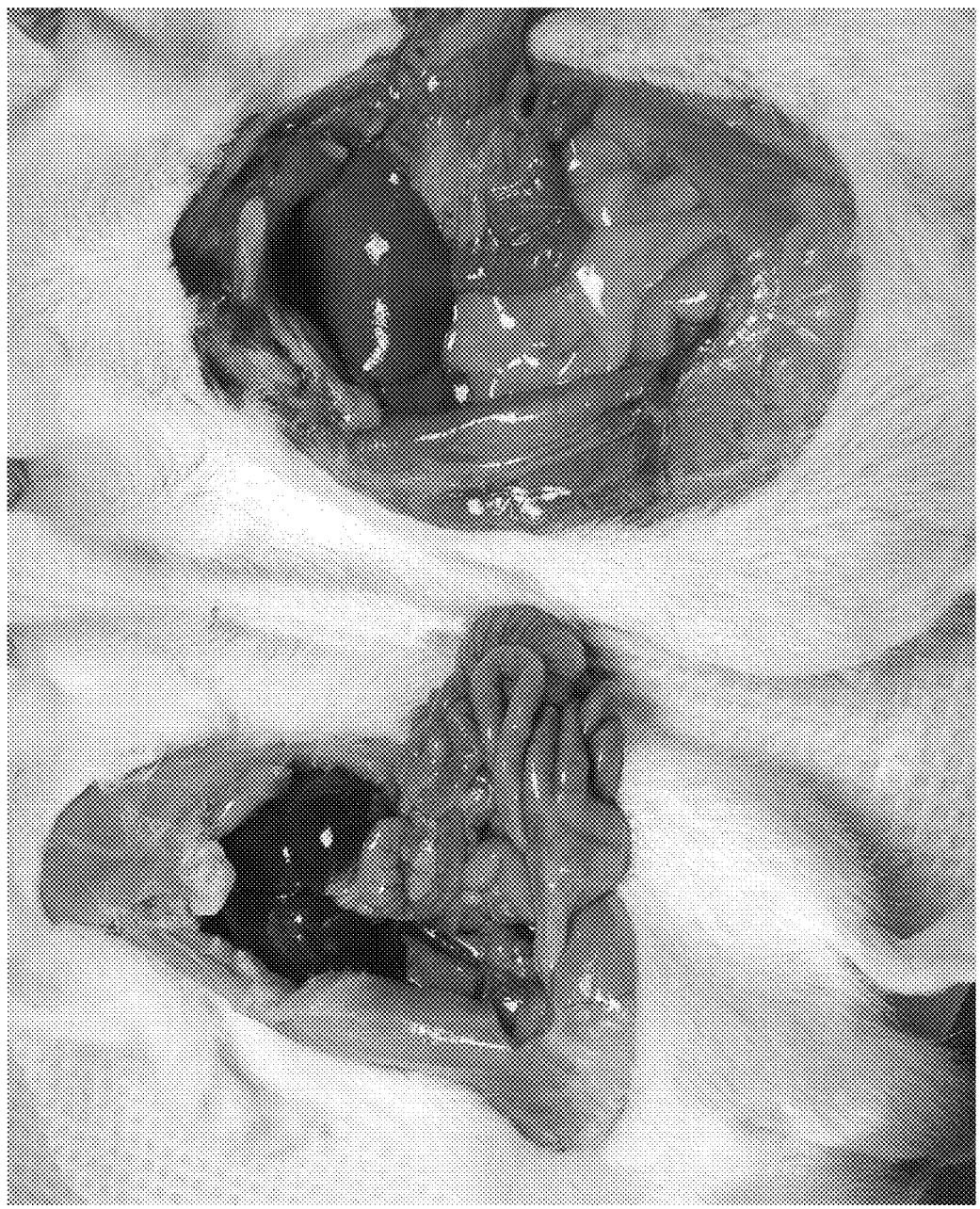
FIG. 21 is a photograph illustrating visible reductions in visceral fat and hepatic steatosis between rats treated with vehicle and rats treated with DNPME.
Figure 22:
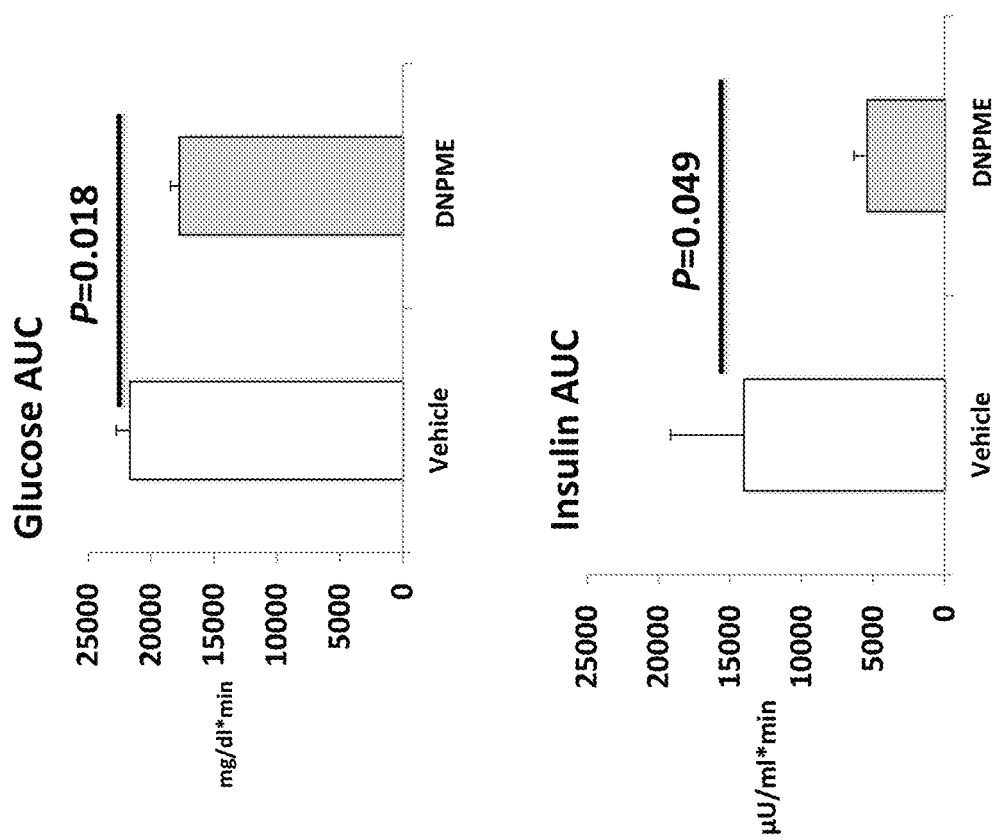
FIG. 22 is a series of graphs illustrating the finding that treatment with DNPME prevents glucose intolerance.
Figure 23:
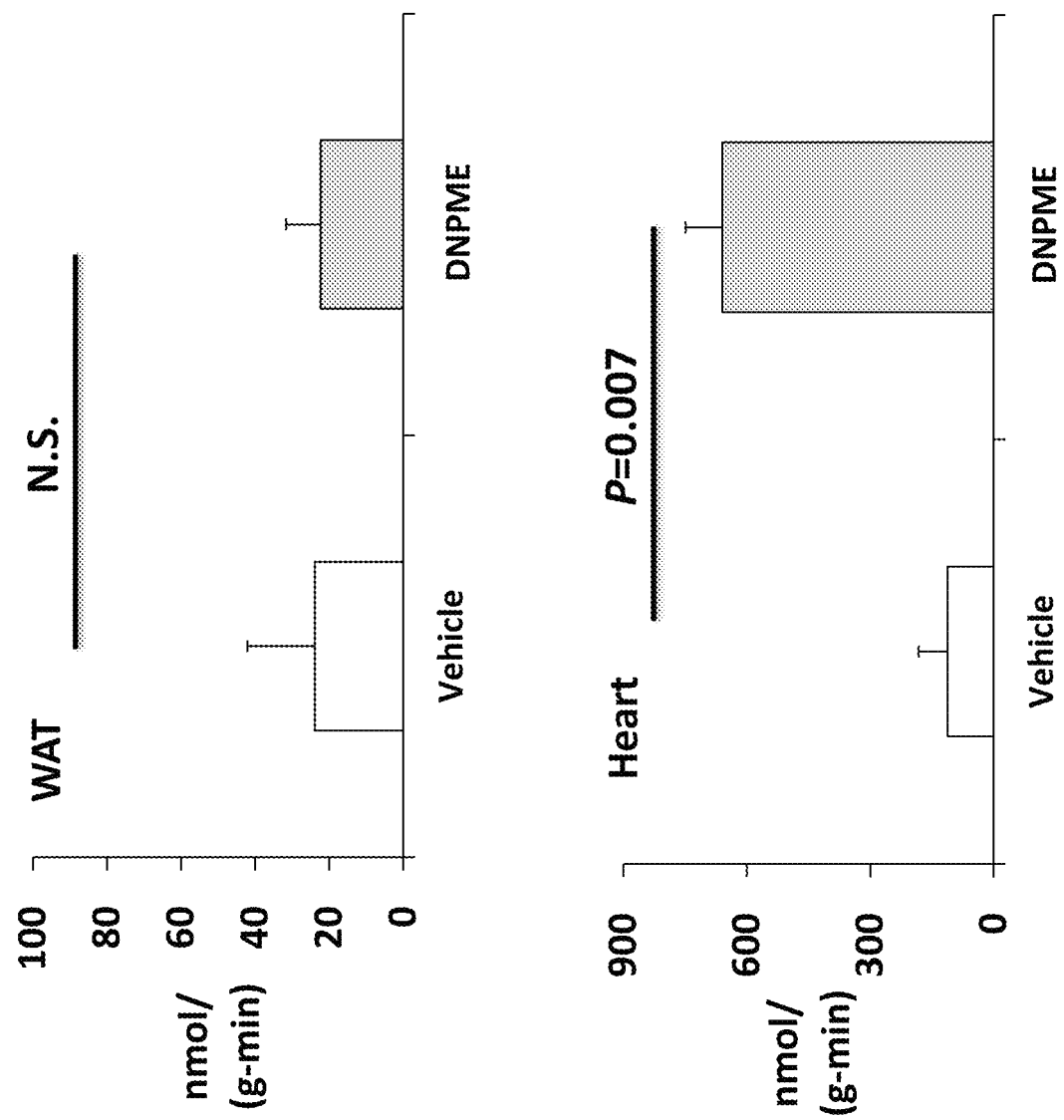
FIG. 23 is a series of graphs illustrating the finding that DNPME treatment increases peripheral glucose uptake.
Figure 24:
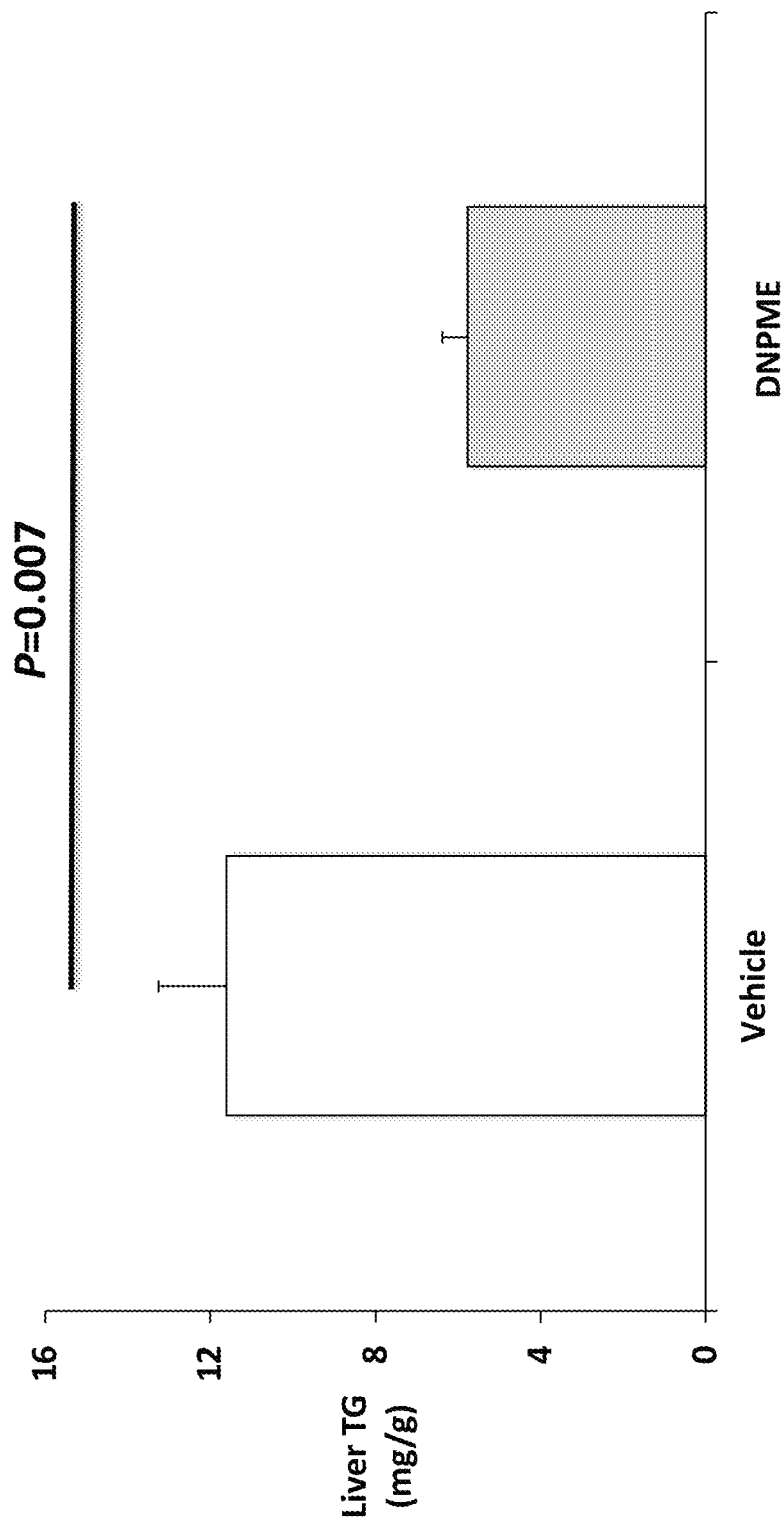
FIG. 24 is a graph illustrating the finding that DNPME treatment reverses NAFLD in high fat fed rats.
Figure 25:
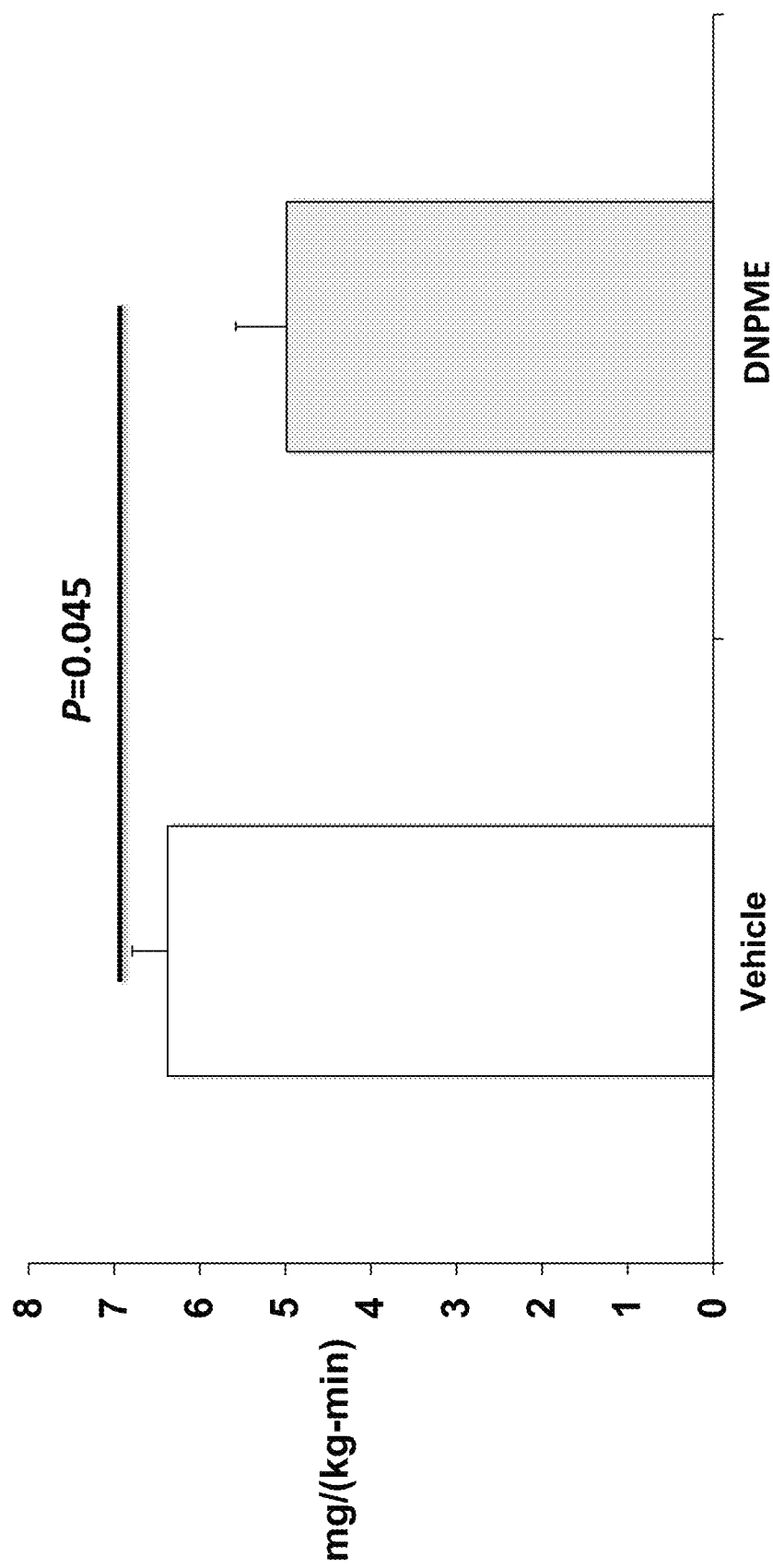
FIG. 25 is a graph illustrating the finding that treatment with DNPME corrects basal hepatic glucose production in high fat fed rats.
Figure 26:
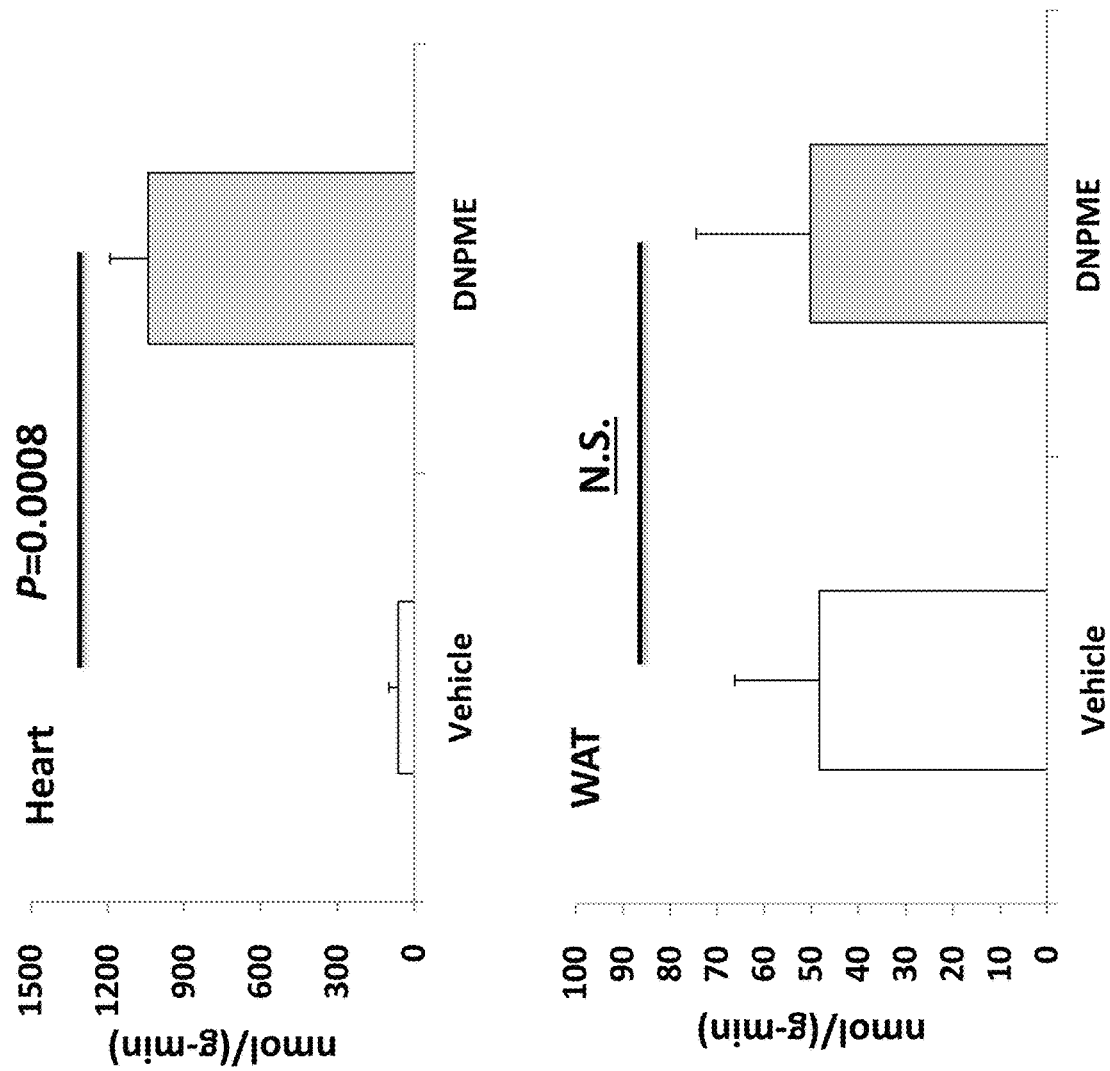
FIG. 26 is a graph illustrating the finding that DNPME treatment increases cardiac glucose uptake in an insulin resistant rodent model of NAFLD.
Figure 28:
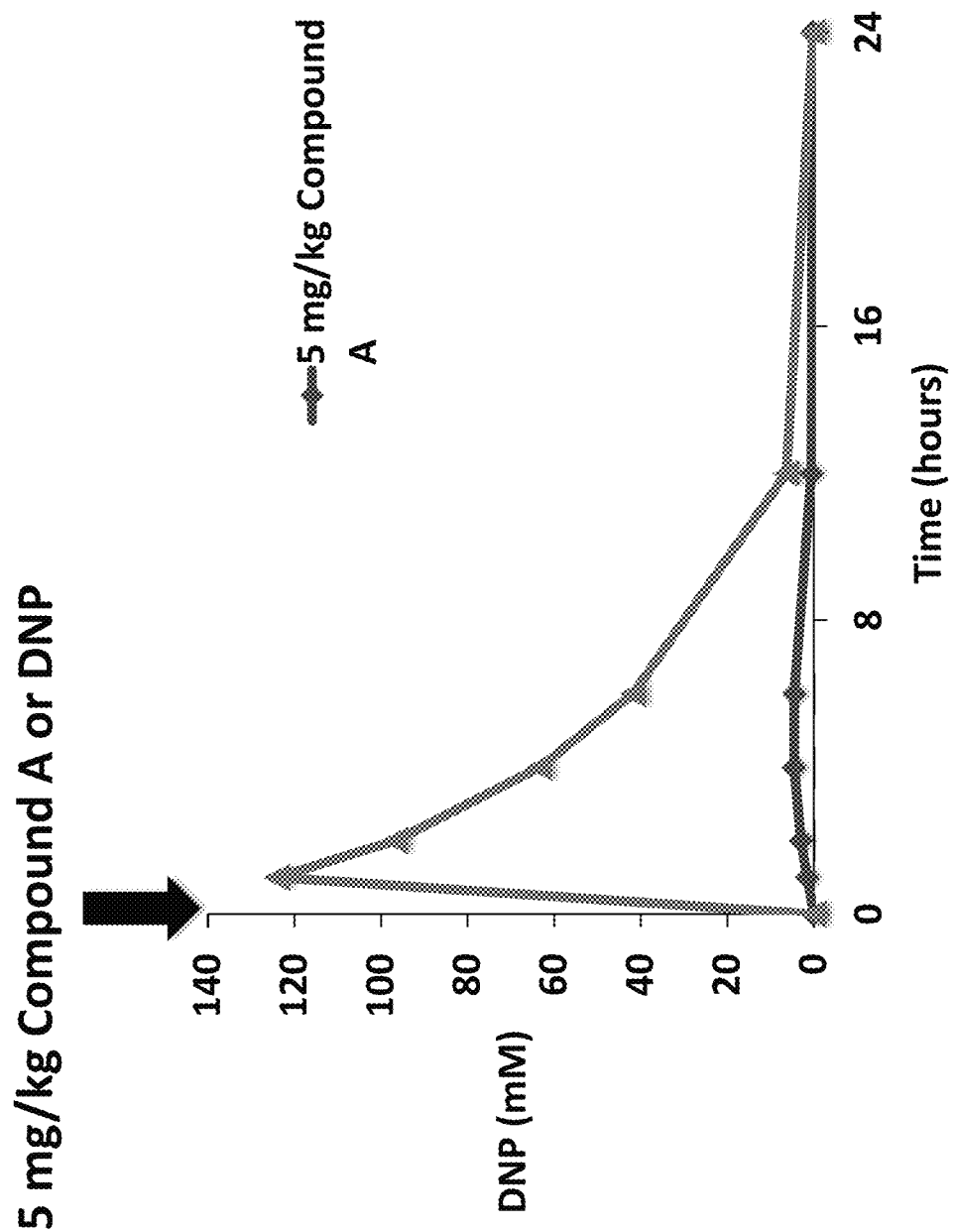
FIG. 28 is a graph illustrating a kinetics study evaluating plasma DNP and DNPME concentrations after injection of DNPME (5 mg/kg).
Figure 29:
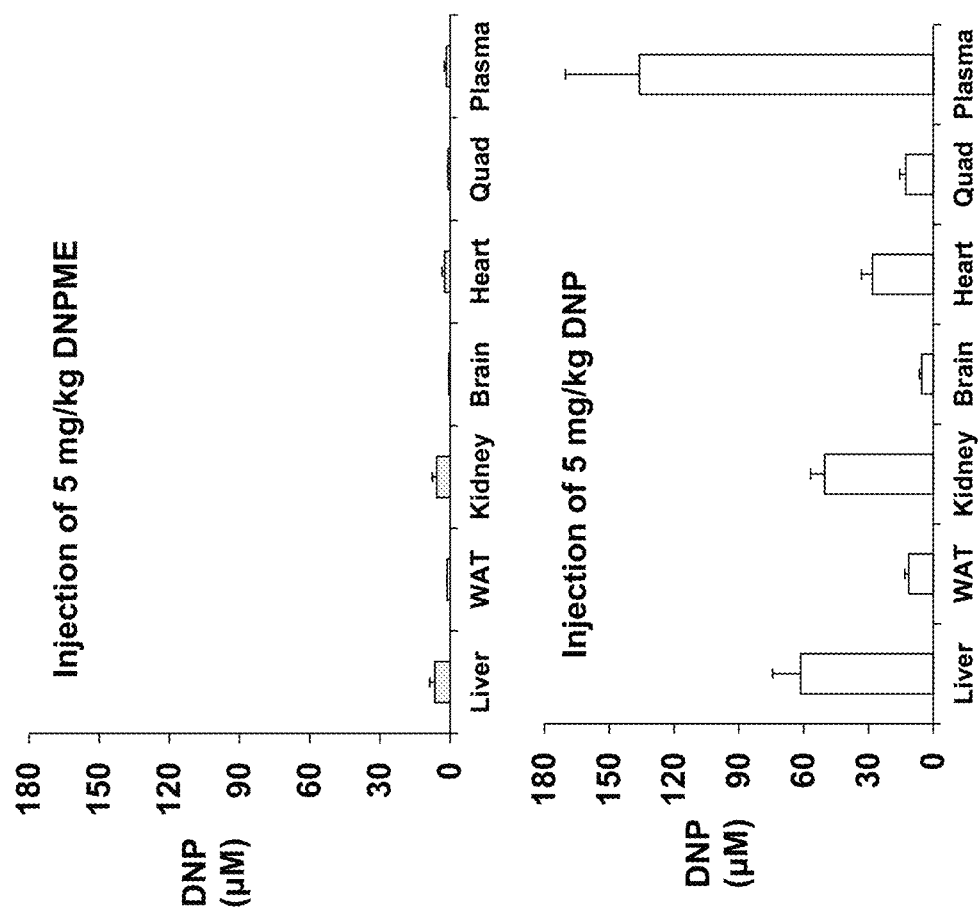
FIG. 29 is a series of graphs illustrating DNP and DNPME concentration in tissues after a single dose of DNPME (5 mg/kg) or DNP (5 mg/kg).
Figure 30:
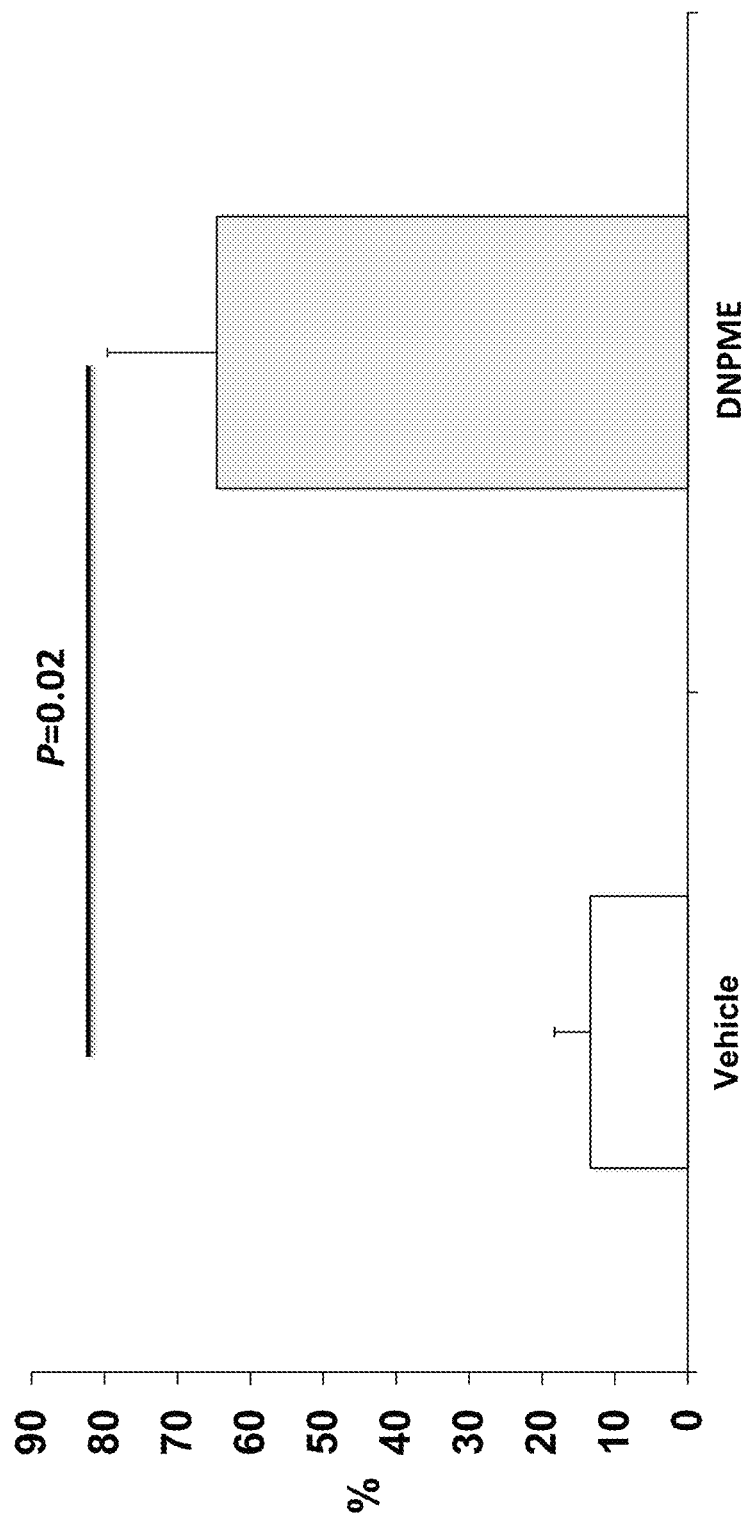
FIG. 30 is a graph illustrating the finding that DNPME treatment prevents hepatic insulin resistance. Rats were fed high fat diet for two weeks and were concurrently injected daily with 5 mg/kg of DNPME or vehicle.
Figure 31:
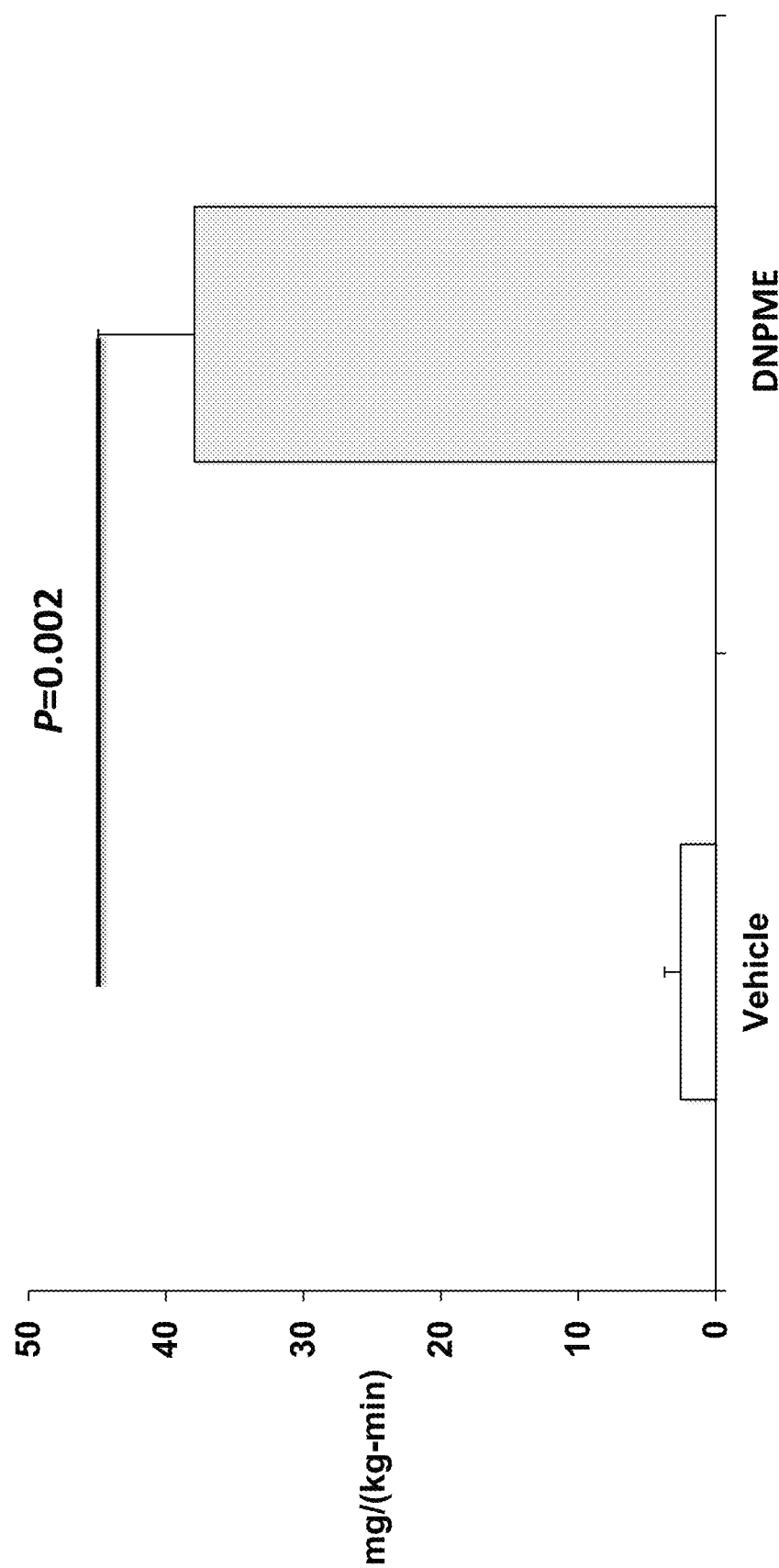
FIG. 31 is a graph illustrating the finding that DNPME treatment prevents peripheral muscle insulin resistance. Rats were fed high fat diet for two weeks and were concurrently injected daily with 5 mg/kg of DNPME or vehicle.
Figure 32:
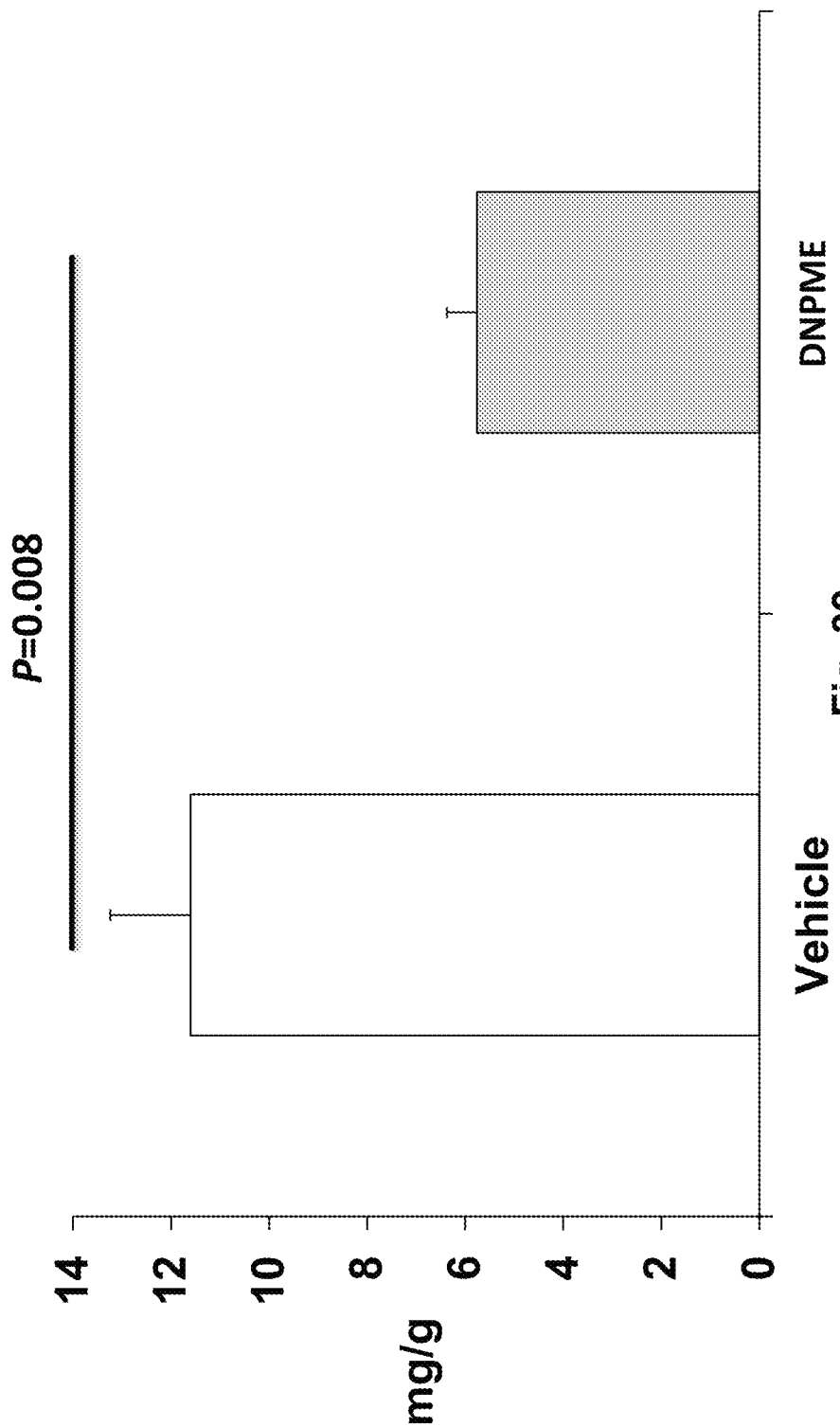
FIG. 32 is a graph illustrating the finding that DNPME prevents NAFLD.
Figure 33:
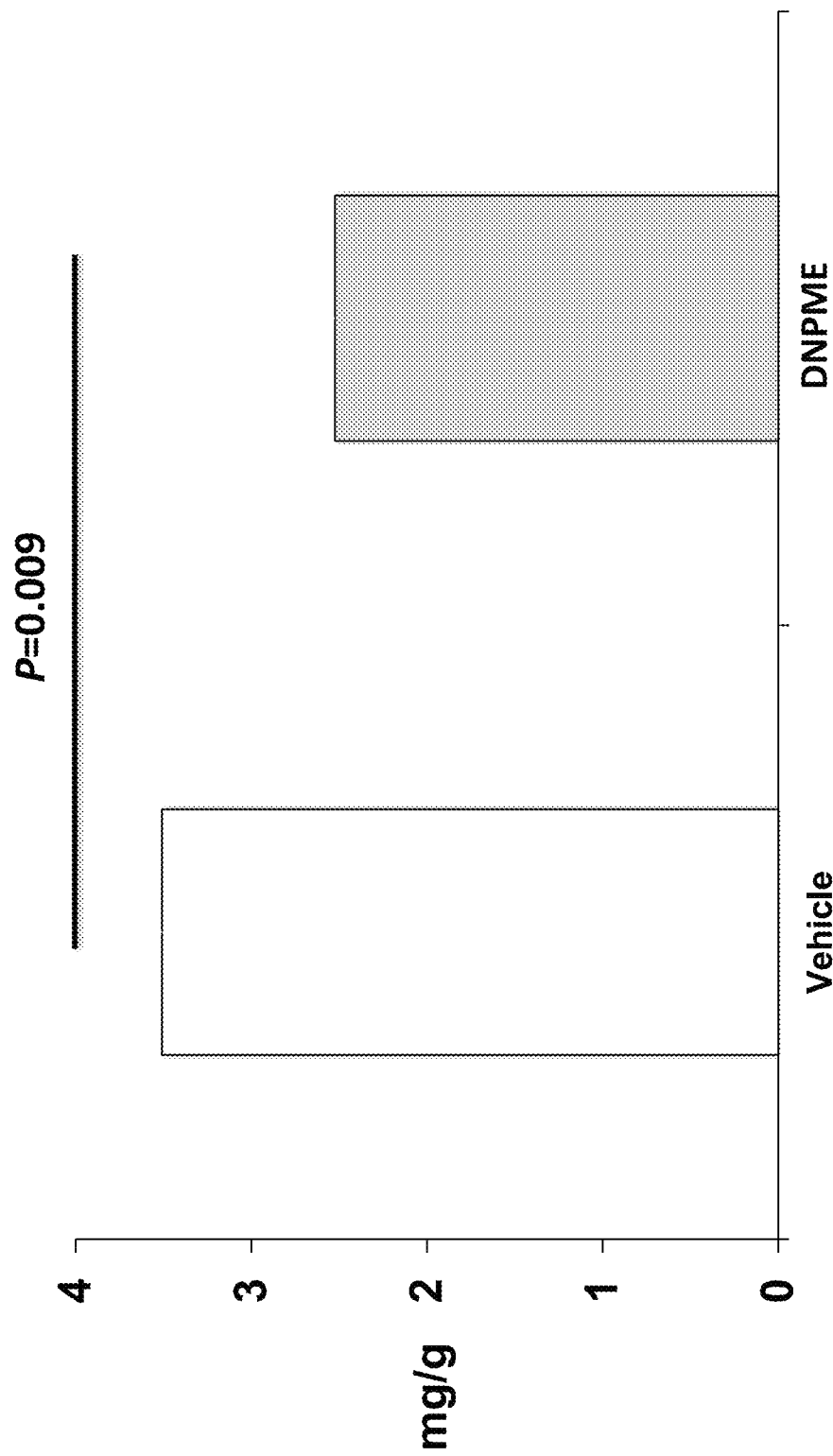
FIG. 33 is a graph illustrating the finding that DNPME prevents skeletal muscle triglyceride accumulation.

In order to examine the impact of DNPME on whole body energy expenditure and other metabolic parameters, metabolic cage (CLAMS) studies were performed in DNPME and vehicle treated mice. No effects of DNPME (5 mg/kg per day) were observed on whole body oxygen consumption, carbon dioxide production, energy expenditure, respiratory quotient, or activity (FIGS. 8A-8E). Consistent with the rat studies, no effect of DNPME was observed on food intake (FIG. 8F). Although not wishing to be bound by any particular theory, when taken together these data suggest that DNPME at a dose of 5 mg/kg per day promotes subtle increases in hepatic energy uncoupling that can result in major reductions in liver and muscle fat content with associated reversal of liver and muscle insulin resistance without a major impact on whole body energy expenditure.

DNPME does not Alter the Intracellular Energy Charge or Activate AMPK

It was also hypothesized that low circulating levels of DNP, derived from hepatic conversion of DNPME to DNP by the P450 system, promotes low levels of mitochondrial uncoupling in muscle and other extra-hepatic organs. In order to examine this hypothesis, mitochondrial uncoupling was assessed in vitro and uncoupling of liver but not brain by DNPME was observed, whereas DNP uncoupled both tissues in isolated mitochondria. In contrast, neither DNP nor DNPME was found to uncouple whole-cell brain preparations and similarly uncoupled skeletal or cardiac muscle or kidney at the plasma concentrations measured in the in vivo animal DNPME treatment studies (FIGS. 8G-8K). These data indicate that at the dose of DNPME administered in vivo, the uncoupling effect of DNPME appears to be restricted to the liver and can be mostly attributed to local conversion of DNPME to DNP (FIGS. 8G-8J). In addition, no differences were observed in ATP/AMP, ATP/ADP or NADH/NAD$^+$ ratios in liver and skeletal muscle, or in phosphorylation of hepatic AMP-activated protein kinase (AMPK) or its downstream target acetyl CoA carboxylase (ACC), demonstrating that DNPME is not altering the intracellular energy charge in these tissues at this therapeutic dose (FIGS. 8L-8R).

Figures 4A, 4B, 4C, 4D:
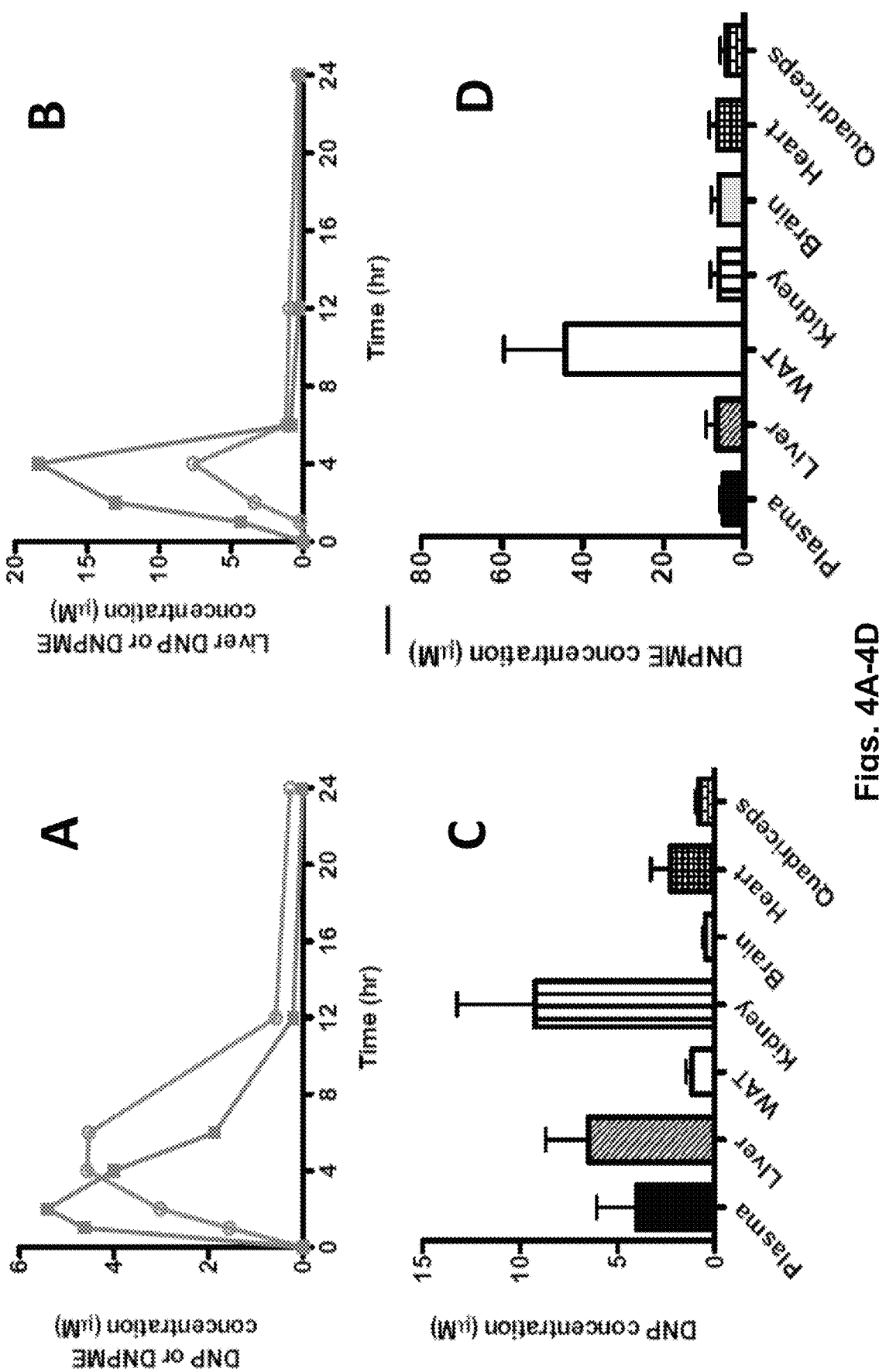
FIGS. 4A-4I, illustrates plasma and tissue kinetics of DNP and DNPME metabolism in the rat.

Low Intracellular Concentrations of DNP May be Sufficient to Achieve Significant Liver Mitochondrial Uncoupling In order to gain further insights into why DNPME does not result in hyperthermia at similar doses as DNP, plasma and tissue levels of DNP and DNPME were measured by LC-MS/MS. Dosing rats with DNPME at 5 mg/kg by intraperitoneal injection resulted in peak plasma DNP concentrations of ~5 µM and peak liver DNP concentrations of ~8 µM (FIGS. 4A-4B). DNP concentrations in all tissues were below 10 µM, while DNPME accumulated in WAT but not any other tissue (FIGS. 4C-4D). In contrast, the same dose of DNP (5 mg/kg) resulted in a peak plasma DNP concentration of ~120 µM and peak DNP liver concentrations of ~60 µM (FIG. 4E).

Figures 4E, 4F, 4G, 4H:
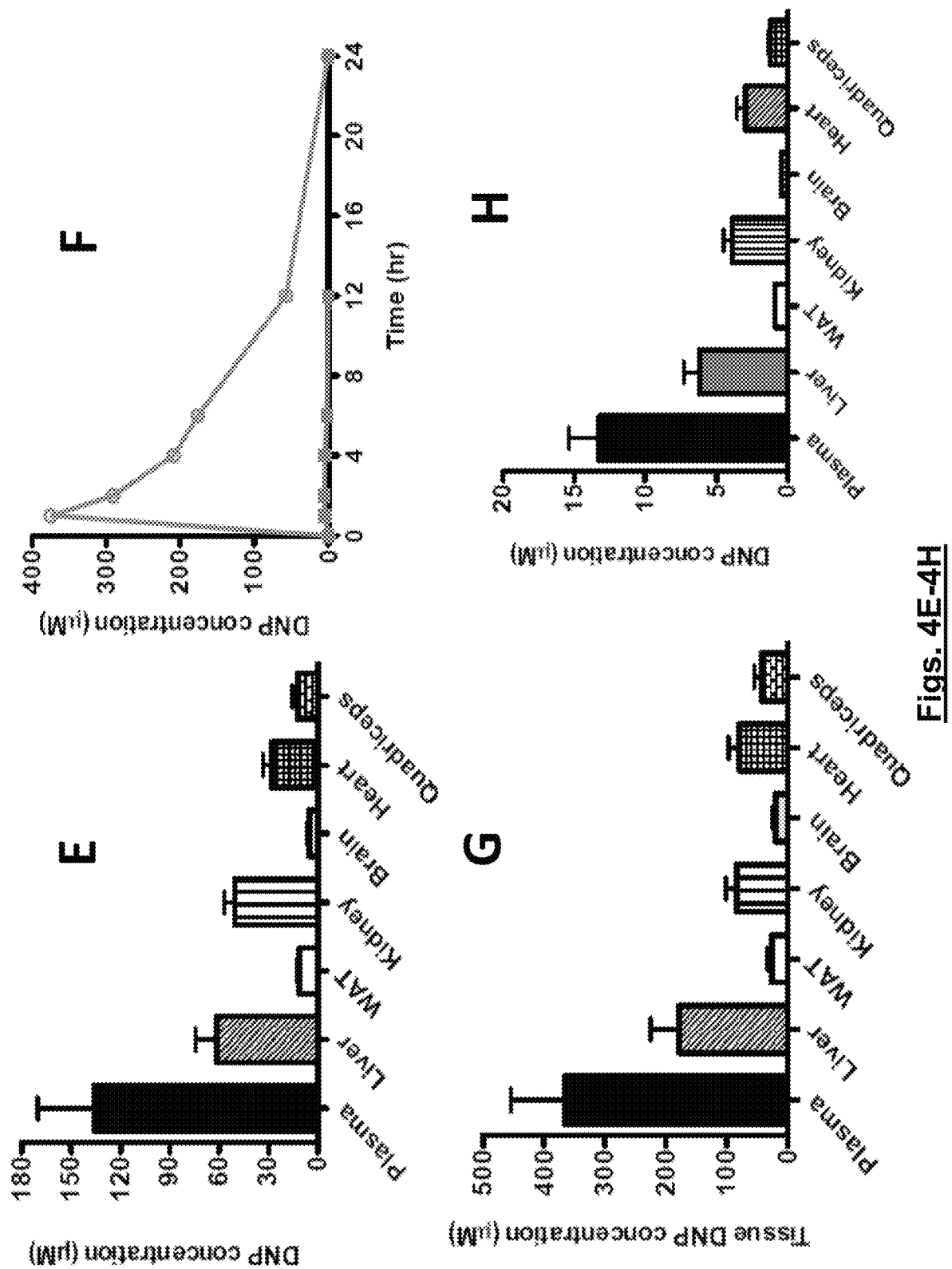
Figure 4I:
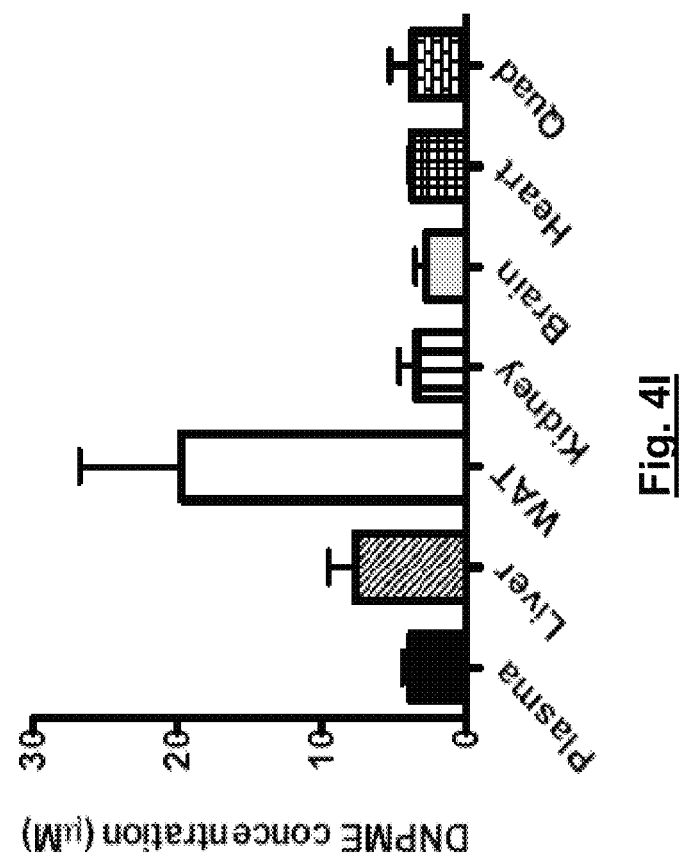

In order to determine how these plasma concentrations of DNP compare with toxic levels of DNP, plasma and liver concentrations of DNP were examined at the lowest dose of DNP (25 mg/kg) where systemic toxicities may be observed, and peak plasma DNP concentrations were found to be ~380 µM (FIGS. 4F-4G). Importantly, a week of treatment with DNPME resulted in tissue DNP and DNPME concentrations similar to those following a one-time DNPME injection (FIGS. 4H-4I). Although not wishing to be bound by any particular theory, these data suggest that very low intracellular concentrations of DNP, which are more than 75 fold lower than toxic levels of DNP (380 µM) are sufficient to achieve significant liver mitochondrial uncoupling, resulting in reductions in ectopic lipid content and hepatic triglyceride export as well as reversing liver and muscle insulin resistance, without resulting in hyperthermia and associated systemic toxicities.

Example 2: General Experimental Procedures for Chemical Synthesis

Chemicals were obtained from commercial sources and used as received, unless noted otherwise. In particular, 2,4-dinitrophenol (DNP; compound 1) was purchased from MP Biomedicals, 2,4-dinitrophenyl methyl ether (DNPME; compound 2) from Alfa Aesar, and 1-chloro-2,4-dinitrobenzene-d3 (compound 3) from C/D/N Isotopes.

NMR Spectra were measured at ambient temperature unless otherwise noted. $^1$H NMR spectra were recorded on either a 500 or 400 MHz Bruker spectrometer. Chemical shifts are reported in ppm (δ) relative to tetramethylsilane, using the solvent as a reference (CDCl$_3$=7.26 ppm). The following is an example data point: chemical shift (multiplicity [s=singlet, d=doublet, t=triplet, q=quartet, m=multiplet, br=broad, and combinations thereof], coupling constants [Hz], integration). $^{13}$C NMR spectra were recorded on a 500 MHz (126 MHz) or 400 MHz (101 MHz) Bruker spectrometer with complete proton decoupling. Chemical shifts are reported in ppm ($\delta$) relative to tetramethylsilane using the solvent as a reference (CDCl$_3$=77.16 ppm). MS data were obtained with an Agilent 6890/5973 GC/MSD System. Yield refers to isolated material.

Synthesis of 2,4-dinitrophenyl Boronic Acid (DNPBA; Compound 4)

DNPBA (compound 4) was synthesized (Collibee and Yu, 2005, Tet. Lett. 47:4453-4455).

Synthesis of 2,4-dinitrophenyl Methyl Ether (DNPME; Compound 2)

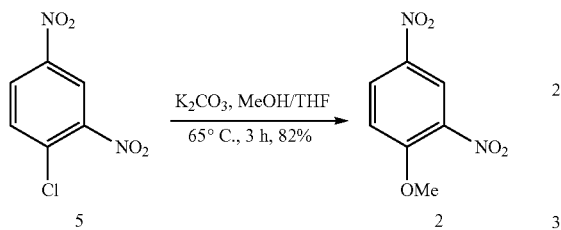

DNMPE (compound 2) was synthesized using previously described methods with minor modifications (Gong et al., 2002, Dyes and Pigments 53:109-117). Briefly, aryl chloride 5 (4.05 g; 20 mmol) was dissolved in MeOH/THF (3.2 ml/2 ml), treated with K$_2$CO$_3$ (4.70 g; 34 mmol) and heated at 65° C. for 3 h in a sealed tube. The reaction mixture was then diluted with dichloromethane (50 ml) and washed twice with 3% NaHCO$_3$ solution. The organic layers were combined, dried over Na$_2$SO$_4$ and concentrated to afford pure DNMPE as a pale yellow solid (3.25 g; 82%). $^1$H NMR (400 MHz, CDCl$_3$) $\delta$ 8.74 (d, J=2.8, 1H), 8.45 (dd, J=9.3, 2.8, 1H), 7.24 (d, J=9.2, 1H), 4.10 (s, 3H); $^{13}$C NMR (101 MHz, CDCl$_3$) $\delta$ 157.43, 140.27, 138.95, 129.29, 122.02, 113.78, 57.62; IR (film, cm$^{-1}$) 3101, 1598, 1520, 1342, 1279; MS (e.i.) m/z 198 [M$^+$, 42%].

Synthesis of 2,4-dinitrophenyl Vinyl Ether (DNPVE; Compound 6)

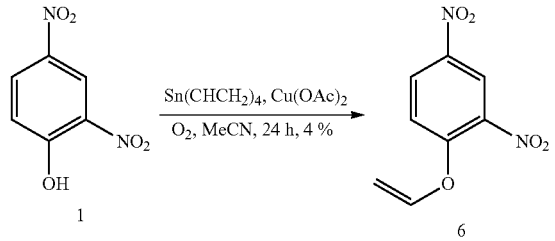

DNPVE was prepared from 2,4-dinitrophenol (1, 184 mg; 1 mmol) (Blouin and Frenette, 2001, J. Org. Chem. 66:9043-9045). After SiO$_2$ chromatography (10-30% EtOAc/hexane), DNPVE was obtained as a pale yellow gum (9 mg; 4%). $^1$H NMR (400 MHz, CDCl$_3$) $\delta$ 8.80 (d, J=2.7, 1H), 8.44 (dd, J=9.2, 2.8, 1H), 7.33 (d, J=9.2, 1H), 6.68 (dd, J=13.5, 5.9, 1H), 5.18 (dd, J=13.4, 2.6, 1H), 4.93 (dd, J=5.8, 2.5, 1H); $^{13}$C NMR (101 MHz, CDCl$_3$) $\delta$ 154.44, 145.03, 141.93, 139.38, 129.07, 122.18, 117.75, 102.77; IR (film, cm$^{-1}$) 1600, 1527, 1338, 1264; MS (e.i.) m/z 180 [(M−NO)$^+$, 7%].

Synthesis of 2,4-dinitrophenyl Allyl Ether (DNPAE; Compound 7)

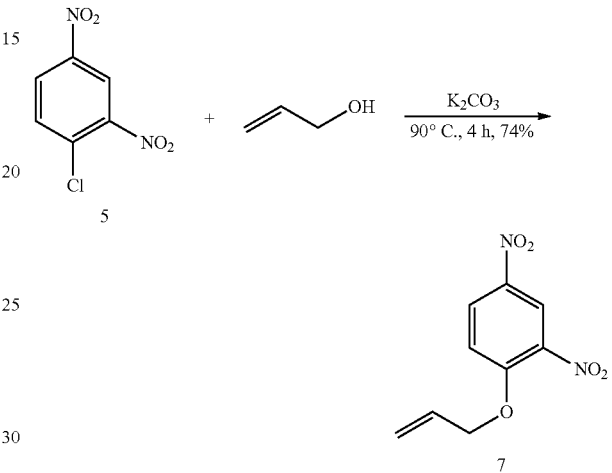

DNPAE (compound 7) was synthesized from aryl chloride 5 (4.05 g; 20 mmol), using the same method as described above for the synthesis of DNPME (compound 2), except substituting allyl alcohol (5.4 ml) for MeOH/THF. DNPAE was obtained as a yellow solid (3.297 g; 74%). $^1$H NMR (400 MHz, CDCl$_3$) $\delta$ 8.72 (d, J=2.8, 1H), 8.40 (dd, J=9.2, 2.8, 1H), 7.22 (d, J=9.2, 1H), 6.03 (ddt, J=17.3, 10.3, 5.0, 1H), 5.51 (dq, J=17.3, 1.6, 1H), 5.40 (dq, J=10.7, 1.4, 1H), 4.83 (dt, J=5.0, 1.6, 2H); $^{13}$C NMR (101 MHz, CDCl$_3$) $\delta$ 156.41, 140.19, 139.09, 130.41, 129.09, 121.97, 119.64, 114.92, 71.02; IR (film, cm$^{-1}$) 1604, 1521, 1488, 1340, 1313, 1279, 1242; MS (e.i.) m/z 224 [M$^+$, 3%].

Synthesis of 2,4-dinitrophenyl Isopropyl Ether (DNPIE; Compound 8)

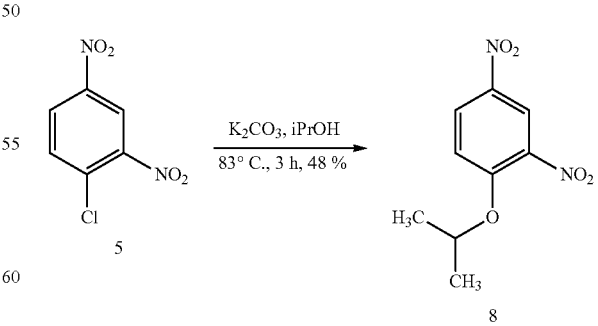

DNPIE (compound 8) was synthesized from aryl chloride 5 (1.02 g; 5 mmol), using the same method as described above for the synthesis of DNPME (compound 2), except substituting i-PrOH (1.5 ml) for MeOH/THF. DNPIE was obtained as a yellow solid (542 mg; 48%). $^1$H NMR (500 MHz, CDCl$_3$) δ 8.67 (d, J=2.8, 1H), 8.39 (dd, J=9.3, 2.8, 1H), 7.19 (d, J=9.4, 1H), 4.85 (hept, J=6.0, 1H), 1.46 (d, J=6.0, 6H); $^{13}$C NMR (126 MHz, CDCl$_3$) δ 156.05, 139.87, 139.71, 128.82, 121.93, 115.17, 74.32, 21.77; IR (film, cm$^{-1}$) 1604, 1521, 1486, 1340, 1311, 1282; MS (e.i.) m/z 226 [M$^+$, 3%].

Synthesis of 2,4-dinitrophenyl Methyl Ether-d6 (DNPME-d$_6$; Compound 9)

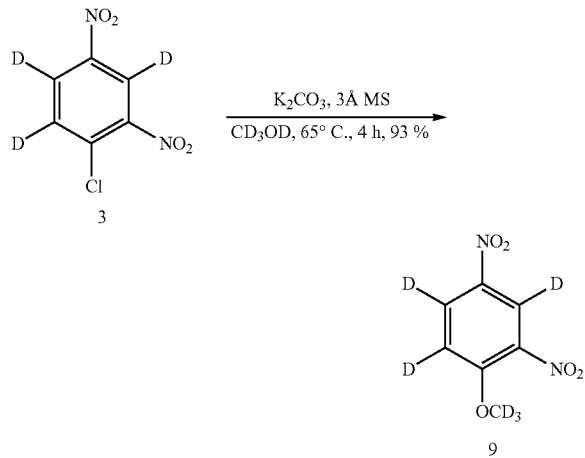

DNPME-d$_6$ (compound 9) was synthesized using the same method as described above for DNPME (compound 2) with minor modifications. 3 Å molecular sieves and K$_2$CO$_3$ (92 mg; 0.66 mmol) were added to a microwave vessel and flame-dried. To this were added aryl chloride 3 (80 mg; 0.39 mmol) and CD$_3$OD (0.6 ml). The reaction mixture was heated at 65° C. for 4 h in a microwave. The crude product was purified as described above for DNPME to afford DNPME-d6 (74 mg; 93%). $^{13}$C NMR (126 MHz, CDCl$_3$) δ 157.44, 140.01, 138.71, 128.96 (t, J=26.0), 121.68 (t, J=26.2), 113.52 (t, J=25.5), 56.84 (hept, J=22.3); IR (film, cm$^{-1}$) 2308, 1579, 1518, 1425, 1372, 1336, 1305, 1248; MS (e.i.) m/z 204 [M$^+$, 20%].

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of ameliorating a disease or disorder in a subject in need thereof, wherein the disease or disorder is at least one selected from the group consisting of hypertriglyceridemia, fatty liver, and insulin resistance, the method comprising:
   administering to the subject a therapeutically effective amount of a nitrophenyl derivative selected from the group consisting of 2,4-dinitrophenyl vinyl ether, 2,4-dinitrophenyl methyl ether-d$_6$, and solvates thereof.

2. The method of claim 1, wherein the method further comprises administering to the subject at least one additional therapeutic agent.

3. The method of claim 2, wherein the nitrophenyl derivative and the at least one additional therapeutic agent are co-administered to the subject.

4. The method of claim 3, wherein the nitrophenyl derivative and the at least one additional therapeutic agent are co-formulated.

5. The method of claim 1, wherein the subject is a mammal.

6. The method of claim 5, wherein the mammal is human.

7. The method of claim 1, wherein the administering is by an administration route selected from the group consisting of oral, transdermal, transmucosal, intravesical, intrapulmonary, intraduodenal, intragastrical, intrathecal, subcutaneous, intramuscular, intradermal, intra-arterial, intravenous, intrabronchial, inhalation, and topical.

8. The method of claim 7, wherein the administering is oral and wherein the nitrophenyl derivative is formulated as a tablets, dragee, liquid, drop, capsule, caplet, or gelcap.

9. A method of increasing energy expenditure in a subject afflicted with at least one disease or disorder selected from the group consisting of non-alcoholic fatty liver disease (NAFLD), non-alcoholic steatohepatitis (NASH), hepatic steatosis, type 2 diabetes (T2D), acquired lipodystrophy, lipodystrophy (inherited), partial lipodystrophy, hypertriglyceridemia, obesity, metabolic syndrome, Rett's syndrome, Friedreich's ataxia, and insulin resistance, the method comprising:
   administering to the subject a therapeutically effective amount of a nitrophenyl derivative selected from the group consisting of 2,4-dinitrophenyl vinyl ether, 2,4-dinitrophenyl methyl ether-d$_6$, and solvates thereof,
   whereby energy expenditure in the subject is increased.

10. The method of claim 9, wherein the therapeutically effective amount of the nitrophenyl derivative is about 25 µmoles/kg.

11. The method of claim 9, wherein the subject is a mammal.

12. The method of claim 11, wherein the mammal is human.

13. The method of claim 9, wherein the administering is by an administration route selected from the group consisting of oral, transdermal, transmucosal, intravesical, intrapulmonary, intraduodenal, intragastrical, intrathecal, subcutaneous, intramuscular, intradermal, intra-arterial, intravenous, intrabronchial, inhalation, and topical.

14. The method of claim 13, wherein the administering is oral and wherein the nitrophenyl derivative is formulated as a tablets, dragee, liquid, drop, capsule, caplet, or gelcap.

15. A method of uncoupling mitochondria in the liver of a subject, the method comprising:
   administering to the subject a therapeutically effective amount of a nitrophenyl derivative selected from the group consisting of 2,4-dinitrophenyl methyl ether, 2,4-dinitrophenyl vinyl ether, 2,4-dinitrophenyl methyl ether-d$_6$, and solvates thereof,
   wherein mitochondria in the liver of the subject are selectively uncoupled.

16. The method of claim 15, wherein the subject is a mammal.

17. The method of claim 15, wherein the mammal is human.

18. The method of claim 15, wherein the administering is by an administration route selected from the group consisting of oral, transdermal, transmucosal, intravesical, intrapulmonary, intraduodenal, intragastrical, intrathecal, subcutaneous, intramuscular, intradermal, intra-arterial, intravenous, intrabronchial, inhalation, and topical.

19. The method of claim 18, wherein the administering is oral and wherein the nitrophenyl derivative is formulated as a tablets, dragee, liquid, drop, capsule, caplet, or gelcap.

20. The method of claim 15, wherein the nitrophenyl derivative is administered in an amount of about 0.1 mg to about 1000 mg to the subject.

* * * * *

UNITED STATES PATENT AND TRADEMARK OFFICE
CERTIFICATE OF CORRECTION

| | | |
|---|---|---|
| PATENT NO. | : 10,781,161 B2 | Page 1 of 1 |
| APPLICATION NO. | : 16/419949 | |
| DATED | : September 22, 2020 | |
| INVENTOR(S) | : Gerald I. Shulman and David A. Spiegel | |

It is certified that error appears in the above-identified patent and that said Letters Patent is hereby corrected as shown below:

In the Specification

Column 1, Lines 18-24, replace the existing paragraph with the following paragraph:
-- STATEMENT REGARDING FEDERALLY SPONSORED RESEARCH OR DEVELOPMENT
This invention was made with government support under DK085638 and DK045735 awarded by National Institutes of Health. The government has certain rights in the invention. --

Signed and Sealed this
Tenth Day of November, 2020

Andrei Iancu
*Director of the United States Patent and Trademark Office*